(12) United States Patent
Coats et al.

(10) Patent No.: US 10,011,629 B2
(45) Date of Patent: Jul. 3, 2018

(54) NUCLEOSIDE ANALOGS FOR TREATMENT OF THE FLAVIVIRIDAE FAMILY OF VIRUSES AND CANCER

(71) Applicants: Cocrystal Pharma, Inc., Tucker, GA (US); Emory University, Atlanta, GA (US)

(72) Inventors: Steven J. Coats, McDonough, GA (US); Franck Amblard, Decatur, GA (US); Seema Mengshetti, Decatur, GA (US); Hao Li, Decatur, GA (US); Raymond F. Schinazi, Miami, FL (US)

(73) Assignees: Cocrystal Pharma, Inc., Tucker, GA (US); Emory University, Atlanta, GA (US)

(*) Notice: Subject to any disclaimer, the term of this patent is extended or adjusted under 35 U.S.C. 154(b) by 0 days.

(21) Appl. No.: 15/139,924

(22) Filed: Apr. 27, 2016

(65) Prior Publication Data
US 2017/0233428 A1    Aug. 17, 2017

Related U.S. Application Data

(60) Provisional application No. 62/155,939, filed on May 1, 2015, provisional application No. 62/246,980, filed on Oct. 27, 2015.

(51) Int. Cl.
| | | |
|---|---|---|
| *C07H 19/06* | (2006.01) | |
| *C07H 19/10* | (2006.01) | |
| *C07H 19/16* | (2006.01) | |
| *A61K 9/00* | (2006.01) | |
| *A61K 9/14* | (2006.01) | |
| *A61K 45/06* | (2006.01) | |
| *A61K 31/7072* | (2006.01) | |

(52) U.S. Cl.
CPC ......... *C07H 19/10* (2013.01); *A61K 9/0014* (2013.01); *A61K 9/14* (2013.01); *A61K 31/7072* (2013.01); *A61K 45/06* (2013.01); *C07H 19/06* (2013.01); *C07H 19/16* (2013.01)

(58) Field of Classification Search
None
See application file for complete search history.

(56) References Cited

U.S. PATENT DOCUMENTS

2017/0057981 A1* 3/2017 Chen ................. C07F 9/08

FOREIGN PATENT DOCUMENTS

| WO | 2010091386 A2 | 8/2010 |
| WO | 2012158811 A3 | 11/2012 |
| WO | 2014070771 A1 | 5/2014 |

OTHER PUBLICATIONS

Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
International Search Report dated Dec. 15, 2016 for PCT Application No. PCT/US2016/029527.

* cited by examiner

*Primary Examiner* — Traviss C McIntosh, III
(74) *Attorney, Agent, or Firm* — Hunton Andrews Kurth LLP; David Bradin

(57) ABSTRACT

The present invention is directed to compounds, compositions and methods for treating or preventing Flaviviridae family of viruses (including HCV, Yellow fever, Dengue, Chikungunya and West Nile virus), RSV, HEV, and influenza infection and cancer in human subjects or other animal hosts.

17 Claims, 11 Drawing Sheets

Cellular Pharmacology: Triphosphate Production From 9 Versus Sofosbuvir in Huh-7

Cells

Cellular Pharmacology: Triphosphate Production From 9 Versus Sofosbuvir in Human Primary Hepatocytes Glucose

Galactose

Glucose

Galactose

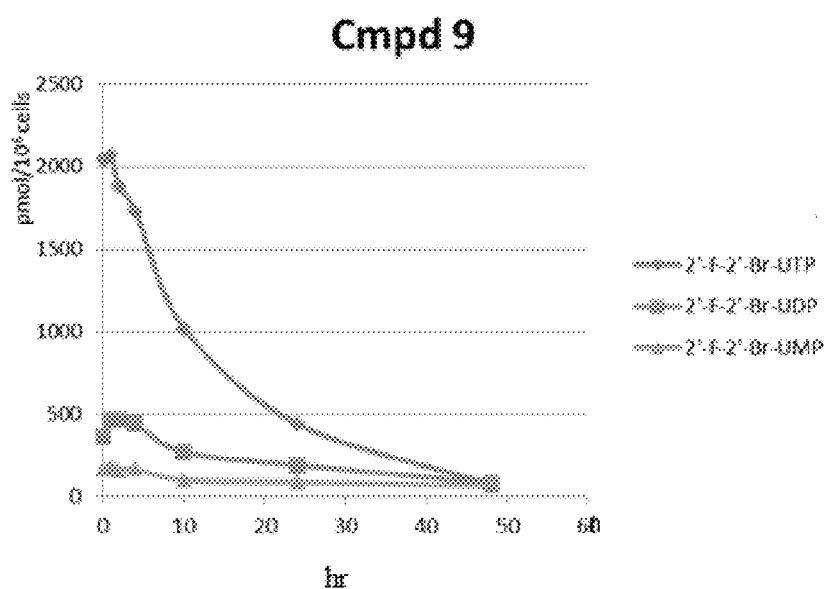
Figure 6a: Cellular egress of Compound 9 from Primary Human Hepatocytes

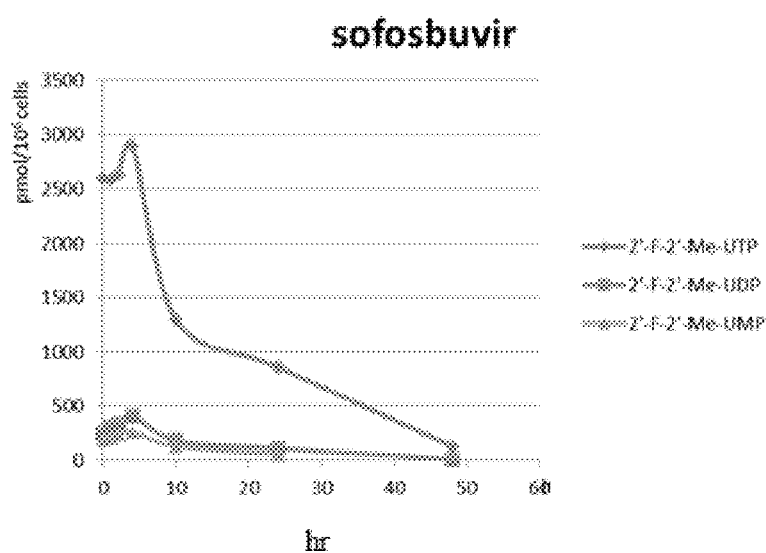
Figure 6b: Cellular egress of Sofosbuvir from Primary Human Hepatocytes

SEQUENCE LISTING

<160> NUMBER OF SEQ ID NOS: 11

<210> SEQ ID NO 1
<211> LENGTH: 17
<212> TYPE: DNA
<213> ORGANISM: Human

<400> SEQUENCE: 1
tgcccgccat catccta                                                17

<210> SEQ ID NO 2
<211> LENGTH: 21
<212> TYPE: DNA
<213> ORGANISM: Human

<400> SEQUENCE: 2
tcctcatcgc cctcccatcc c                                           21

<210> SEQ ID NO 3
<211> LENGTH: 23
<212> TYPE: DNA
<213> ORGANISM: Human

<400> SEQUENCE: 3
cgtctgttat gtaaaggatg cgt                                         23

<210> SEQ ID NO 4
<211> LENGTH: 17
<212> TYPE: DNA
<213> ORGANISM: human

<400> SEQUENCE: 4
gcgcggctac agcttca                                                17

<210> SEQ ID NO 5
<211> LENGTH: 18
<212> TYPE: DNA
<213> ORGANISM: Human

<400> SEQUENCE: 5
caccacggcc gagcggga                                               18

<210> SEQ ID NO 6
<211> LENGTH: 22
<212> TYPE: DNA
<213> ORGANISM: Human

<400> SEQUENCE: 6
tctccttaat gtcacgcacg at                                          22

<210> SEQ ID NO 7
<211> LENGTH: 12
<212> TYPE: RNA
<213> ORGANISM: Human

<400> SEQUENCE: 7
uuuugccgcg cc                                                     12

<210> SEQ ID NO 8
<211> LENGTH: 18
<212> TYPE: DNA
<213> ORGANISM: Human
<220> FEATURE:
<221> NAME/KEY: misc_feature

```
<222> LOCATION: (10)..(10)
<223> OTHER INFORMATION: n is a, c, g, or t

<400> SEQUENCE: 8
gggaatgcan ggcgcggc                                              18

<210> SEQ ID NO 9
<211> LENGTH: 24
<212> TYPE: DNA
<213> ORGANISM: Human

<400> SEQUENCE: 9
tcaggtccct gttcgggcgc cact                                       24

<210> SEQ ID NO 10
<211> LENGTH: 48
<212> TYPE: DNA
<213> ORGANISM: Human

<400> SEQUENCE: 10
cagtgtggaa aatctctagc agtggcgccc gaacagggac ctgaaagc             48

<210> SEQ ID NO 11
<211> LENGTH: 36
<212> TYPE: DNA
<213> ORGANISM: Human

<400> SEQUENCE: 11
tctctagaag tggcgcccga acagggacct gaaagc                          36
```

NUCLEOSIDE ANALOGS FOR TREATMENT OF THE FLAVIVIRIDAE FAMILY OF VIRUSES AND CANCER

FIELD OF THE INVENTION

The present invention is directed to compounds, methods and compositions for treating or preventing hepatitis C virus (HCV) infections as well as other flaviviruses, RSV, influenza and cancer. More specifically, the invention describes certain nucleoside and nucleotide analogs, pharmaceutically acceptable salts, or other derivatives thereof, and the use thereof in the treatment of flaviviruses, respiratory syncytial virus (RSV), hepatitis E virus (HEV), influenza and cancer.

BACKGROUND OF THE INVENTION

Hepatitis C virus (HCV) has infected more than 170 million people worldwide. It is estimated that three to four million persons are newly infected each year, 70% of whom will develop chronic hepatitis. HCV is responsible for 50-76% of all liver cancer cases, and two thirds of all liver transplants in the developed world. Standard of Care (SOC) therapy [pegylated interferon alfa plus ribavirin (a nucleoside analog)] is only effective in 50-60% of patients and is associated with significant side-effects. Similarly, addition of a first generation HCV protease inhibitor (such as brocepravir or telaprevir) to the SOC improves outcomes and the cure rate, but the side effects are usually severe. Therefore, there is an urgent need for new HCV drugs that are potent and safe.

Hepatitis C virus genome comprises a positive-strand RNA enclosed in a nucleocapsid and lipid envelope and consists of 9.6 kb ribonucleotides and has a single open reading frame (ORP) encoding which encodes a large polypeptide of about 3,000 amino acids (Dymock et al. Antiviral Chemistry & Chemotherapy 2000, 11, 79). Following maturation, this polypeptide is cut into at least 10 proteins by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases: 1) a metalloprotease that cleaves at the NS2-NS3 junction; and 2) a serine protease contained within the N-terminal region of NS3 (NS3 protease) which mediates all the subsequent cleavages downstream of NS3. The NS4A protein appears to serve multiple functions including the NS4A/NS3 complex formation, which appears to enhance the proteolytic efficiency of the NS3 protein. NS5B (also referred to herein as HCV polymerase), possesses polymerase activity and is involved in the synthesis of double-stranded RNA from the single-stranded viral RNA genome that serves as the template. NS5A is a nonstructural 56-58 kDa protein which modulates HCV replication as a component of replication complex. NS5A is highly phosphorylated by cellular protein kinases and the phosphorylation sites are conserved among HCV genotypes (Katze et al, 2001; Kim et al, 1999).

The discovery of novel antiviral strategies to selectively inhibit HCV replication has long been hindered by the lack of convenient cell culture models for the propagation of HCV ("Recent Advances in Nucleoside Monophosphate Prodrugs as Anti-hepatitis C Virus Agents" Bobeck, D. R.; Coats, S. J.; Schinazi, R. F. Antivir. Ther. 2010; Book Chapter: "Approaches for the Development of Antiviral Compounds: The Case of Hepatitis C Virus." Raymond F. Schinazi, Steven J. Coats, Leda C. Bassit, Johan Lennerstrand, James H. Nettles, and Selwyn J. Hurwitz in: Handbook of Experimental Pharmacology, vol. 189, 25-51: Antiviral Strategies; Edited by: Hans-Georg Krausslich and Ralf Bartenschlager © Springer-Verlag Berlin Heidelberg 2009). This hurdle has been overcome first with the establishment of the HCV replicon system in 1999 (Bartenschlager, R., Nat. Rev. Drug Discov. 2002, 1, 911-916 and Bartenschlager, R., J. Hepatol. 2005, 43, 210-216) and, in 2005, with the development of robust HCV cell culture models (Wakita, T., et al., Nat. Med. 2005, 11, 791-6; Zhong, J., et al., Proc. Natl. Acad. Sci. U.S.A. 2005, 102, 9294-9; Lindenbach, B. D., et al., Science 2005, 309, 623-6).

Despite the availability of a vaccine (Crit. Rev. Clin. Lab. Sci. 2004, 41, 391-427). Yellow fever virus (YFV) continues to be a serious human health concern, causing approximately 30,000 deaths each year. YFV is one of the most lethal viral infections of humans (Expert Rev. Vaccines 2005, 4, 553-574.). Of infected individuals approximately 15% will develop severe disease, with a fatality rate of 20 to 50% among those individuals. No approved therapies specific for treatment of YFV are available. Treatment is symptomatic-rest, fluids, and ibuprofen, naproxen, acetaminophen, or paracetamol may relieve symptoms of fever and aching. Aspirin should be avoided. Although the virus is endemic to Africa and South America, there is potential for outbreaks of YFV outside these areas and such imported cases have been reported (J. Travel Med. 2005, 12(Suppl. 1), S3-S11).

West Nile Virus (WNV) is from the family Flaviviridae and predominantly a mosquito-borne disease. It was first discovered in the West Nile District of Uganda in 1937. According to the reports from the Centers for Disease Control and Prevention, WNV has been found in Africa, the Middle East, Europe, Oceania, west and central Asia, and North America. Its first emergence in North America began in the New York City metropolitan area in 1999. It is a seasonal epidemic in North America that normally erupts in the summer and continues into the fall, presenting a threat to environmental health. Its natural cycle is bird-mosquito-bird and mammal. Mosquitoes, in particular the species Culex pipiens, become infected when they feed on infected birds. Infected mosquitoes then spread WNV to other birds and mammals including humans when they bite. In humans and horses, fatal Encephalitis is the most serious manifestation of WNV infection. WNV can also cause mortality in some infected birds. There is no specific treatment for WNV infection. In cases with milder symptoms, people experience symptoms such as fever and aches that pass on their own, although even healthy people have become sick for several weeks. In more severe cases, people usually need to go to the hospital where they can receive supportive treatment.

Dengue infection is also from the family Flaviviridae and is the most important arthropod-borne infection in Singapore (Epidemiol News Bull 2006, 32, 62-6). Globally, there are an estimated 50 to 100 million cases of dengue fever (DF) and several hundred thousand cases of dengue hemorrhagic fever (DHF) per year with and average fatality fate of 5%. Many patients recover from dengue infection with minimal or no residual illness. Dengue infections are usually asymptomatic, but can present with classic dengue fever, dengue hemorrhagic fever or dengue shock syndrome. Even for outpatients, the need for maintaining adequate hydration is highly important. Dengue infections can be effectively managed by intravenous fluid replacement therapy, and if diagnosed early, fatality rates can be kept below 1%. To manage the pain and fever, patients suspected of having a dengue infection should be given acetaminophen preparations. Aspirin and non-steroidal anti-inflammatory medications may aggravate the bleeding tendency associated with some dengue infection. However, some manifestations of dengue infection previously described include liver failure (*Dig Dis Sci* 2005, 50, 1146-7), encephalopathy (*J Trop Med Public Health* 1987, 18, 398-406), and Guillain-Barré syndrome (*Intern Med* 2006. 45, 563-4).

Proliferative disorders are one of the major life-threatening diseases and have been intensively investigated for decades. Cancer now is the second leading cause of death in the United States, and over 500,000 people die annually from this proliferative disorder. A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is not fully understood on the molecular level. It is known that exposure of a cell to a carcinogen such as certain viruses, certain chemicals, or radiation, leads to DNA alteration that inactivates a "suppressive" gene or activates an "oncogene." Suppressive genes are growth regulatory genes, which upon mutation, can no longer control cell growth. Oncogenes are initially normal genes (called prooncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three means of therapies: surgery, radiation and chemotherapy. Surgery involves the bulk removal of diseased tissue. While surgery is sometimes effective in removing tumors located at certain sites, for example, in the breast, colon and skin, it cannot be used in the treatment of tumors located in other areas, such as the backbone, or in the treatment of disseminated neoplastic conditions such as leukemia.

Chemotherapy involves the disruption of cell replication or cell metabolism. It is used most often in the treatment of leukemia, as well as breast, lung, and testicular cancer. There are five major classes of chemotherapeutic agents currently in use for the treatment of cancer: natural products and their derivatives; anthacyclines; alkylating agents; antiproliferatives (also called antimetabolites); and hormonal agents. Chemotherapeutic agents are often referred to as antineoplastic agents.

Several synthetic nucleosides, such as 5-fluorouracil, have been identified that exhibit anticancer activity. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation and edema.

It would be advantageous to provide new antiviral and anticancer agents, compositions including these agents, and methods of treatment using these agents, particularly to treat flaviviruses, respiratory syncytial virus (RSV), influenza and cancer, and prevent the emergence of drug resistant flaviviruses, respiratory syncytial virus (RSV), influenza and cancer. The present invention provides such agents, compositions and methods.

SUMMARY OF THE INVENTION

The present invention provides compounds, methods and compositions for treating or preventing HCV infection in a host. The methods involve administering a therapeutically or prophylactically-effective amount of at least one compound as described herein to treat or prevent an infection by, or an amount sufficient to reduce the biological activity of HCV infection.

The present invention also provides compounds, methods and compositions for treating or preventing hepatitis E virus (HEV) infection in a host. The methods involve administering a therapeutically or prophylactically-effective amount of at least one compound as described herein to treat or prevent an infection by, or an amount sufficient to reduce the biological activity of HEV infection.

The pharmaceutical compositions include one or more of the compounds described herein, in combination with a pharmaceutically acceptable carrier or excipient, for treating a host infected with HCV. These compounds can be used in combination with nucleoside and non-nucleoside inhibitors of HCV. The formulations can further include at least one other therapeutic agent. In addition, the present invention includes processes for preparing such compounds.

In some embodiments, the compounds described herein are deuterated at one or more positions, which deuteration can be present in the sugar portion of the compounds, the base portion of the compounds, and/or the prodrug portion of the compounds, at any position other than the 2'-position.

In one embodiment, the active compounds are compounds of Formula (A) or (B):

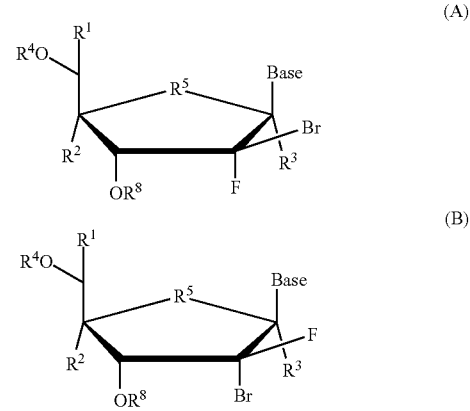

or a pharmaceutically acceptable salt or prodrug thereof, wherein:

$R^1$ is H or Me, wherein, when $R^1$ is Me it may be wholly or partially R or S or any mixture thereof;

$R^2$ is H, $N_3$, F, $(C_{1-8})$alkyl, $(C_{2-8})$alkenyl or $(C_{2-8})$alkynyl;

$R^4$ is H or $P(O)R^6R^7$, wherein, when chirality exists at the phosphorous center of $R^4$, it may be wholly or partially $R_p$ or $S_p$ or any mixture thereof, $R^5$ is O, $CH_2$, S, Se, CHF, $CF_2$, or $C=CH_2$, $R^3$ is H or CN when $R^5$ is O, and $R^3$ is selected from the group consisting of H, CN, $(C_{1-8})$alkyl, $(C_{2-8})$alkenyl, $(C_{2-8})$alkynyl and $O-(C_{1-8})$alkyl when $R^5$ is $CH_2$, CHF, $CF_2$, or $C=CH_2$, $R^8$ is selected from the group consisting of H, $C(O)(C_{1-8})$alkyl, $C(O)(C_{1-8})$branched alkyl, $C(O)NH(C_{1-8})$alkyl, $C(O)NH(C_{1-8})$branched alkyl, $C(O)$aryl $C(O)(C_{1-8})$alkyl-aryl, $C(O)NH(C_{1-8})$alkyl-aryl $C(O)O(C_{1-8})$alkyl, $C(O)O(C_{1-8})$branched alkyl, $C(O)O(C_{1-8})$alkyl-aryl or $OR^8$ as it appears in Formulas A or B is an ester derived from an alpha amino acid, $R^6$ and $R^7$ are independently selected from the group consisting of:

(a) $OR^{15}$ where $R^{15}$ selected from the group consisting of H,

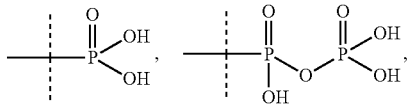

Li, Na, K, $C_{1-20}$alkyl, $C_{3-6}$cycloalkyl, $C_{1-4}$(alkyl)aryl, benzyl, $C_{1-6}$haloalkyl, $C_{2-3}$(alkyl)$OC_{1-20}$alkyl,

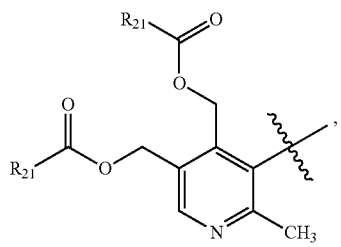

aryl, and heteroaryl, wherein aryl includes phenyl and heteroaryl includes pyridinyl, and wherein phenyl and pyridinyl are optionally substituted with zero to three substituents independently selected from the group consisting of $(CH_2)_{0-6}CO_2R^{16}$ and $(CH_2)_{0-6}CON(R^{16})_2$;

$R^{16}$ is independently H, $C_{1-20}$ alkyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(b)

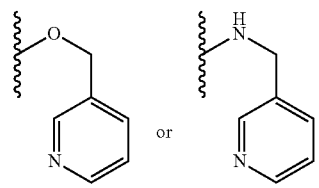

(c) the ester of a D- or L-amino acid

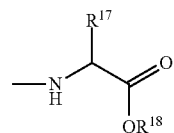

where $R^{17}$ is restricted to those occurring in natural L-amino acids, and $R^{18}$ is H, $C_{1-20}$ alkyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(d) $R^6$ and $R^7$ can come together to form a ring

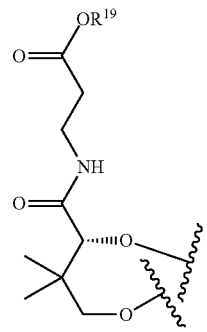

where $R^{19}$ is H, $C_{1-20}$ alkyl, $C_{1-20}$ alkenyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(e) $R^6$ and $R^7$ can come together to form a ring selected from the group consisting of

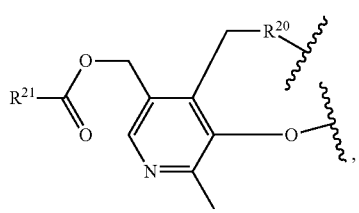

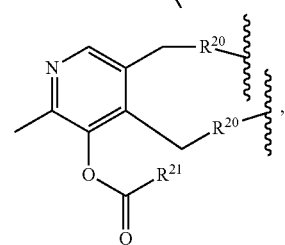

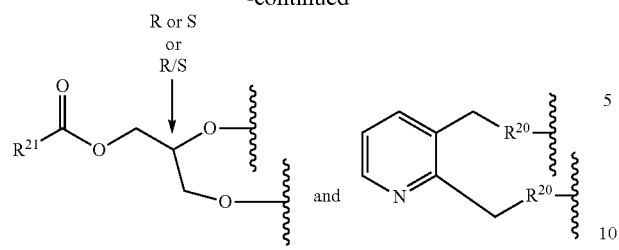

where $R^{20}$ is O or NH, and $R^{21}$ is selected from the group consisting of H, $C_{1-20}$ alkyl, $C_{1-20}$ alkenyl, the carbon chain derived from a fatty acid, and $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl, Base is selected from the group consisting of:

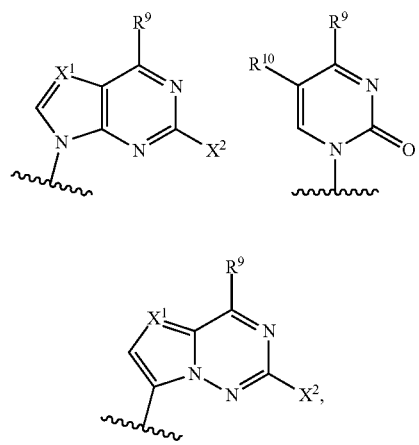

$X^1$ is CH, C—($C_{1-6}$)alkyl, C—($C_{2-6}$)alkenyl, C—($C_{2-6}$) alkynyl, C—($C_{3-7}$)cycloalkyl, C—($C_{1-6}$) haloalkyl, C—($C_{1-6}$)hydroxyalkyl, C—$OR^{22}$, C—$N(R^{22})_2$ C-halo, C—CN or N, $R^{22}$ is independently H, ($C_{1-10}$)alkyl, ($C_{1-10}$)haloalkyl or ($C_{3-7}$)cycloalkyl, $R^9$ is OH, $NH_2$, $O(C_{1-10})$alkyl, $O(C_{3-7})$cycloalkyl, NH ($C_{1-10}$)alkyl, N(($C_{1-10}$)alkyl), NH($C_{3-7}$)cycloalkyl, NH(CO) ($C_{1-20}$)alkyl, NH(CO)O($C_{1-20}$)alkyl, NHOH, NHO(CO) ($C_{1-20}$)alkyl, NHO(CO)NH($C_{1-20}$)alkyl, $R^{10}$ is H, F or $CH_3$ and $X^2$ is H, F, Cl ($C_{1-6}$)alkyl, ($C_{2-6}$)alkenyl, ($C_{2-6}$)alkynyl, C—($C_{3-7}$)cycloalkyl, C—($C_{1-6}$) haloalkyl, ($C_{1-6}$)haloalkyl, ($C_{3-7}$)cycloalkyl, ($C_{1-6}$)hydroxyalkyl, $OR^{22}$, $SR^{22}$, $N(R^{22})_2$, $NHC(O)OR^{22}$, $NHC(O)N(R^{22})_2$, $NHC(O)R^{22}$, CN or $NH_2$.

These compounds can be present in the β-D or β-L configuration, although the β-D is the preferred embodiment.

A subset of the compounds of Formula (A) or Formula (B) is provided below:

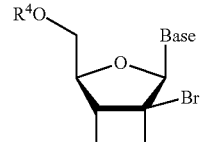

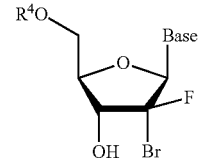

where $R^4$ and Base are as defined above.

These compounds can also be in the β-D or β-L configuration.

Representative compounds of these formulas are shown below:

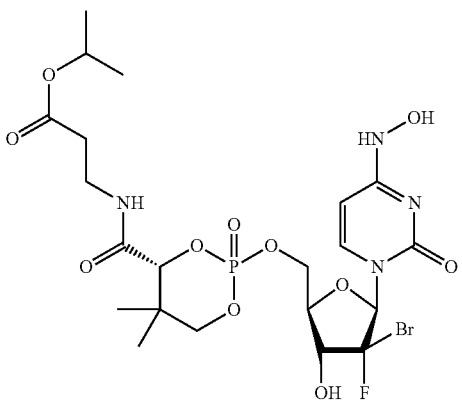

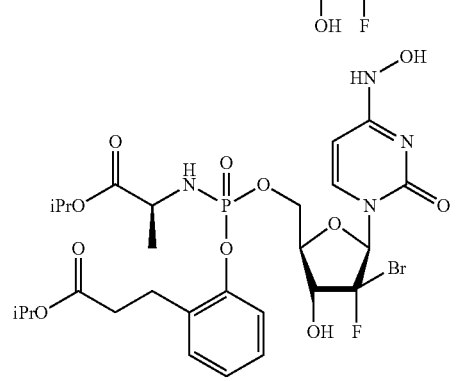

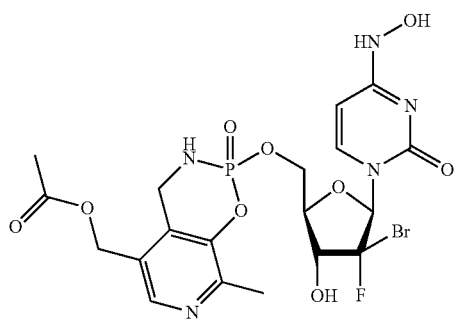

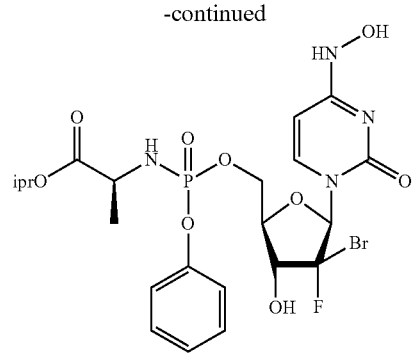
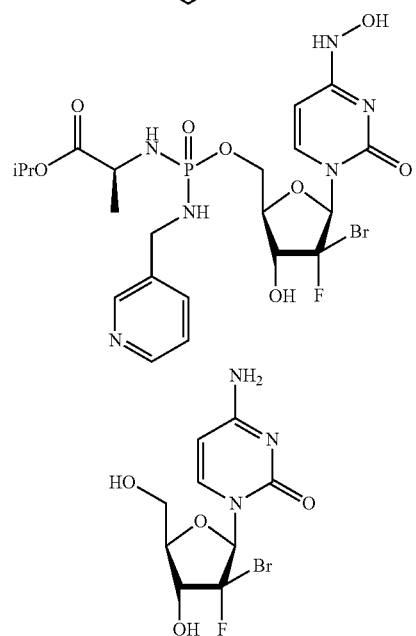
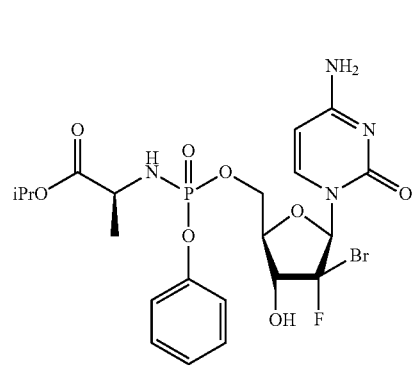
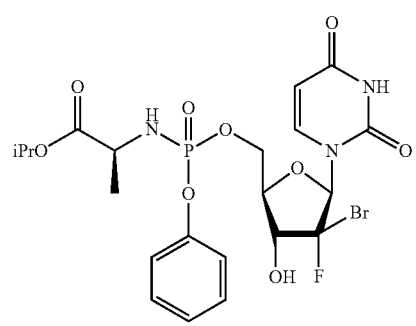
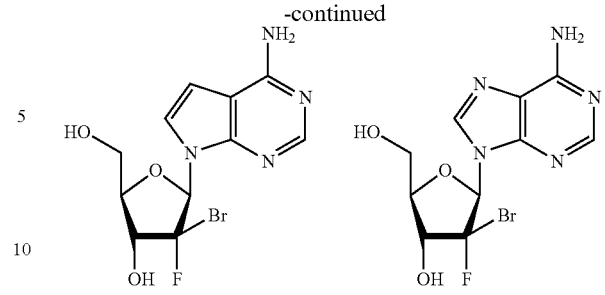
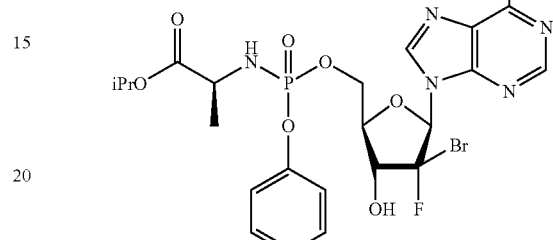
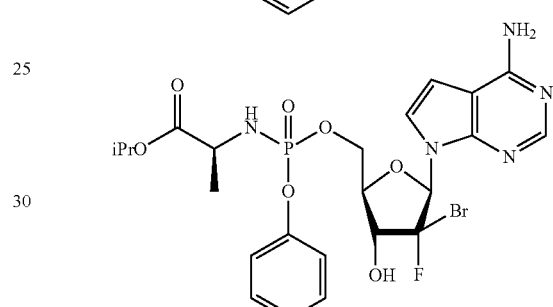
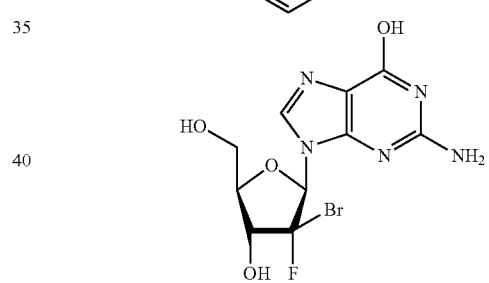
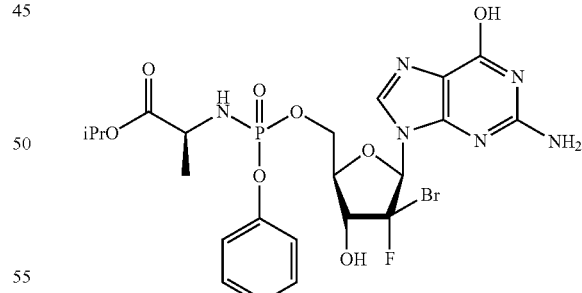
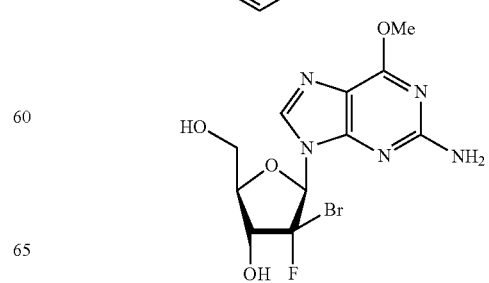

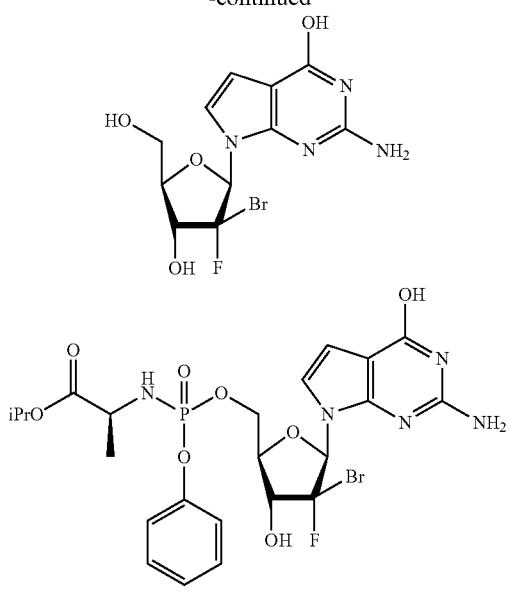
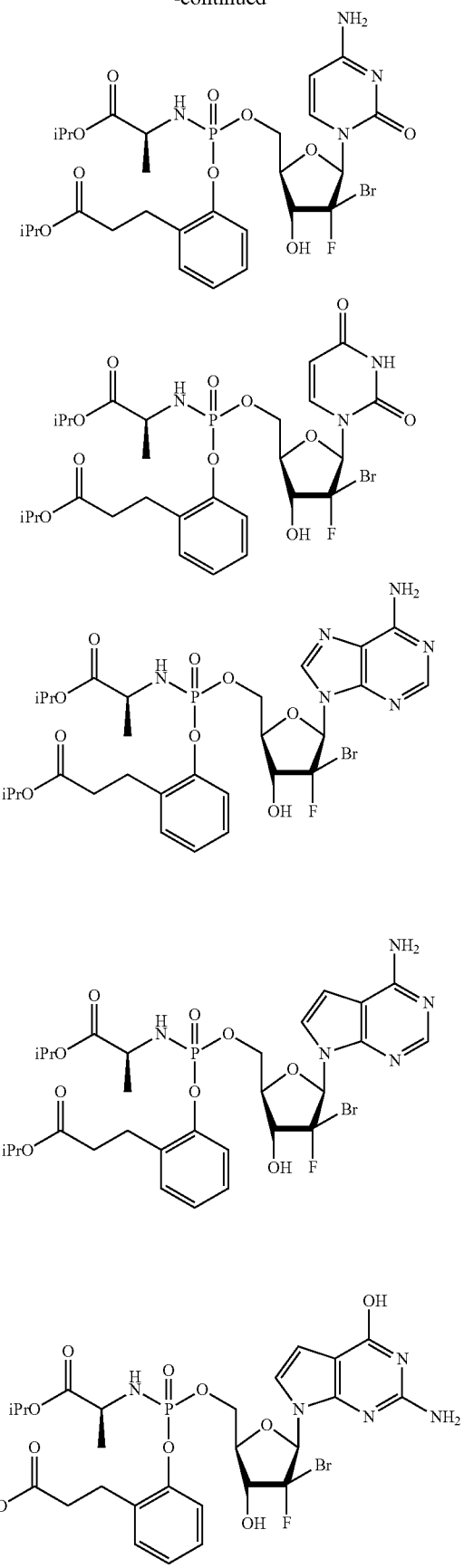

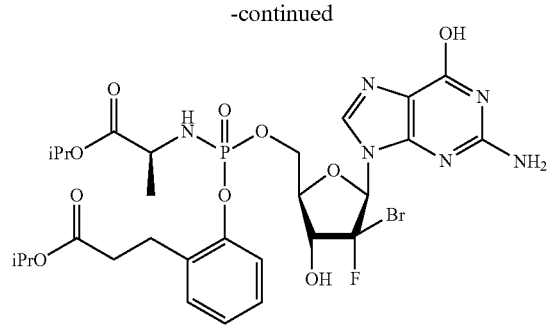
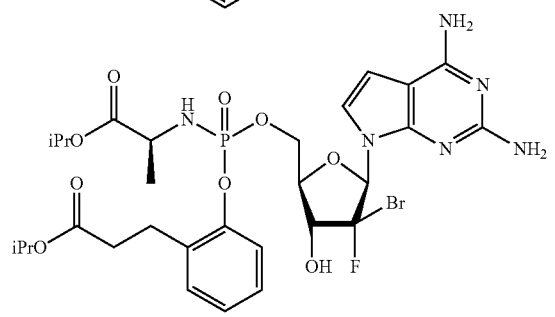
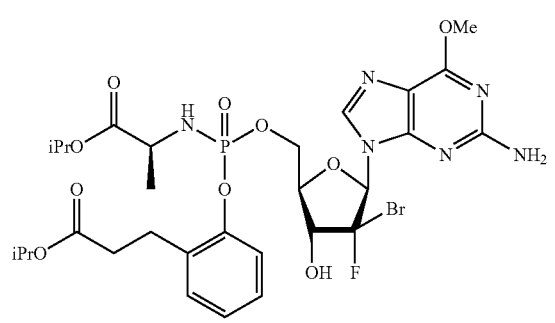
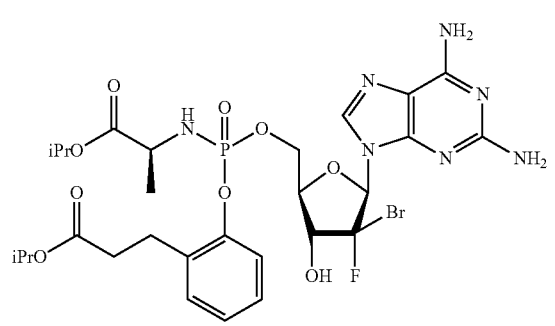
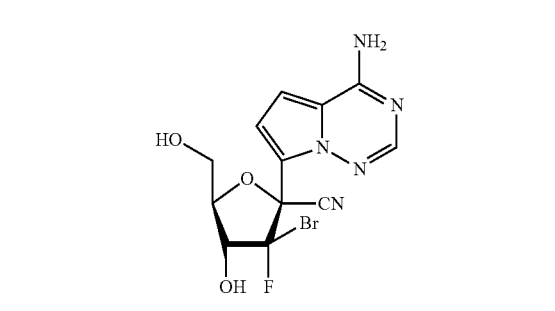
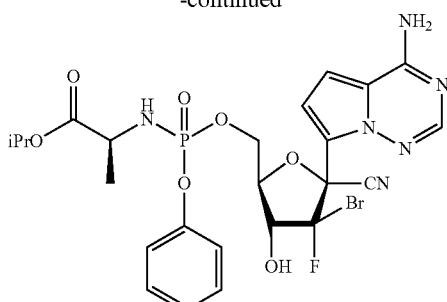
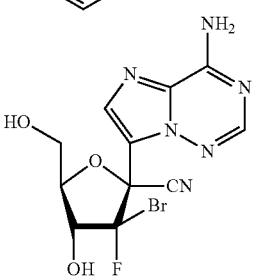
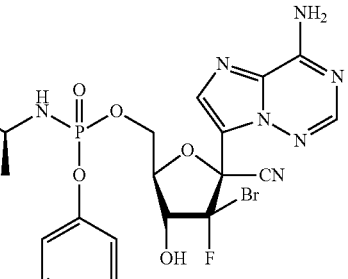
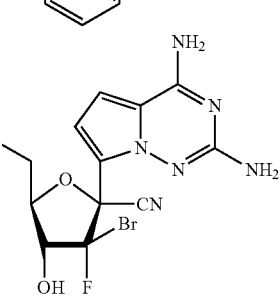
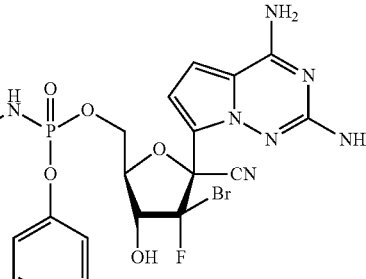
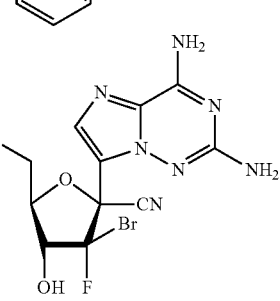

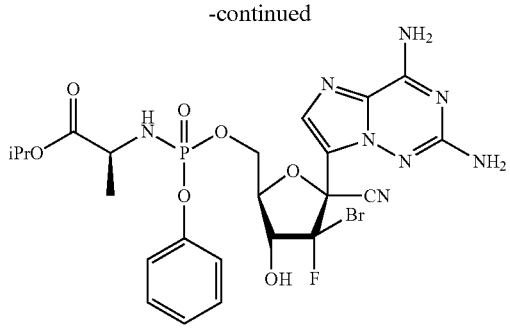
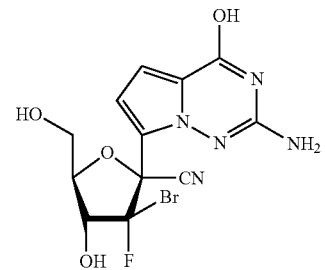
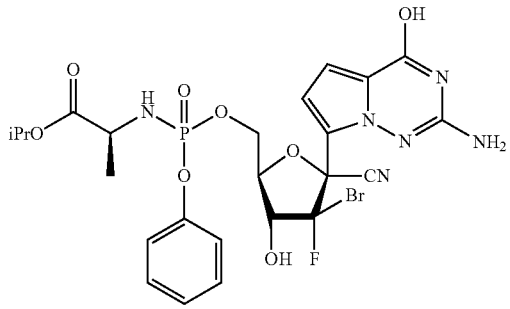
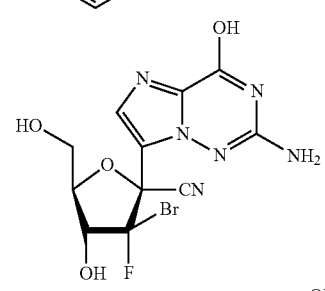
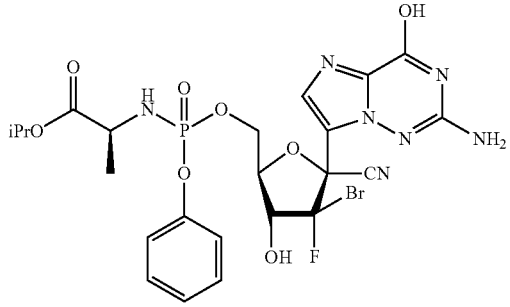
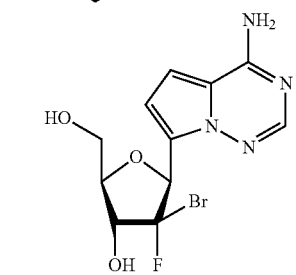
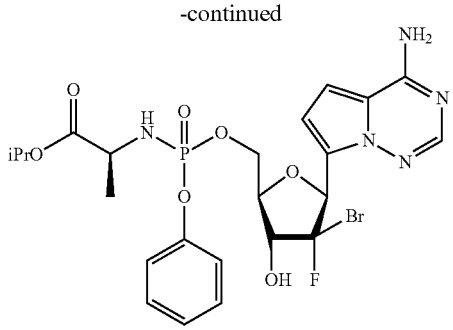
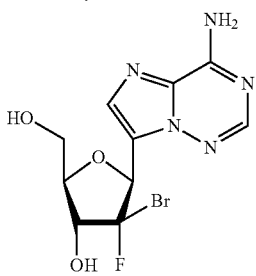
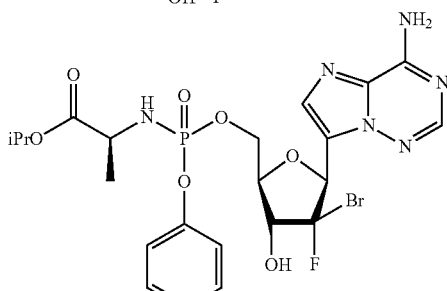
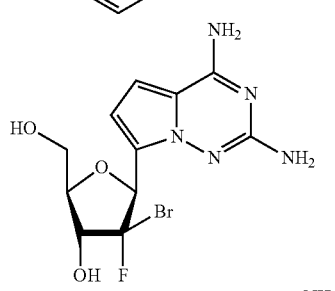
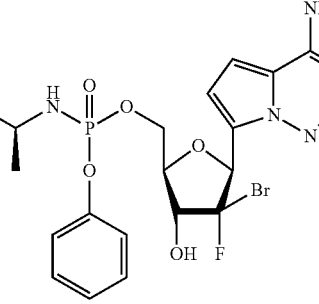
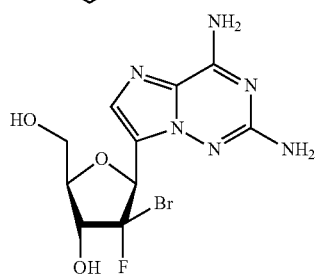

17
-continued
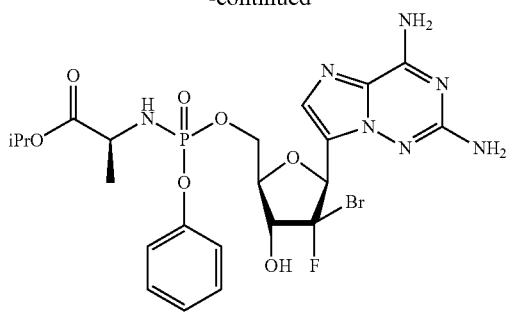
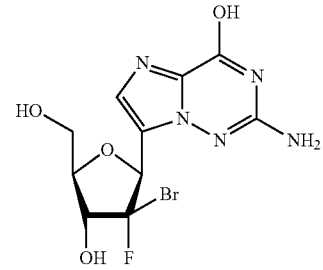
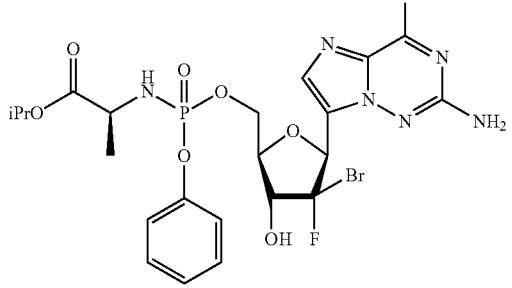
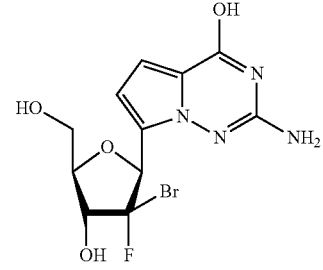
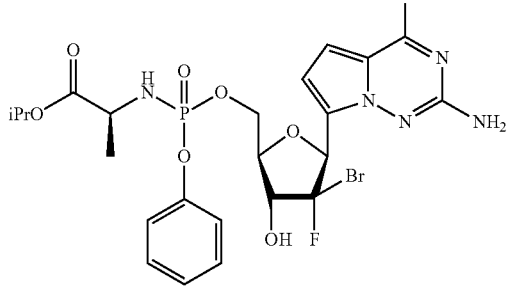
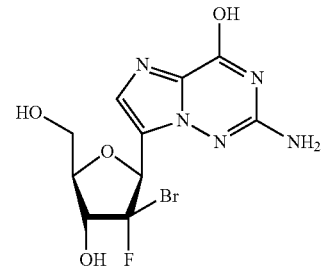
18
-continued
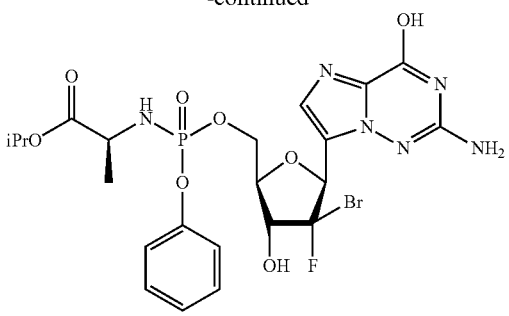
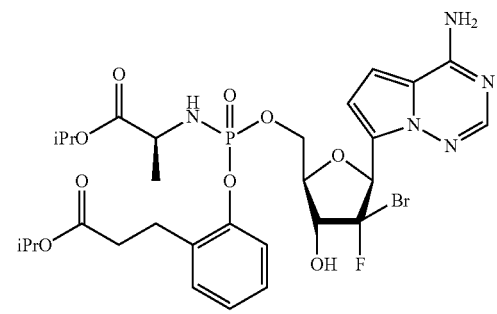
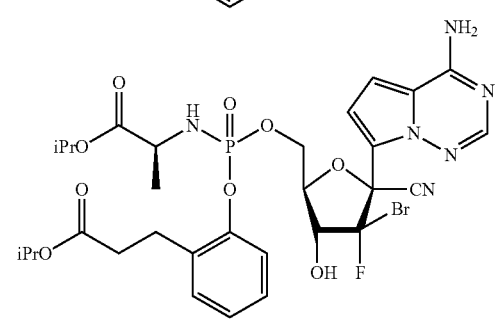
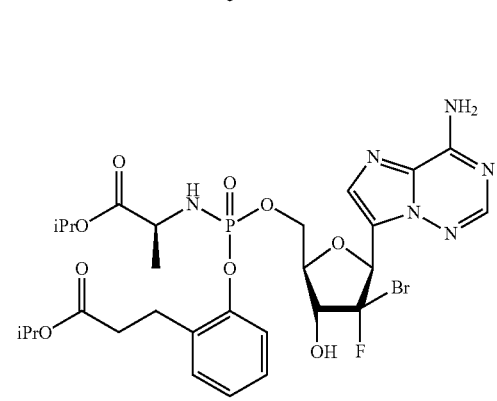
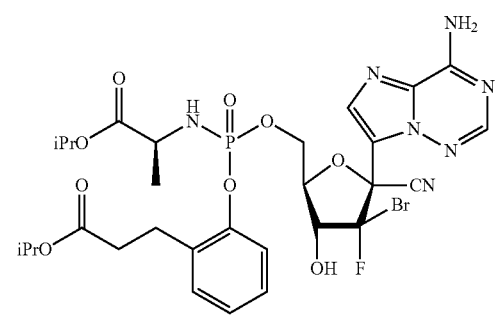

-continued
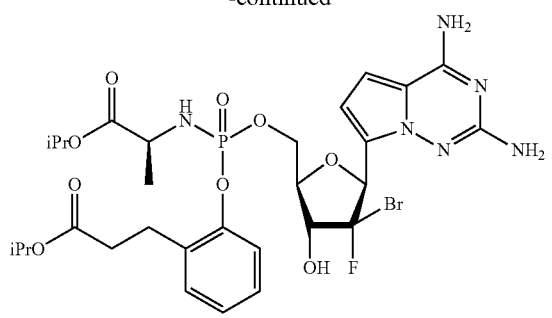
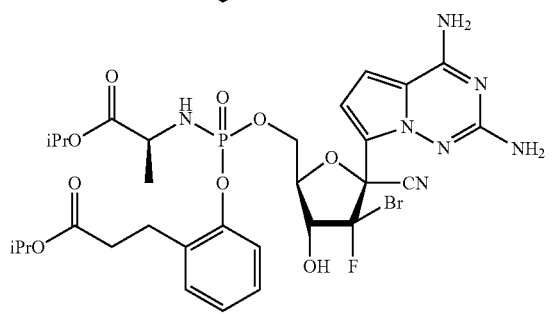
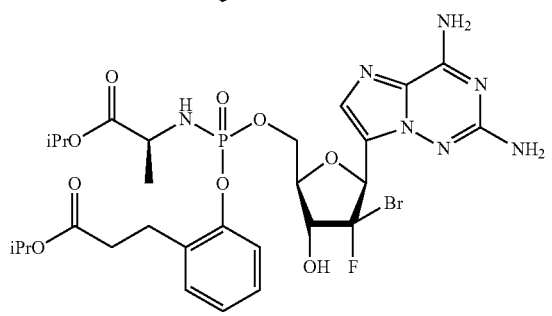
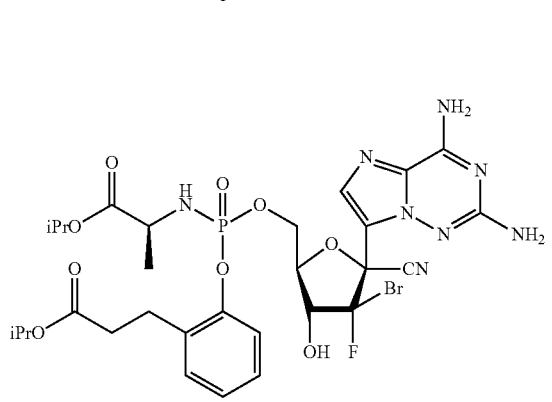
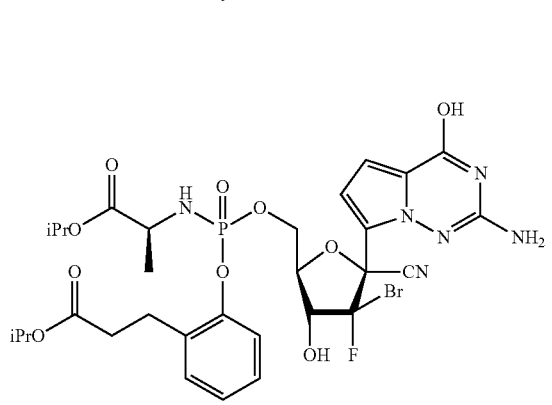
-continued
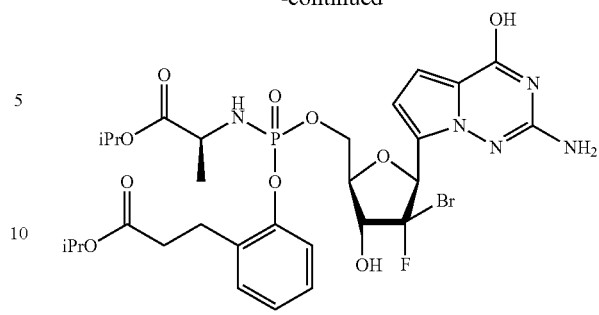
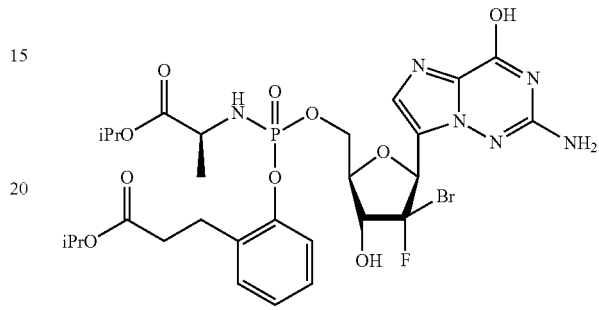
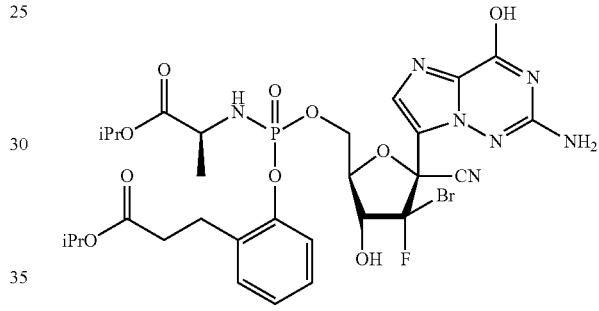
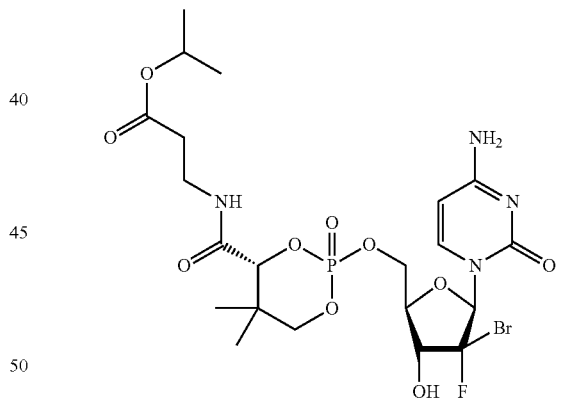
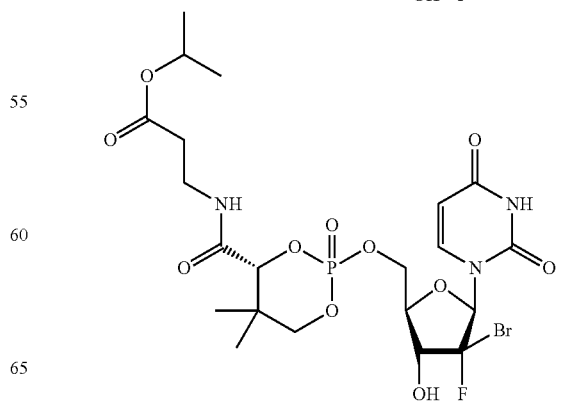

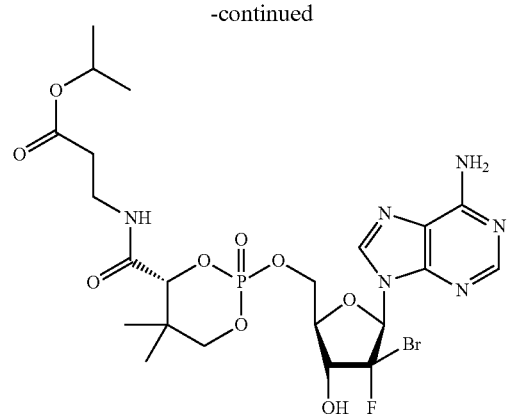
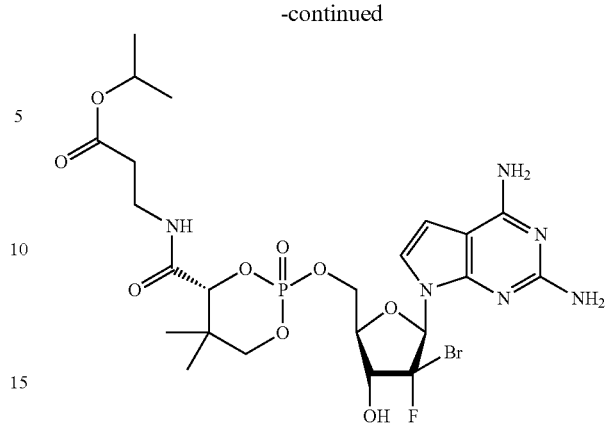
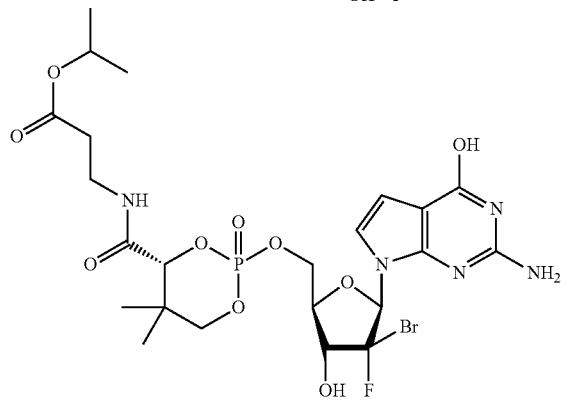
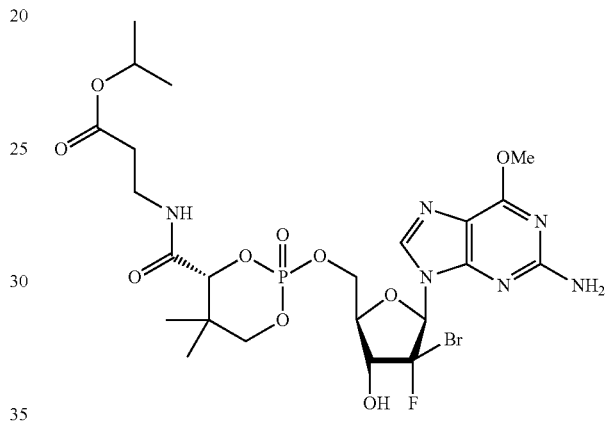
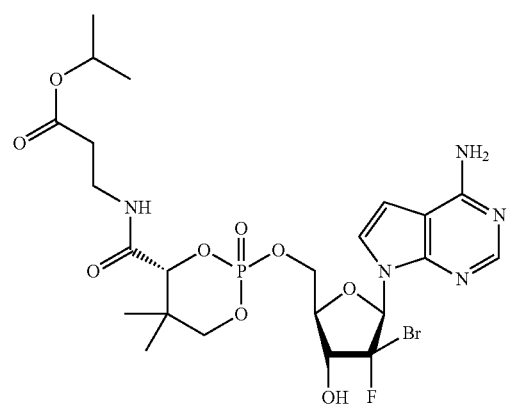
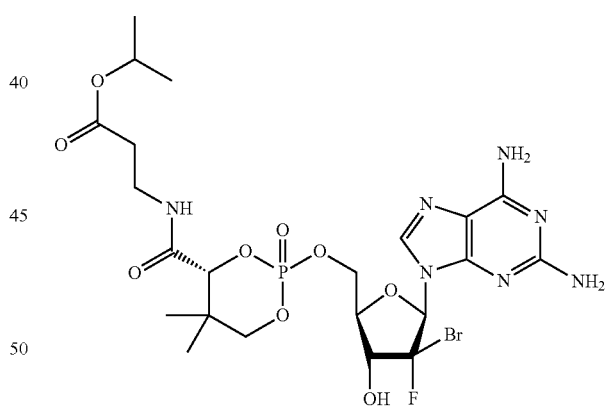
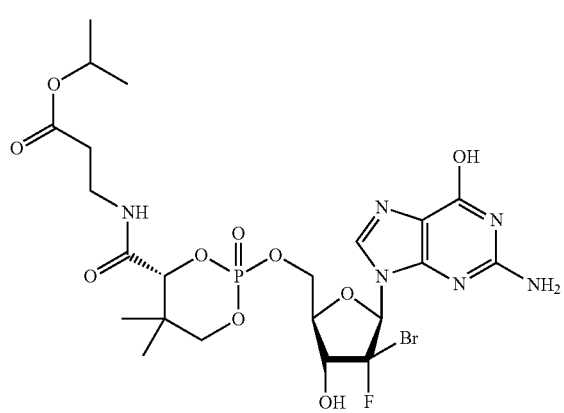
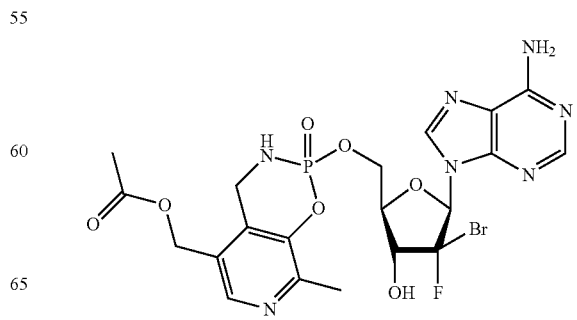

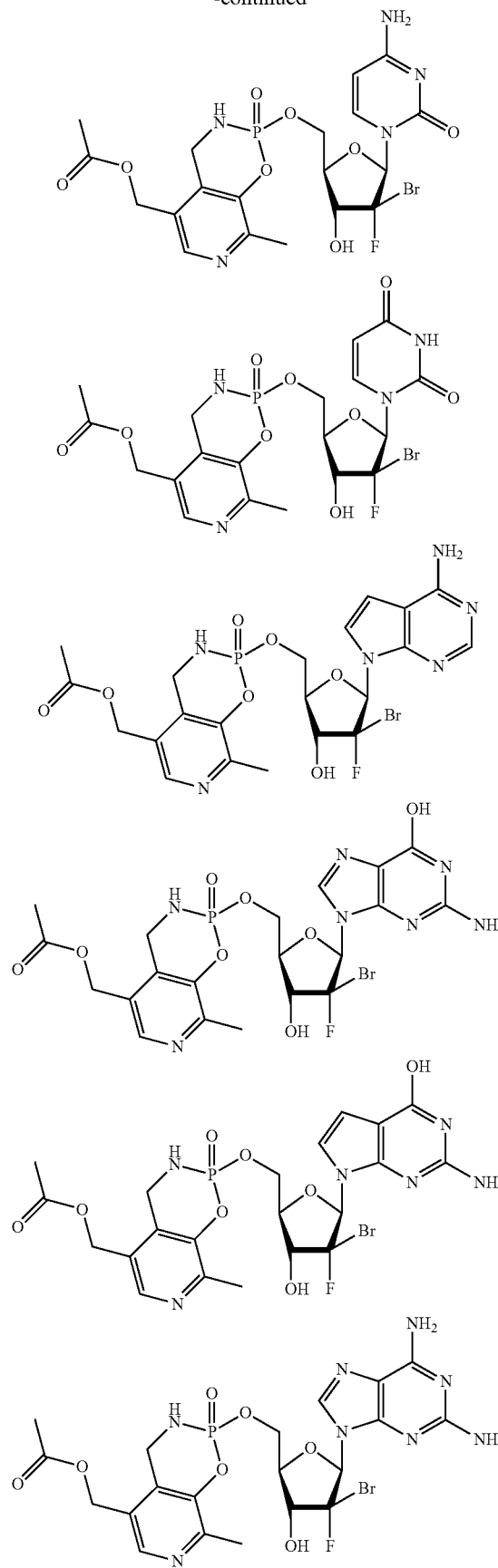
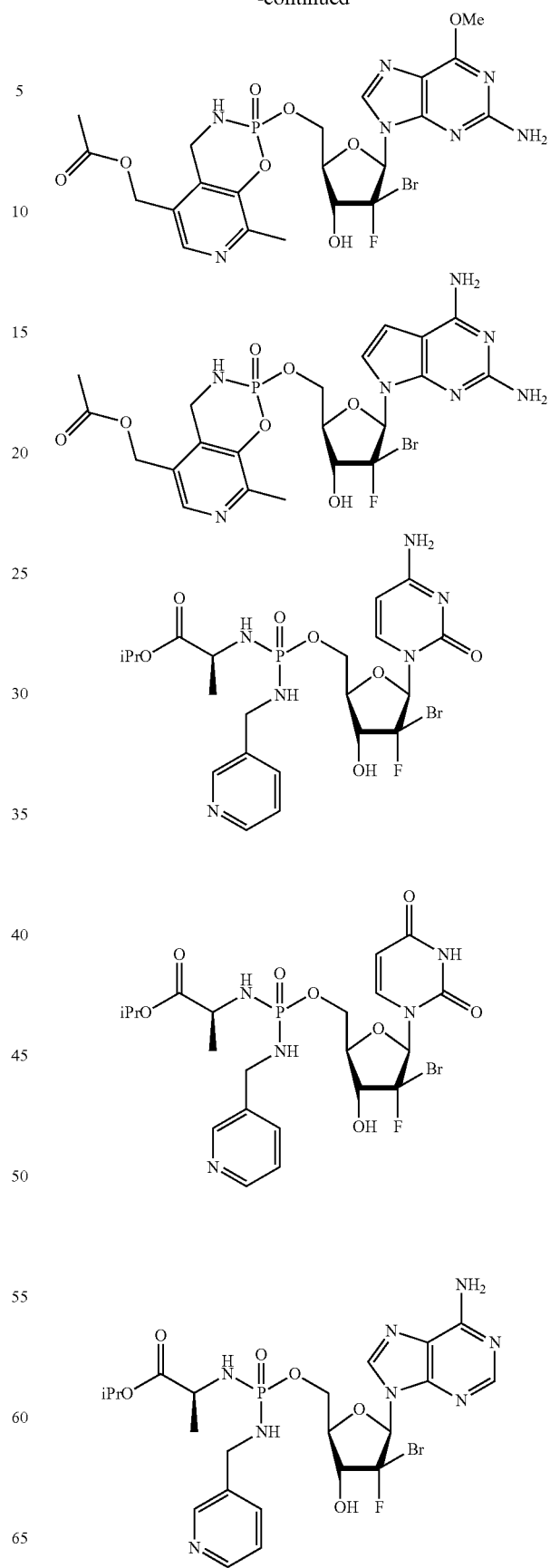

-continued
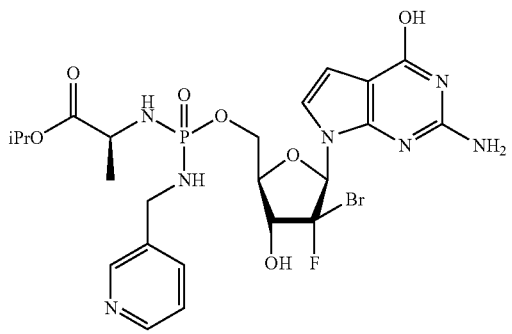
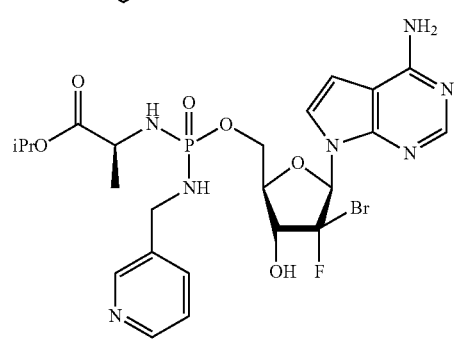
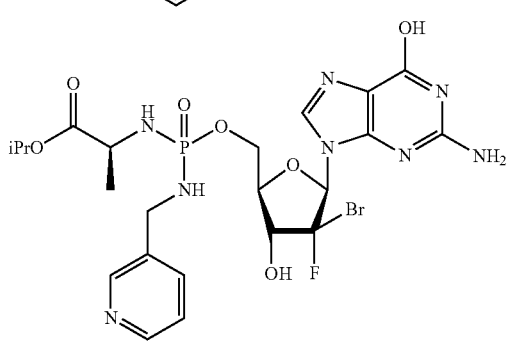
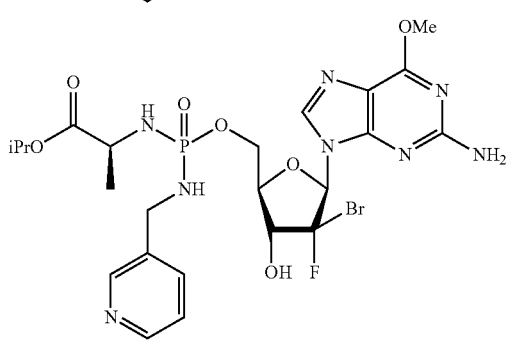
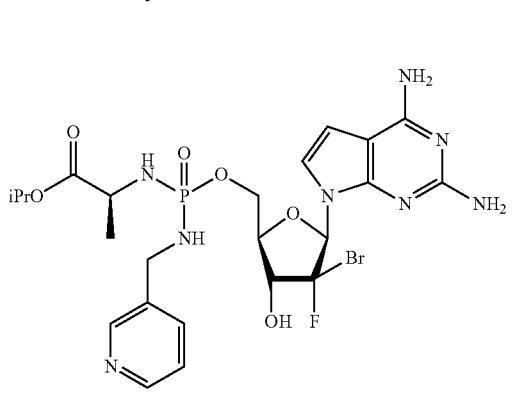
-continued
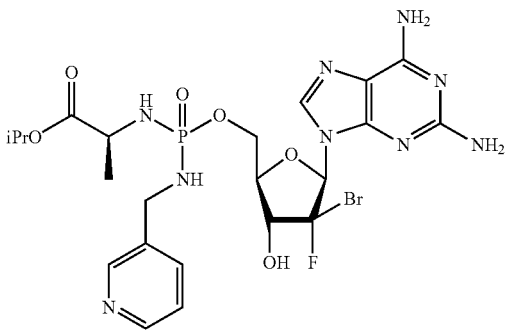
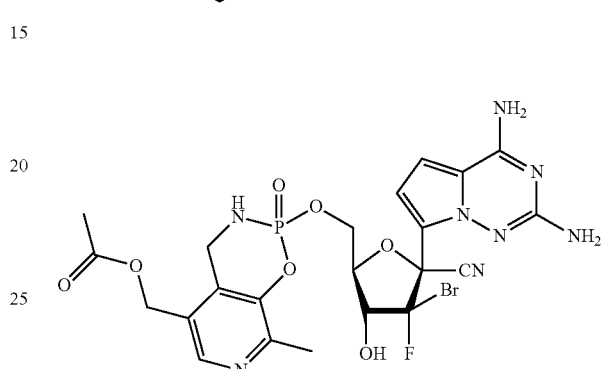
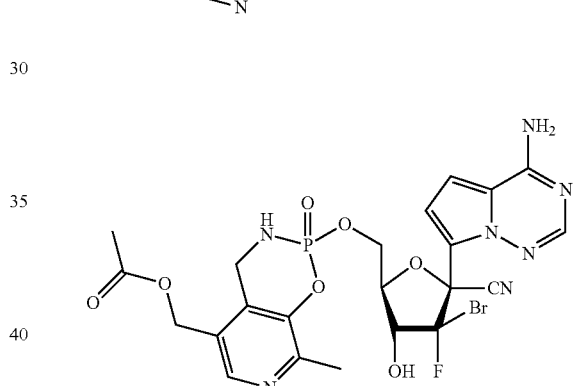
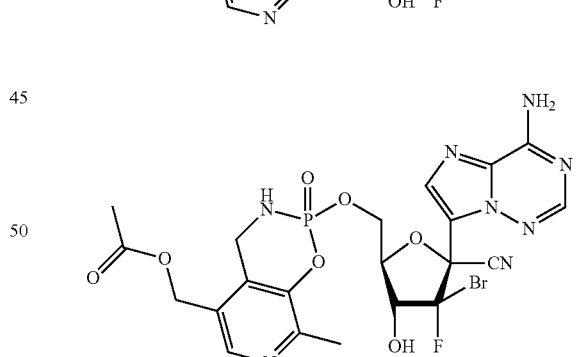
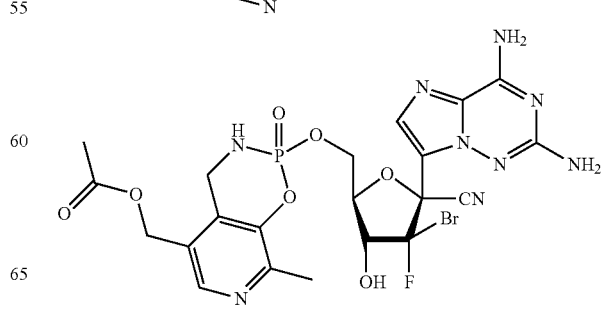

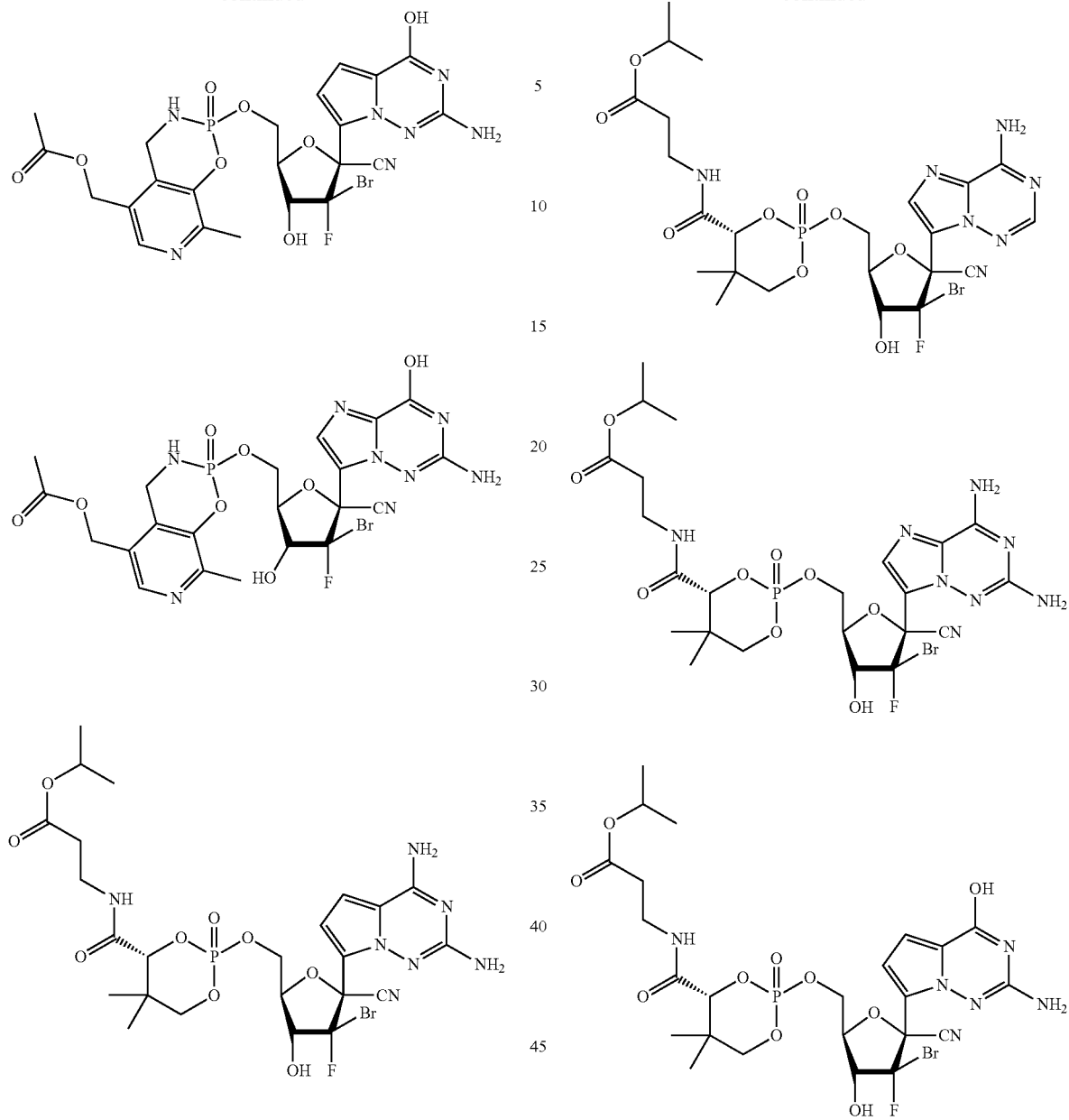
or pharmaceutically acceptable salts thereof.

A particularly preferred compound has the formula:

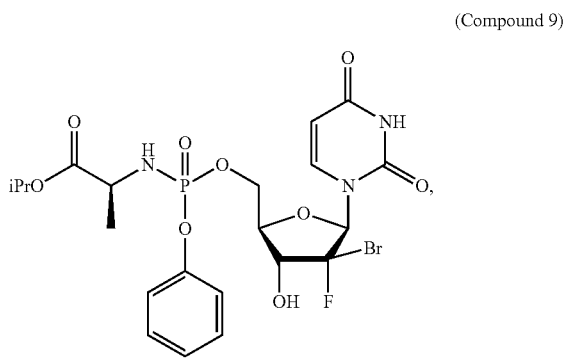

(Compound 9)

or a pharmaceutically acceptable salt thereof.

Another particularly preferred compound is Compound 7, the 5'-OH analog of Compound 9. This compound is a preferred compound, as it is an intermediate used to prepare Compound 9 and other compounds with different prodrug moieties at the 5'-position.

The compounds can be used in combination therapy, for example, using conventional ribavirin/Pegasys therapy or with other nucleoside anti-HCV agents or NS4A inhibitors or NS5A inhibitors. Representative anti-HCV agents for use in combination therapy include, but are not limited to, a combination of Pegylated interferon (Pegasys) and ribavirin, polymerase inhibitors such as IDX-375 and IDX-184 (Idenix), PSI-7851 and Sofosbuvir (also known as Sovaldi, sold by Pharmasset/Gilead), danoprevir (InterMune/Genentech), RG7128 (Pharmasset/Genentech), I ANA598 (Anadys Pharmaceuticals), TMN-191 (R7227), combinations of RG7128 and RG7227 (Genentech, Pharmasset and Intermune), ABT-072 (Abbott), VX-916, VX-759, VX-222, and VX-500 (Vertex), Filibuvir (PF-00868554) (Pfizer), GS 9190 (Gilead), alone or with boosters such as ritonavir, and serine protease inhibitors such as Boceprevir (SCH 503034) (Schering Plough), BILN-2061, Telaprevir (Vertex), ACH-1625 (Achillion), GS-9256 (Gilead), BI 201335 (Boehringer Ingelheim Pharma), Vaniprevir (MK-7009) (Merck), Ledispavir (Gilead), Daclastavir (BMS), GS-5816 (Gilead) SCH900518 (Narlaprevir) (Schering/Merck), TMC435 (Medivir/Tibotec). Additional examples of serine protease inhibitors are provided, for example, in Reiser and Timm, "Serine protease inhibitors as anti-hepatitis C virus agents," Expert Review of Anti-infective Therapy, 7(5):537-547 (June 2009), the contents of which are hereby incorporated by reference. The preferred combinations would be with other pangenotypic nucleosides, protease inhibitors, NS4A inhibitors, NS5A inhibitors, and/or NS5B inhibitors. Representative agents are described, for example, in PCT/US11/49426 PCT/US10/23563, PCT/US12/38165, PCT/US13/67309 and PCT/US11/58404.

The present invention will be better understood with reference to the following detailed description.

BRIEF DESCRIPTION OF THE DRAWINGS

FIGS. 6a and 6b are charts and tables showing cellular egress of Compound 9 (FIG. 6a) and sofosbuvir (FIG. 6b) from Primary Human Hepatocytes. The results are of freshly plated human hepatocytes ($0.35 \times 10^{-6}$) from a 47 year old Caucasian male donor, where the cells were plated in 24-well plates. The compounds were pre-incubated at a concentration of 10 µM for 12 h, and cells were harvested at 0, 1, 2, 4, 10, 24 and 48 hours. The results for the monophosphate are shown in grey, for the diphosphate in orange, and for the triphosphate in blue.

DETAILED DESCRIPTION

Figure 1:
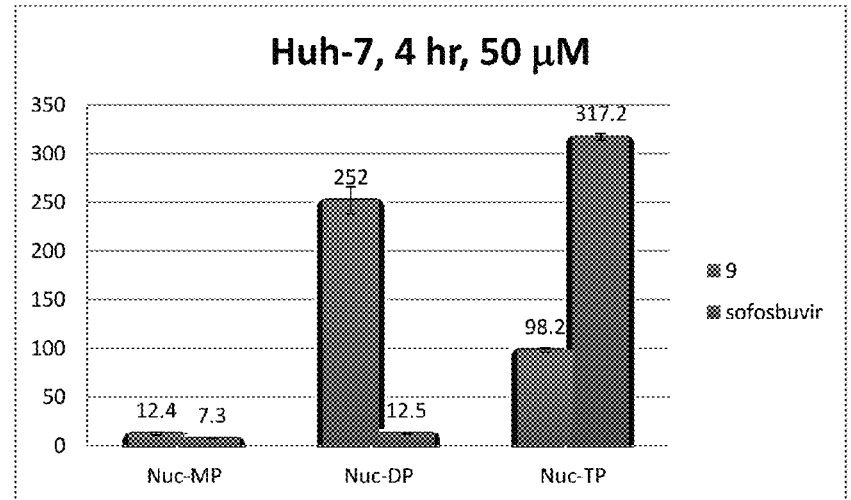
FIG. 1 is a chart showing the triphosphate production from Compound 9, versus Sofosbuvir, in Huh-7 cells.

The compounds described herein show inhibitory activity against HCV in cell-based assays. Therefore, the compounds can be used to treat or prevent a HCV in a host, or reduce the biological activity of the virus. The host can be a mammal, and in particular, a human, infected with HCV. The methods involve administering an effective amount of one or more of the compounds described herein.

The compounds described herein also show inhibitory action against HEV. Therefore, the compounds can be used to treat or prevent a HEV in a host, or reduce the biological activity of the virus. The host can be a mammal, and in particular, a human, infected with HEV. The methods involve administering a therapeutically or prophylactically-effective amount of one or more of the compounds described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a compound composition that comprises at least approximately 95%, and, preferably, approximately 97%, 98%, 99% or 100% of a single enantiomer of that compound.

As used herein, the term "substantially free of" or "substantially in the absence of" refers to a compound composition that includes at least 85 to 90% by weight, preferably 95% to 98% by weight, and, even more preferably, 99% to 100% by weight, of the designated enantiomer of that compound. In a preferred embodiment, the compounds described herein are substantially free of enantiomers.

Similarly, the term "isolated" refers to a compound composition that includes at least 85 to 90% by weight, preferably 95% to 98% by weight, and, even more preferably, 99% to 100% by weight, of the compound, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$.

In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

As used herein, a "bridged alkyl" refers to a bicyclo- or tricyclo alkane, for example, a 2:1:1 bicyclohexane.

As used herein, a "spiro alkyl" refers to two rings that are attached at a single (quaternary) carbon atom.

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moieties. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "fatty alcohol" as used herein refers to straight-chain primary alcohols with between 4 and 26 carbons in the chain, preferably between 8 and 26 carbons in the chain, and most preferably, between 10 and 22 carbons in the chain. The precise chain length varies with the source. Representative fatty alcohols include lauryl, stearyl, and oleyl alcohols. They are colourless oily liquids (for smaller carbon numbers) or waxy solids, although impure samples may appear yellow. Fatty alcohols usually have an even number of carbon atoms and a single alcohol group (—OH) attached to the terminal carbon. Some are unsaturated and some are branched. They are widely used in industry. As with fatty acids, they are often referred to generically by the number of carbon atoms in the molecule, such as "a C12 alcohol", that is an alcohol having 12 carbons, for example dodecanol.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from the group consisting of straight, branched, or cyclic alkyl or lower alkyl, alkoxyalkyl, including, but not limited to methoxymethyl, aralkyl, including, but not limited to, benzyl, aryloxyalkyl, such as phenoxymethyl, aryl, including, but not limited to, phenyl, optionally substituted with halogen (F, Cl, Br, or I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$ alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituents selected from the group consisting of halogen, haloalkyl, alkyl, alkoxy, hydroxy, carboxyl derivatives, amido, amino, alkylamino, and dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human being. Veterinary applications, in certain indications, however, are clearly contemplated by the present invention (such as for use in treating chimpanzees).

The term "peptide" refers to a natural or synthetic compound containing two to one hundred amino acids linked by the carboxyl group of one amino acid to the amino group of another.

The term "pharmaceutically acceptable salt or prodrug" is used throughout the specification to describe any pharmaceutically acceptable form (such as an ester) compound which, upon administration to a patient, provides the compound. Pharmaceutically-acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

II. Active Compounds

In one embodiment, the active compounds are compounds of Formula (A) or (B):

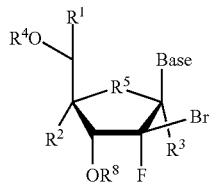
(A)

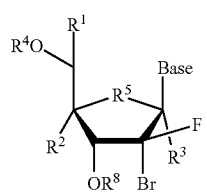
(B)

or a pharmaceutically acceptable salt or prodrug thereof, wherein:

$R^1$ is H or Me, wherein, when $R^1$ is Me it may be wholly or partially R or S or any mixture thereof;

$R^2$ is H, $N_3$, F, $(C_{1-8})$alkyl, $(C_{2-8})$alkenyl or $(C_{2-8})$alkynyl;

$R^4$ is H or $P(O)R^6R^7$, wherein, when chirality exists at the phosphorous center of $R^4$, it may be wholly or partially $R_p$ or $S_p$ or any mixture thereof, $R^5$ is O, $CH_2$, S, Se, CHF, $CF_2$, or $C=CH_2$, $R^3$ is H or CN when $R^5$ is O, and $R^3$ is selected from the group consisting of H, CN, $(C_{1-8})$alkyl, $(C_{2-8})$alkenyl, $(C_{2-8})$alkynyl and O—$(C_{1-8})$alkyl when $R^5$ is $CH_2$, CHF, $CF_2$, or $C=CH_2$, $R^8$ is selected from the group consisting of H, C(O) $(C_{1-8})$alkyl, $C(O)(C_{1-8})$branched alkyl, $C(O)NH(C_{1-8})$alkyl, $C(O)NH(C_{1-8})$branched alkyl, C(O)aryl $C(O)(C_{1-8})$alkyl-aryl, $C(O)NH(C_{1-8})$alkyl-aryl $C(O)O(C_{1-8})$alkyl, $C(O)O(C_{1-8})$branched alkyl, $C(O)O(C_{1-8})$alkyl-aryl or $OR^8$ as it appears in Formulas A or B is an ester derived from an alpha amino acid, $R^6$ and $R^7$ are independently selected from the group consisting of:

(a) $OR^{15}$ where $R^{15}$ selected from the group consisting of H,

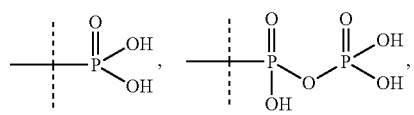

Li, Na, K, $C_{1-20}$alkyl, $C_{3-6}$cycloalkyl, $C_{1-4}$(alkyl)aryl, benzyl, $C_{1-6}$haloalkyl, $C_{2-3}$(alkyl)O$C_{1-20}$alkyl, aryl, and heteroaryl, wherein aryl includes phenyl and heteroaryl includes pyridinyl, and wherein phenyl and pyridinyl are optionally substituted with zero to three substituents independently selected from the group consisting of $(CH_2)_{0-6}CO_2R^{16}$ and $(CH_2)_{0-6} CON(R^{16})_2$;

$R^{16}$ is independently H, $C_{1-20}$ alkyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

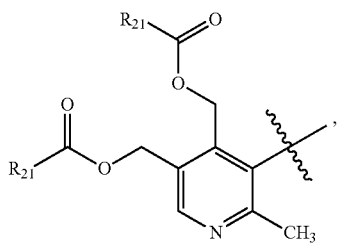

(b)

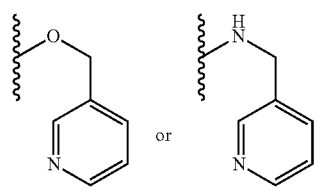

(c) the ester of a D- or L-amino acid

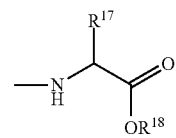

where $R^{17}$ is restricted to those occurring in natural L-amino acids, and $R^{18}$ is H, $C_{1-20}$ alkyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(d) $R^6$ and $R^7$ can come together to form a ring

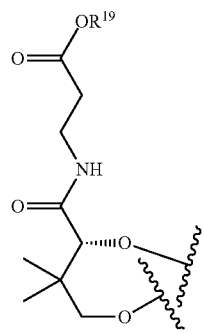

where $R^{19}$ is H, $C_{1-20}$ alkyl, $C_{1-20}$ alkenyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(e) $R^6$ and $R^7$ can come together to form a ring selected from the group consisting of

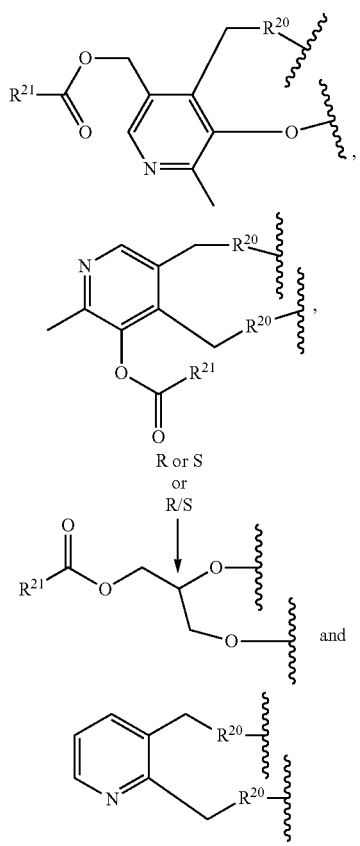

where
$R^{20}$ is O or NH, and
$R^{21}$ is selected from the group consisting of H, $C_{1-20}$ alkyl, $C_{1-20}$ alkenyl, the carbon chain derived from a fatty acid, and $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl, Base is selected from the group consisting of:

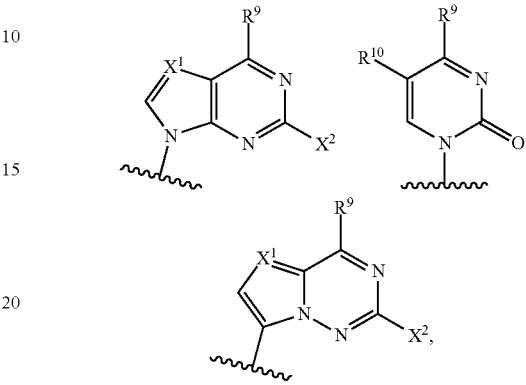

$X^1$ is CH, C—$(C_{1-6})$alkyl, C—$(C_{2-6})$alkenyl, C—$(C_{2-6})$alkynyl, C—$(C_{3-7})$cycloalkyl, C—$(C_{1-6})$ haloalkyl, C—$(C_{1-6})$hydroxyalkyl, C—$OR^{22}$, C—$N(R^{22})_2$ C-halo, C—CN or N, $R^{22}$ is independently H, $(C_{1-10})$alkyl, $(C_{1-10})$haloalkyl or $(C_{3-7})$cycloalkyl, $R^9$ is OH, $NH_2$, $O(C_{1-10})$alkyl, $O(C_{3-7})$cycloalkyl, NH$(C_{1-10})$alkyl, $N((C_{1-10})$alkyl$)_2$, $NH(C_{3-7})$cycloalkyl, NH(CO)$(C_{1-20})$alkyl, NH(CO)O$(C_{1-20})$alkyl, NHOH, NHO(CO)$(C_{1-20})$alkyl, NHO(CO)NH$(C_{1-20})$alkyl, $R^{10}$ is H, F or $CH_3$ and $X^2$ is H, F, Cl $(C_{1-6})$alkyl, $(C_{2-6})$alkenyl, $(C_{2-6})$alkynyl, C—$(C_{3-7})$cycloalkyl, C—$(C_{1-6})$ haloalkyl, $(C_{1-6})$haloalkyl, $(C_{3-7})$cycloalkyl, $(C_{1-6})$hydroxyalkyl, $OR^{22}$, $SR^{22}$, $N(R^{22})_2$, $NHC(O)OR^{22}$, $NHC(O)N(R^{22})_2$, $NHC(O)R^{22}$, CN or $NH_2$.

These compounds can be present in the β-D or β-L configuration, although the β-D is the preferred embodiment.

A subset of the compounds of Formula (A) or Formula (B) is provided below:

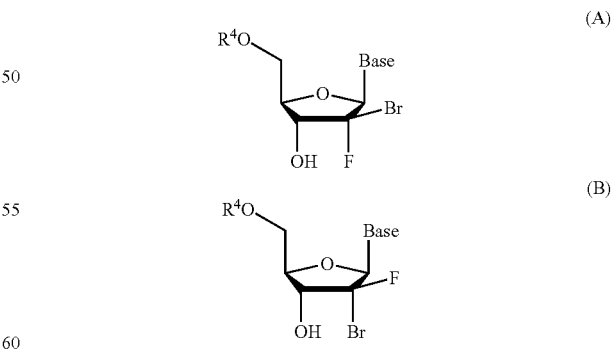

where $R^4$ and Base are as defined above.

These compounds can also be in the β-D or β-L configuration.

In some embodiments, the compounds described herein are deuterated at one or more positions, which deuteration can be present in the sugar portion of the compounds, the base portion of the compounds, and/or the prodrug portion of the compounds, at any position other than the 2'-position.
Representative compounds of these formulas are shown below:
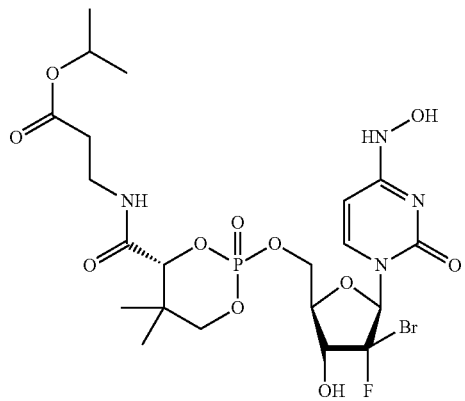
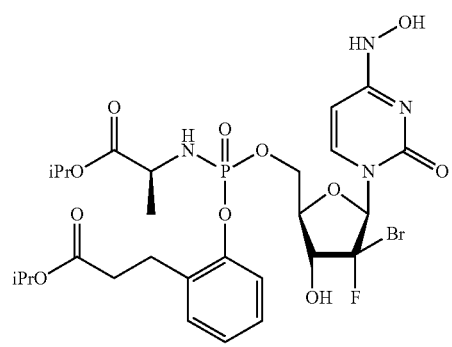
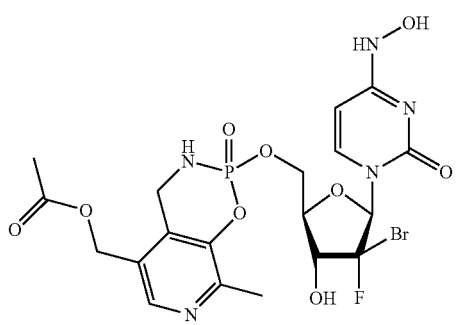
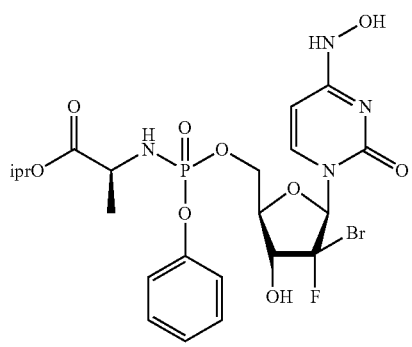
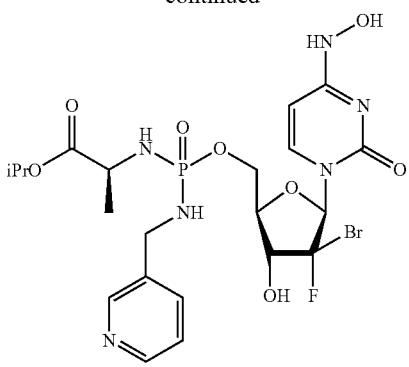
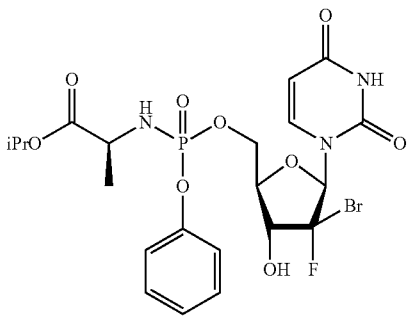
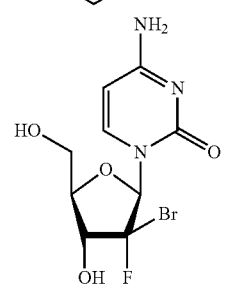
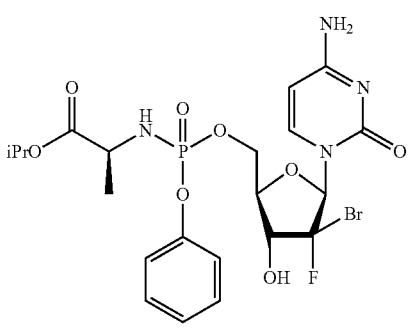
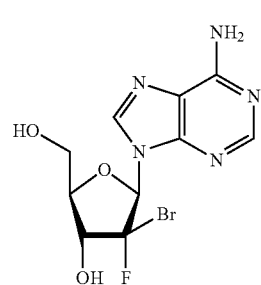

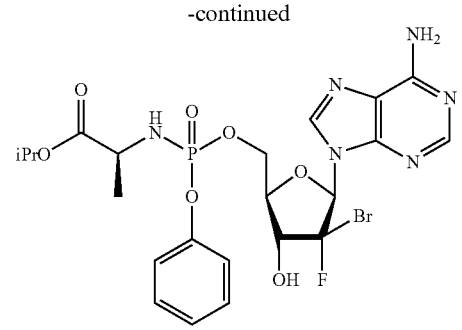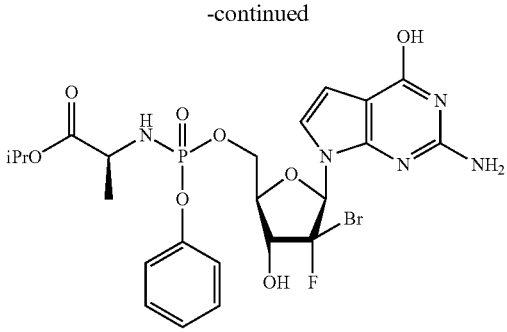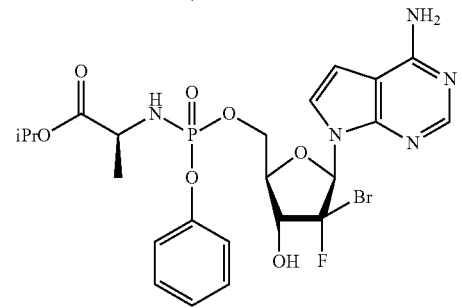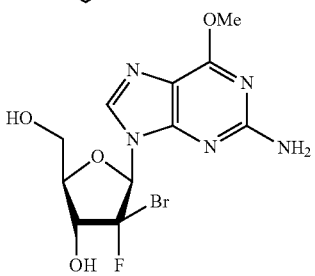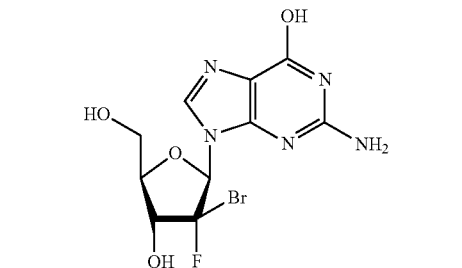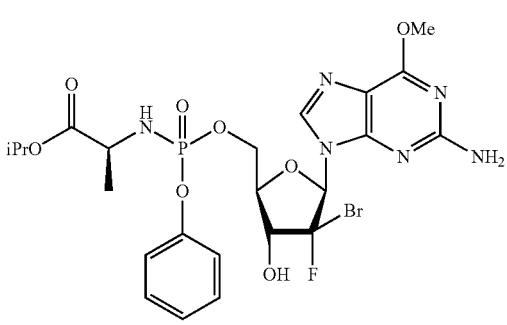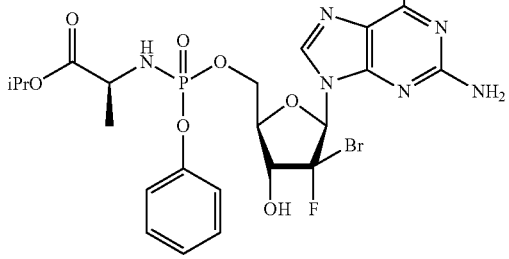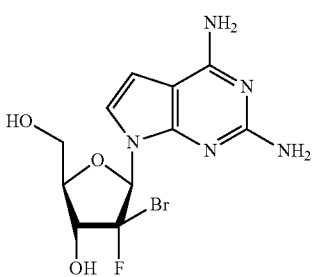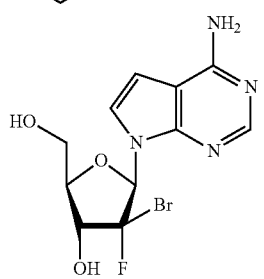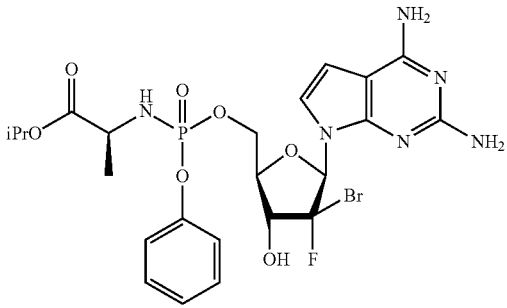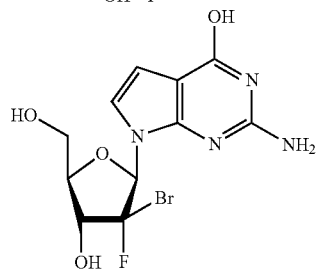

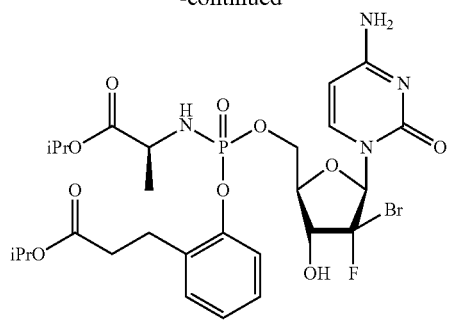
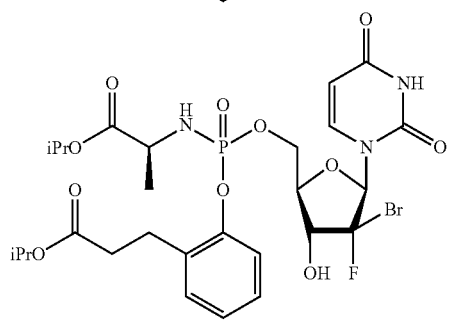
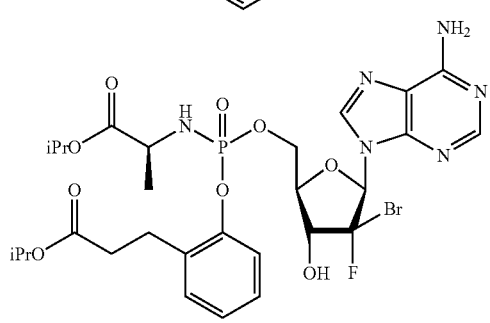
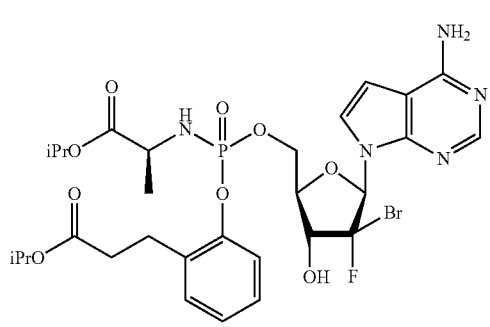
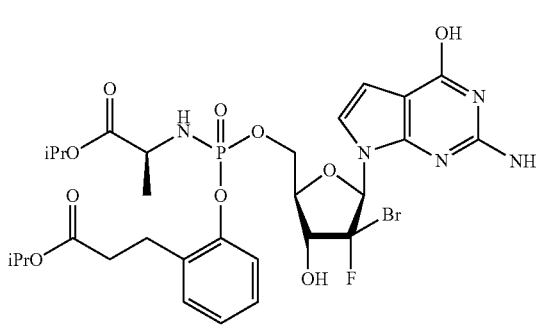
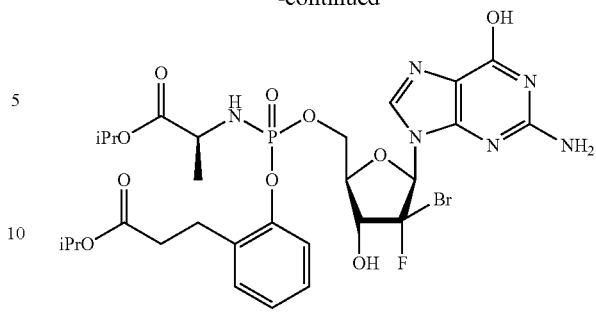
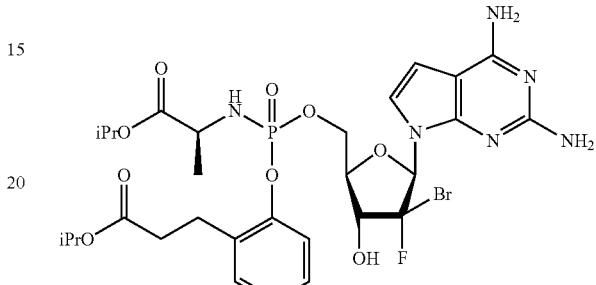
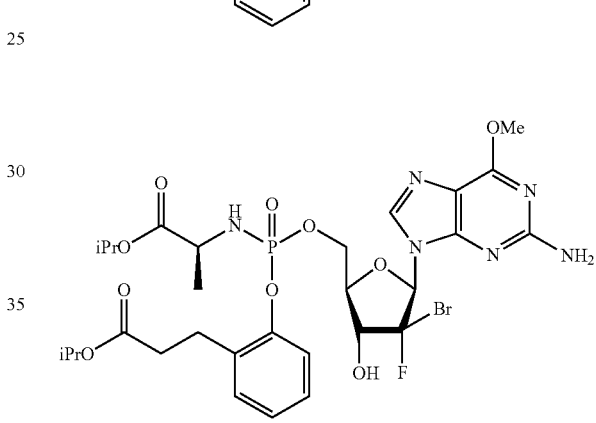
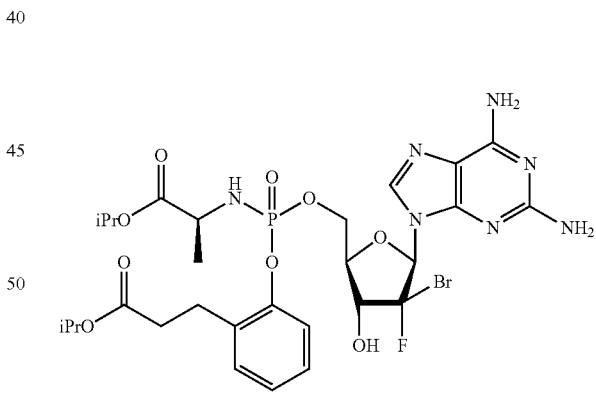
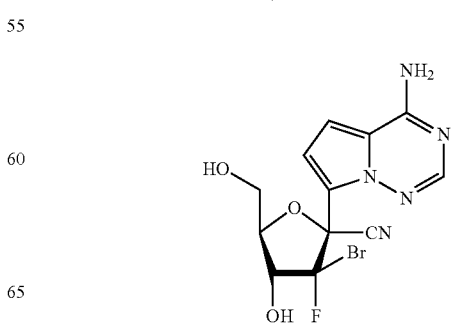

-continued
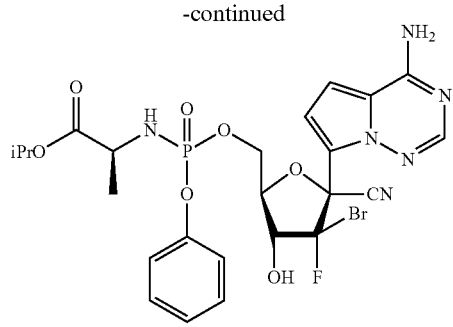
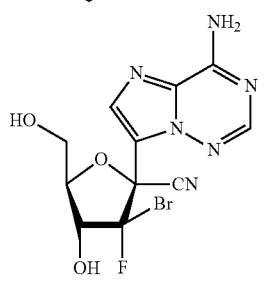
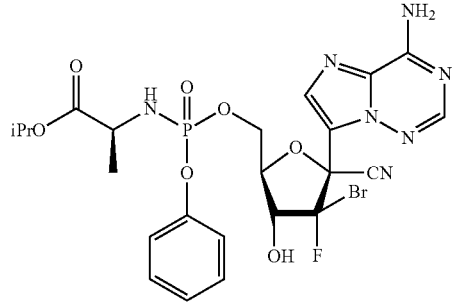
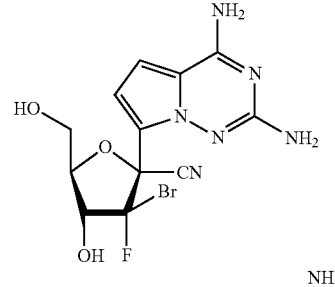
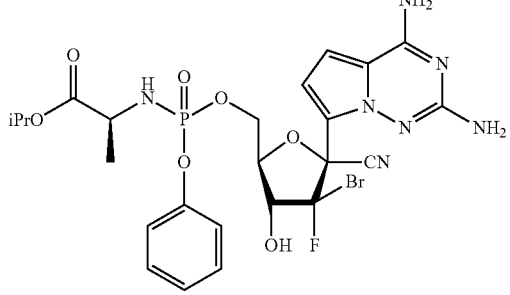
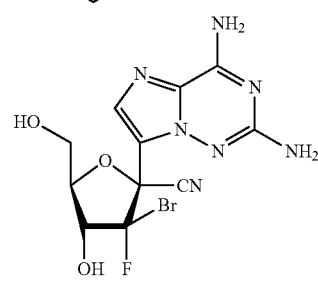
-continued
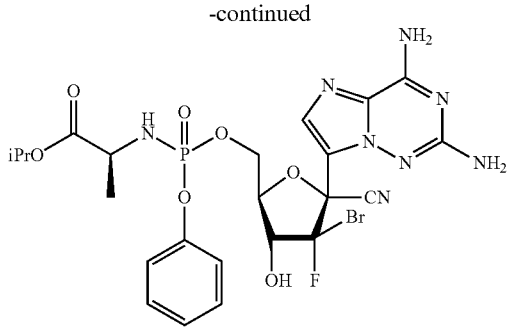
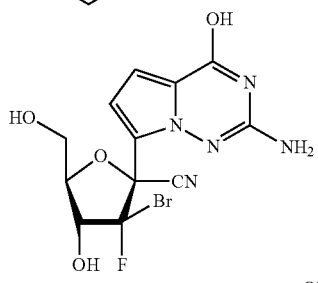
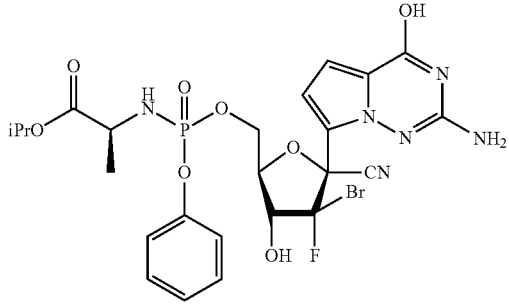
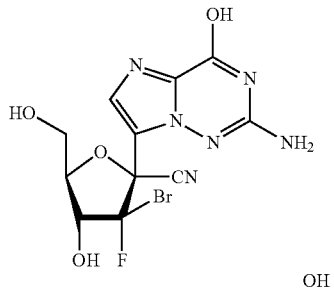
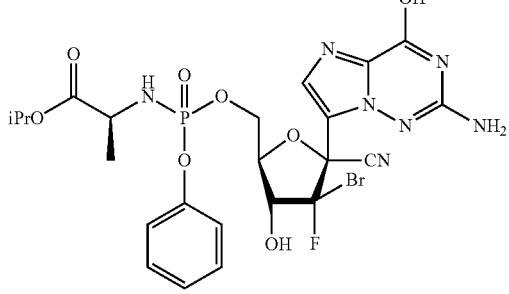
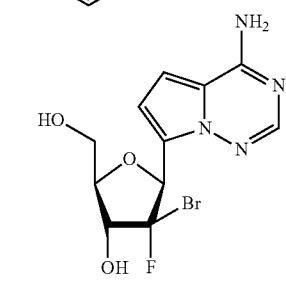

47
-continued
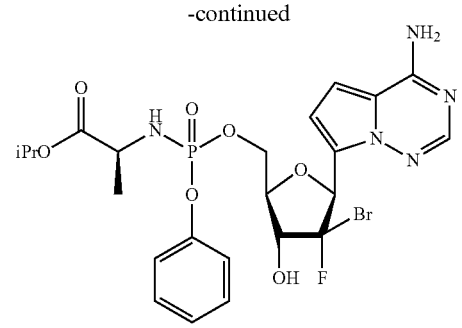
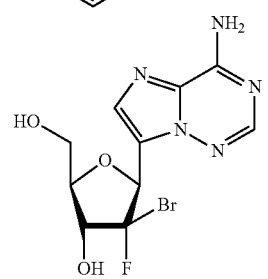
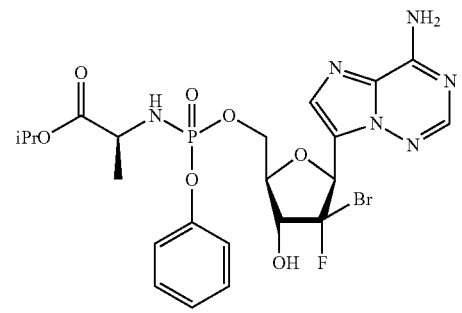
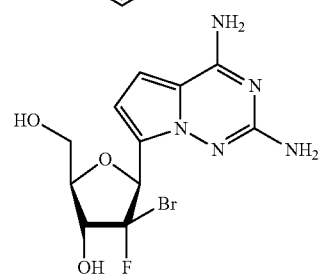
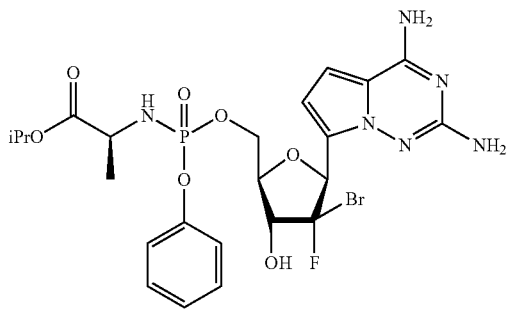
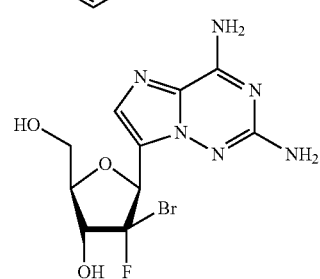
48
-continued
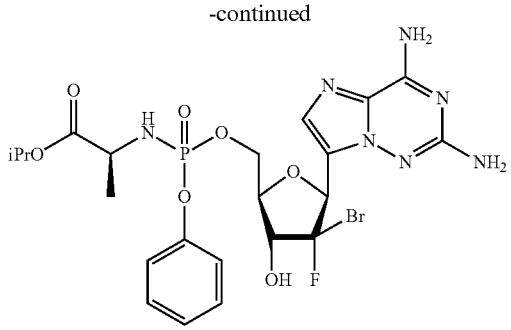
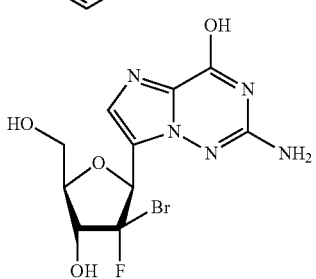
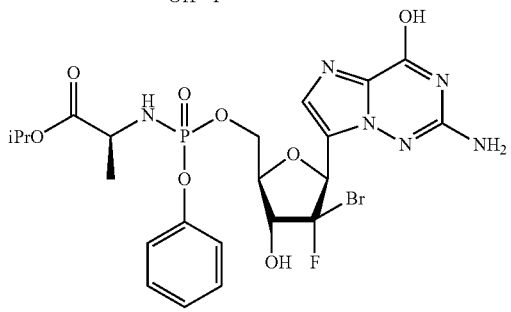
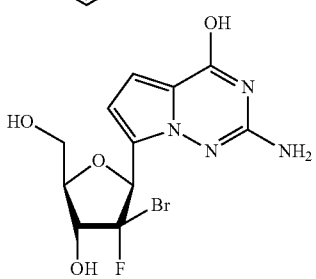
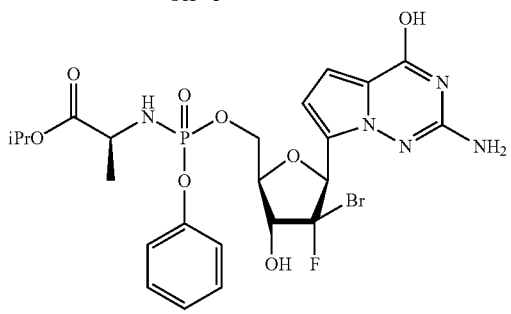
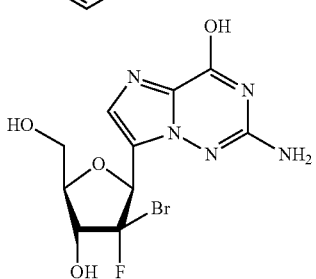

49
-continued
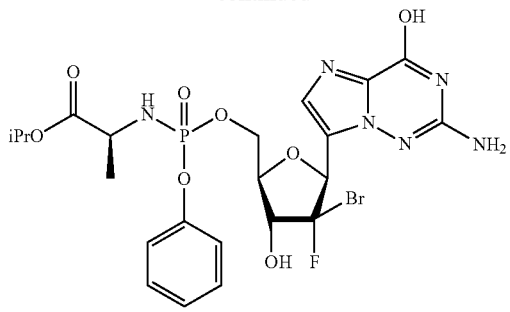
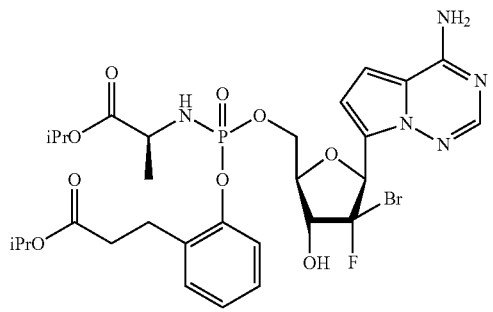
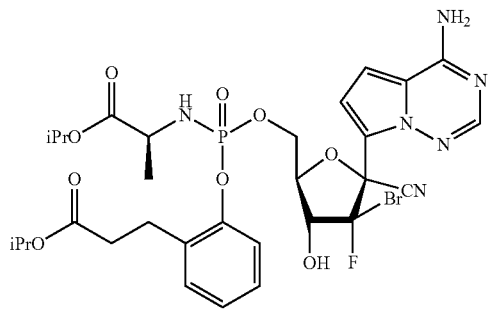
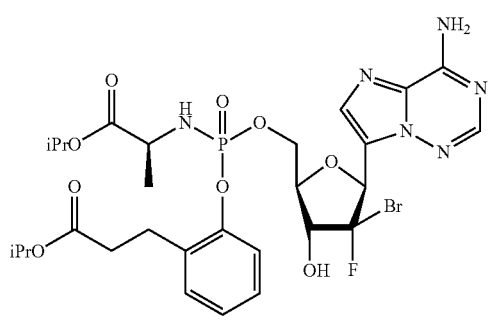
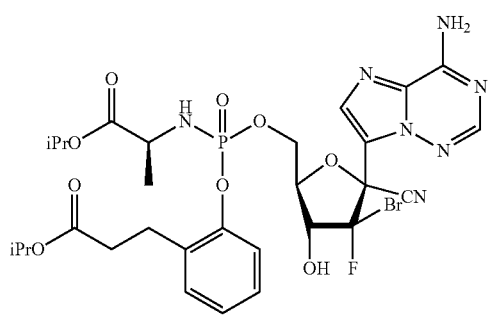
50
-continued
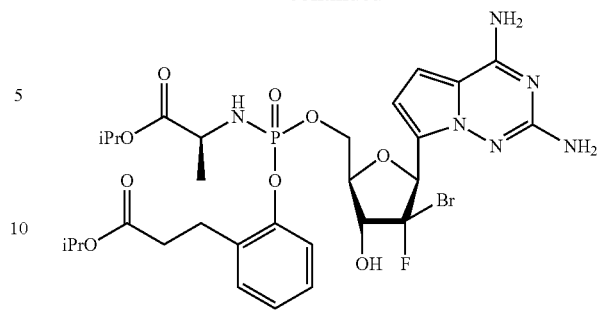
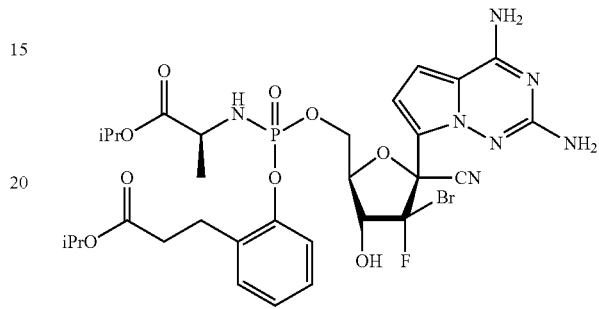
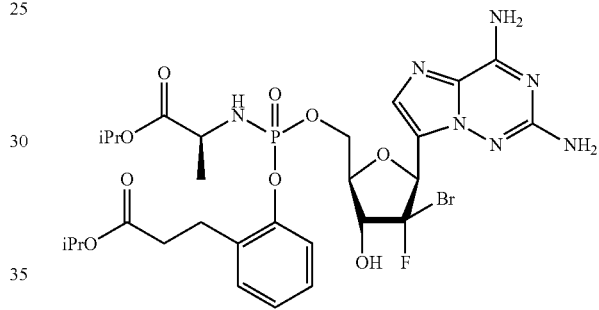
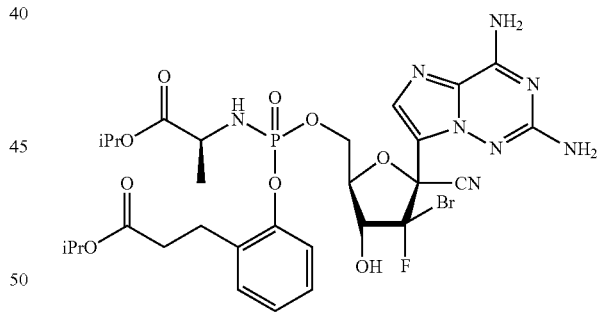
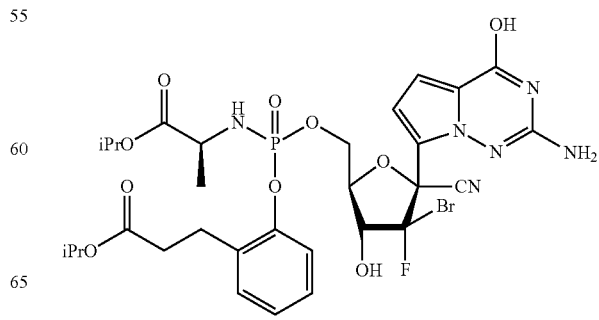

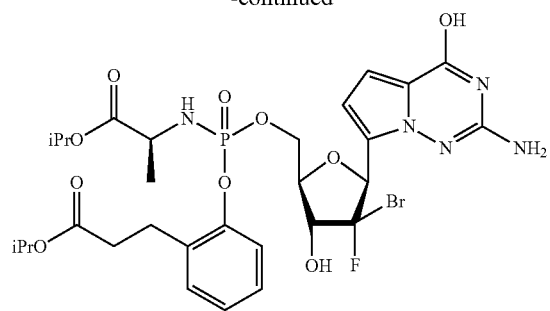
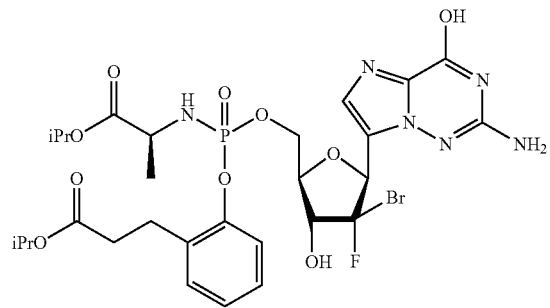
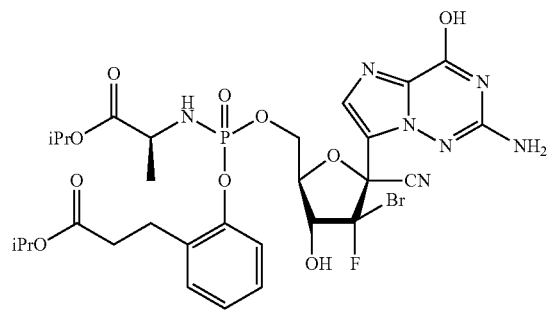
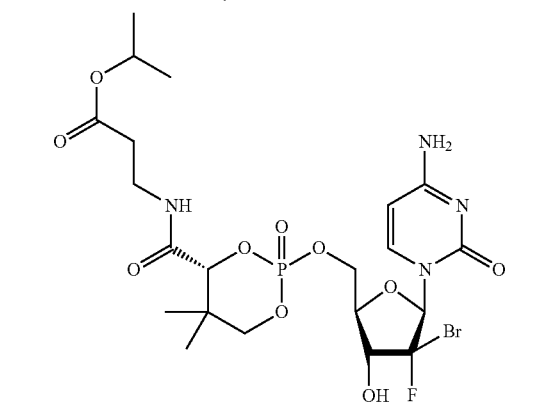
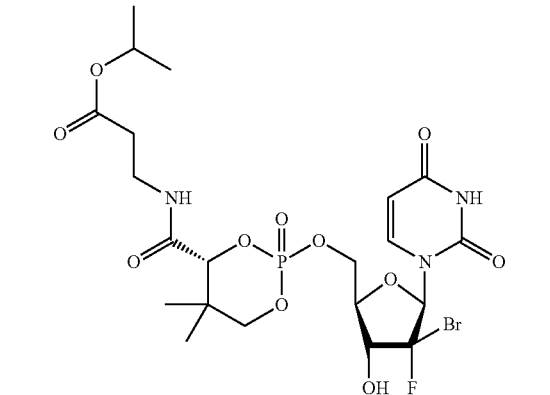
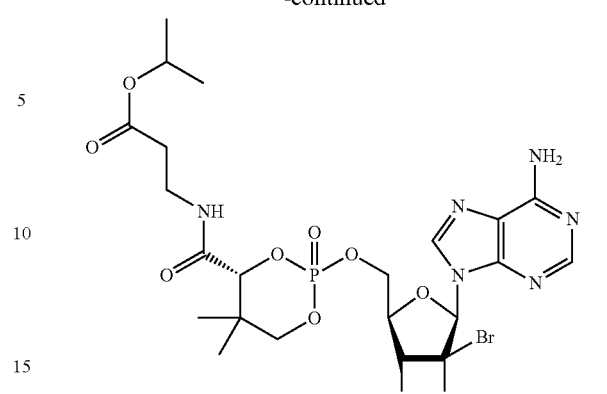
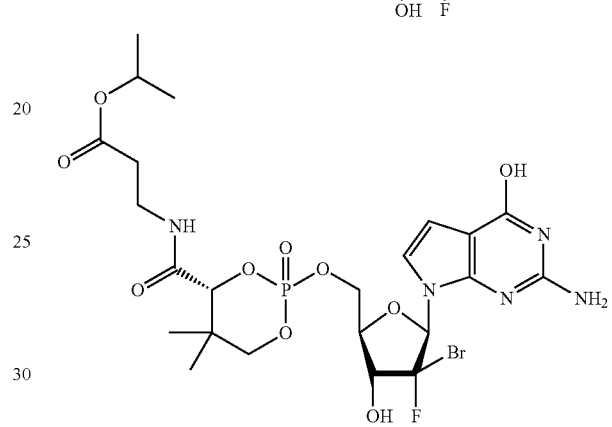
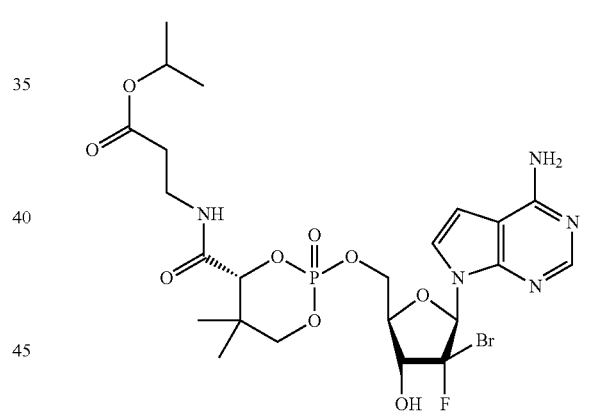
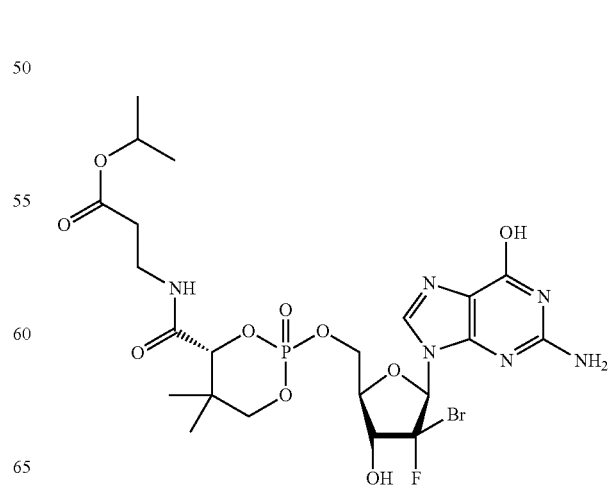

53
-continued
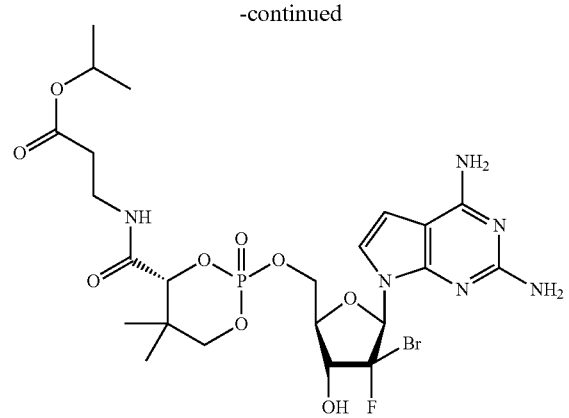
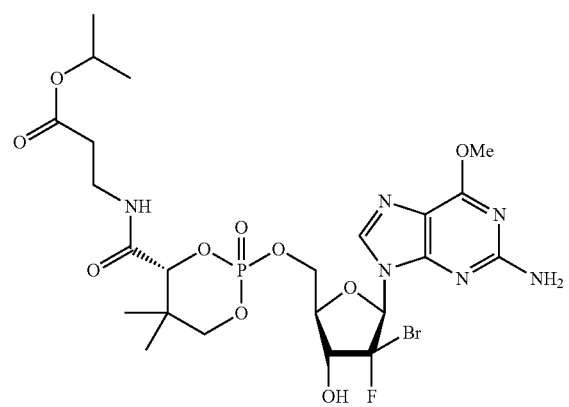
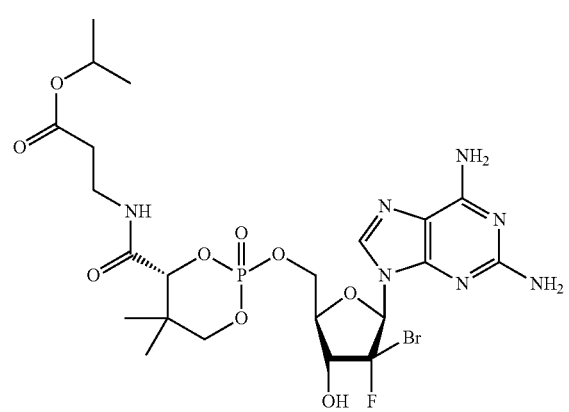
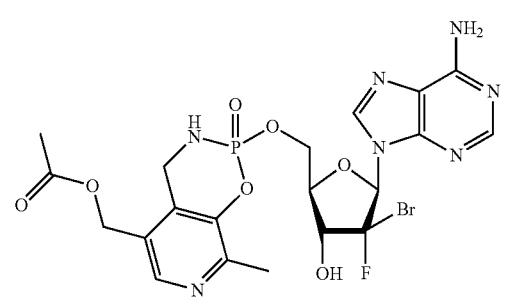
54
-continued
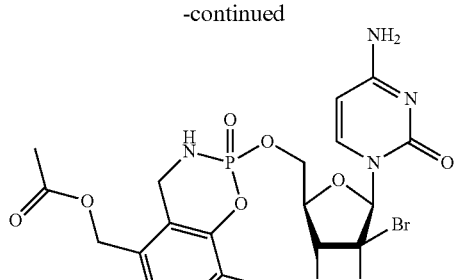
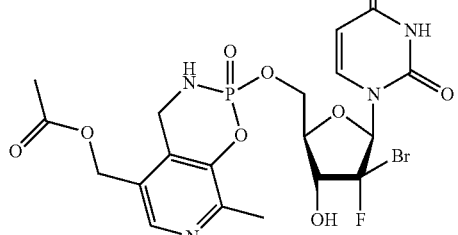
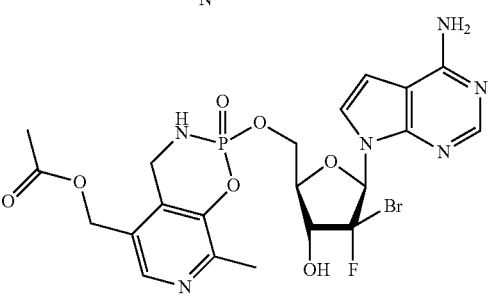
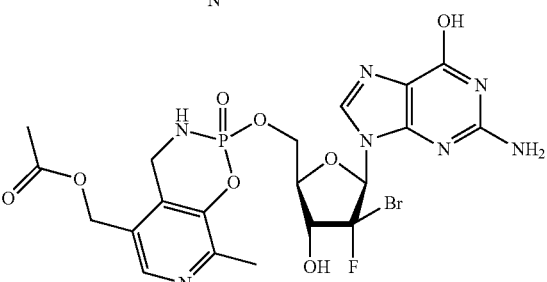
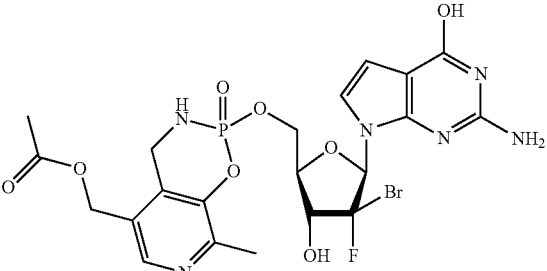
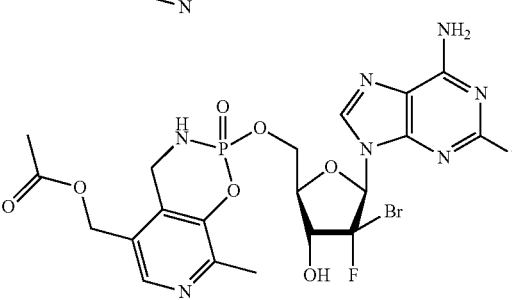

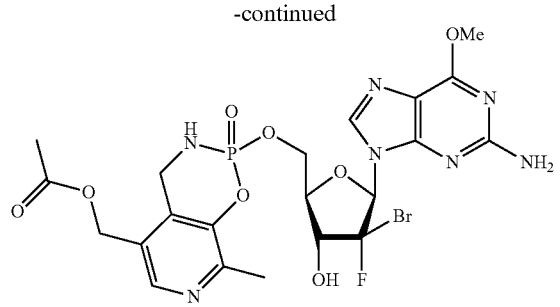
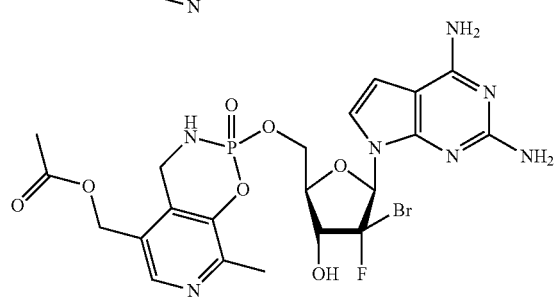
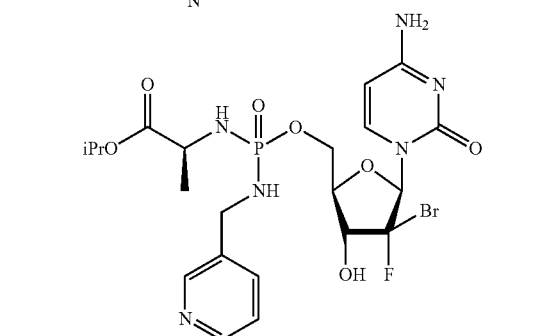
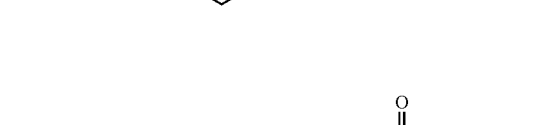
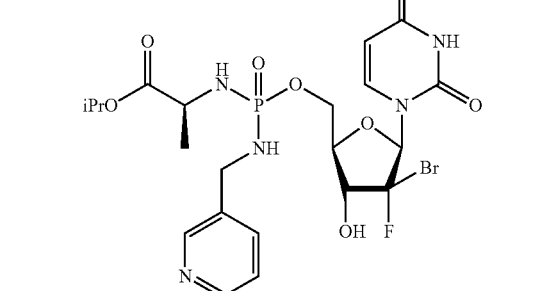
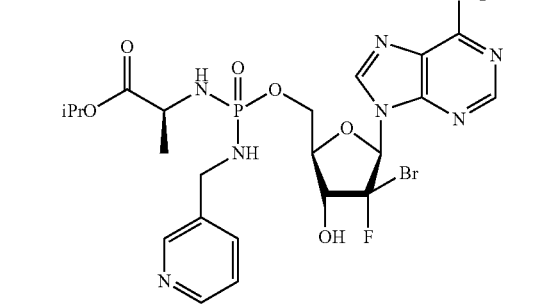

57
-continued
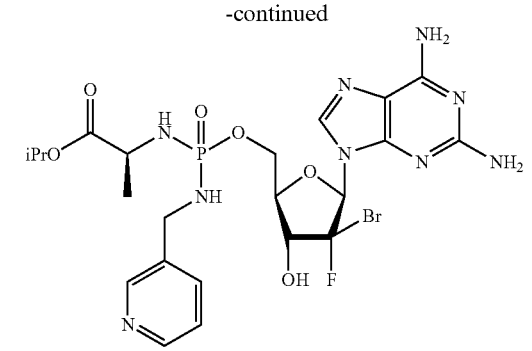
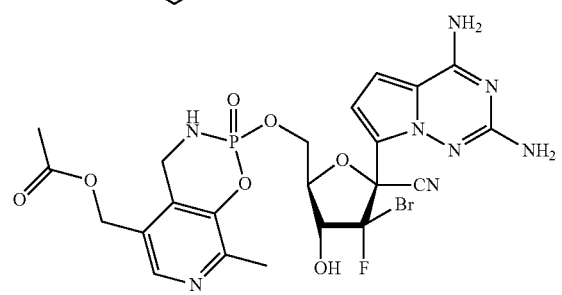
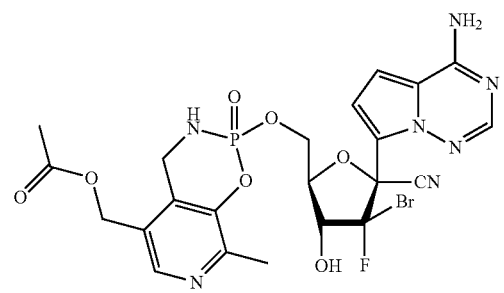
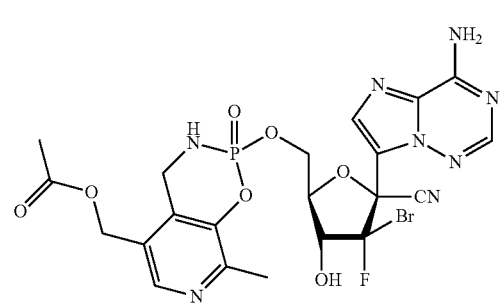
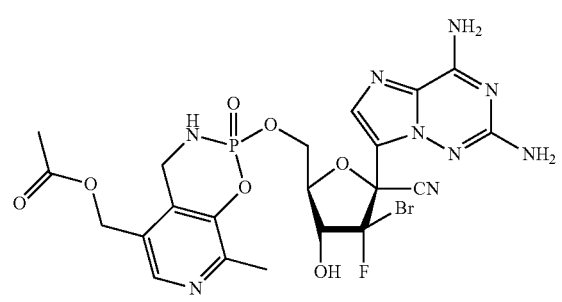
58
-continued
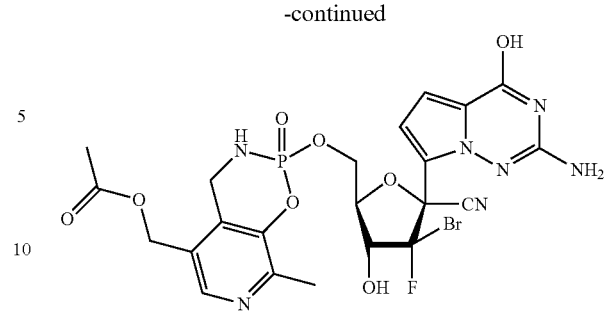
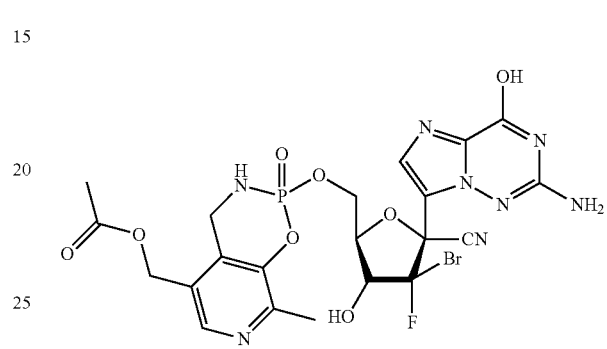
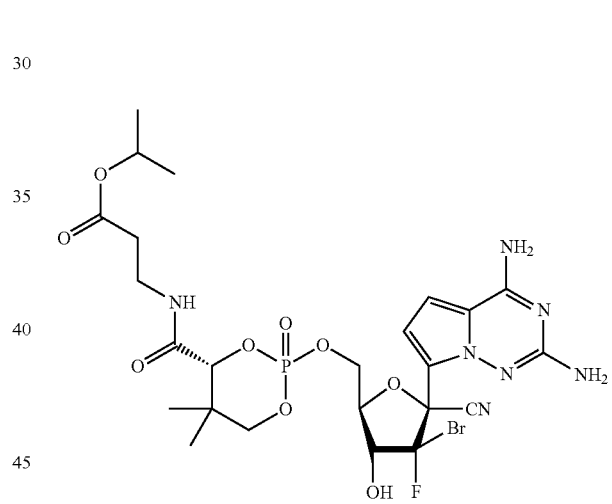
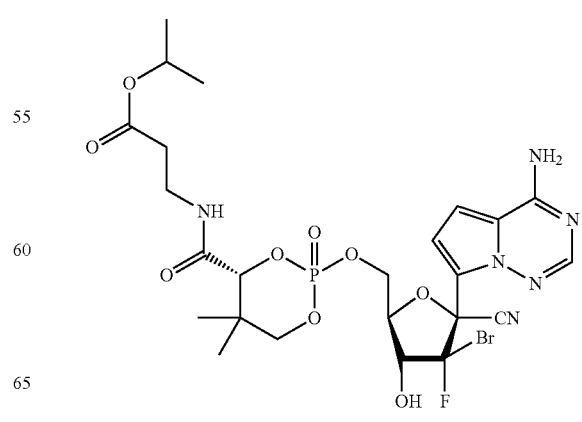

-continued

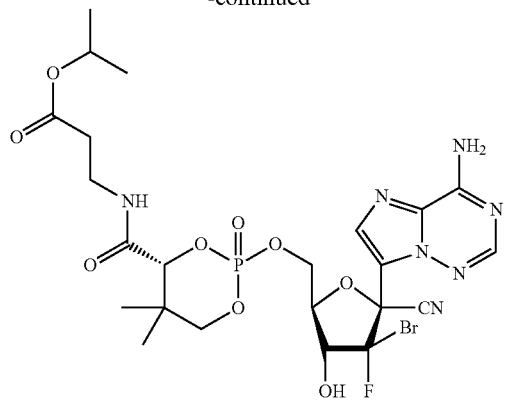

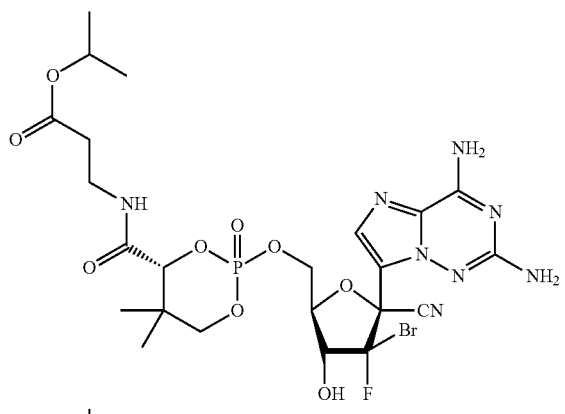

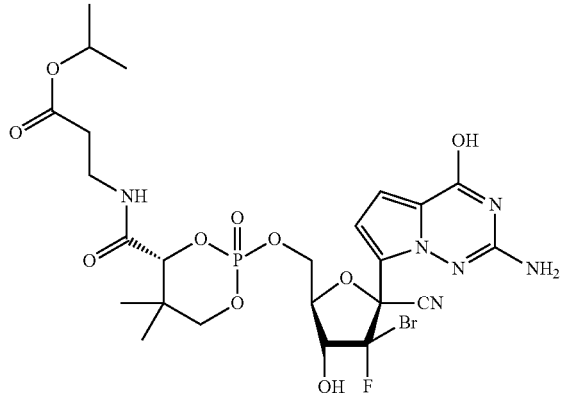

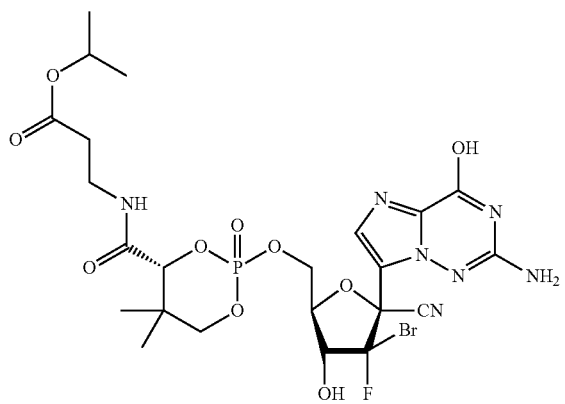

or pharmaceutically acceptable salts thereof.

A particularly preferred compound has the formula:

(Compound 9)

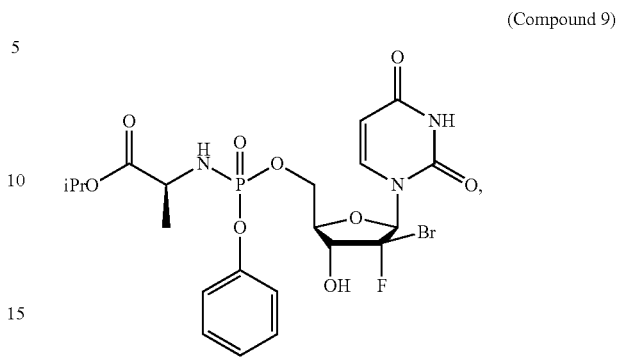

or a pharmaceutically acceptable salt thereof.

Another particularly preferred compound is Compound 7, the 5'-OH analog of Compound 9. This compound is a preferred compound, as it is an intermediate used to prepare Compound 9 and other compounds with different prodrug moieties at the 5'-position.

III Stereoisomerism and Polymorphism

The compounds described herein can have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts. For certain transdermal applications, it can be preferred to use fatty acid salts of the compounds described herein. The fatty acid salts can help penetrate the stratum corneum. Examples of suitable salts include salts of the compounds with stearic acid, oleic acid, lineoleic acid, palmitic acid, caprylic acid, and capric acid.

Pharmaceutically acceptable salts can be obtained using standard procedures well known in the art, for example by reacting a sufficiently basic compound such as an amine with a suitable acid, affording a physiologically acceptable anion. In those cases where a compound includes multiple amine groups, the salts can be formed with any number of the amine groups. Alkali metal (e.g., sodium, potassium or lithium) or alkaline earth metal (e.g., calcium) salts of carboxylic acids can also be made.

A prodrug is a pharmacological substance that is administered in an inactive (or significantly less active) form and subsequently metabolized in vivo to an active metabolite. Getting more drug to the desired target at a lower dose is often the rationale behind the use of a prodrug and is generally attributed to better absorption, distribution, metabolism, and/or excretion (ADME) properties. Prodrugs are usually designed to improve oral bioavailability, with poor absorption from the gastrointestinal tract usually being the limiting factor. Additionally, the use of a prodrug strategy can increase the selectivity of the drug for its intended target thus reducing the potential for off target effects.

V. Methods of Treatment

The compounds described herein can be used to treat or prevent hepatitis C virus (HCV) infections, as well as other flaviviruses, RSV, hepatitis E virus (HEV), influenza and certain types of cancer.

Hosts, including but not limited to humans, suffering from one of these cancers, or infected with one of these viruses, such as HCV or HEV, or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, transdermally, subcutaneously, or topically, in liquid or solid form.

VI. Combination or Alternation Therapy

In one embodiment, the compounds of the invention can be employed together with at least one other antiviral agent, selected from the group consisting of polymerase inhibitors, IMPDH inhibitors, protease inhibitors, and immune-based therapeutic agents.

For example, when used to treat or prevent HCV infection, the active compound or its prodrug or pharmaceutically acceptable salt can be administered in combination or alternation with another anti-HCV including, but not limited to, those of the formulae above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

TABLE 1

FDA-Approved Anti-HCV Compounds and Compounds Currently in Phase II or III Clinical Development*

| Drug Name | Drug category | Company |
| --- | --- | --- |
| sofosbuvir (GS-7977)[1] | Nucleoside | Gilead Sciences |
| mericitabine (RG7128) | Nucleoside | Hoffmann-La Roche/Genentech |
| VX-135 | Nucleoside | Vertex Pharmaceuticals |
| ABT-333 | Non-Nuc pol inh | AbbVie |
| BI 207127 | Non-Nuc pol inh | Boehringer Ingelheim |
| GS-9669 | Non-Nuc pol inh | Gilead Sciences |
| setrobuvir (ANA-595) | Non-Nuc pol inh | Hoffmann-La Roche/Genentech |
| VX-222 | Non-Nuc pol inh | Vertex Pharmaceuticals |
| TMC647055 | Non-Nuc pol inh | Janssen |
| ABT-267 | NS5A | AbbVie |

TABLE 1-continued

FDA-Approved Anti-HCV Compounds and Compounds Currently in Phase II or III Clinical Development*

| Drug Name | Drug category | Company |
| --- | --- | --- |
| daclatasvir (BMS-790052) | NS5A | Bristol-Myers Squibb |
| ledipasvir (GS-5885) | NS5A | Gilead Sciences |
| ACH-3102 | NS5A | Achillion Pharmaceuticals |
| GS-5816 | NS5A | Gilead Sciences |
| GSK2336805 | NS5A | GlaxoSmithKline |
| IDX719 | NS5A | Idenix Pharmaceuticals |
| MK-8742 | NS5A | Merck |
| boceprevir[1] | Protease inhibitor | Merck |
| telaprevir[1] | Protease inhibitor | Vertex |
| ABT-450/r (ritonavir-boosted) | Protease inhibitor | AbbVie |
| asunaprevir (BMS-650032) | Protease inhibitor | Bristol-Myers Squibb |
| faldaprevir (BI 201335) | Protease inhibitor | Boehringer Ingelheim |
| simeprevir (TMC435)[1] | Protease inhibitor | Janssen/Tibotec/Medivir |
| danoprevir/r (RG7227) (ritonavir-boosted) | Protease inhibitor | Hoffmann-La Roche/Genentech |
| GS-9451 | Protease inhibitor | Gilead Sciences |
| MK-5172 | Protease inhibitor | Merck |
| sovaprevir (ACH-1625) | Protease | Achillion |

*Adapted from TAG pipeline report: http://www.pipelinereport.org/sites/g/files/g575521/f/201306/HCV.pdf
[1]FDA approved treatment for HCV infection Additional compounds which can be used in combination therapy include:

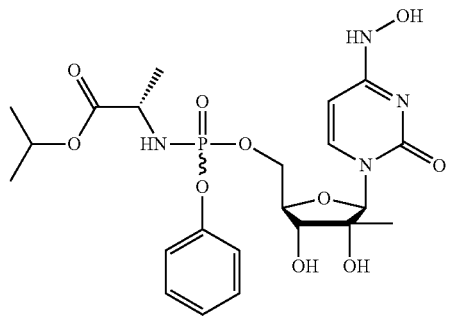

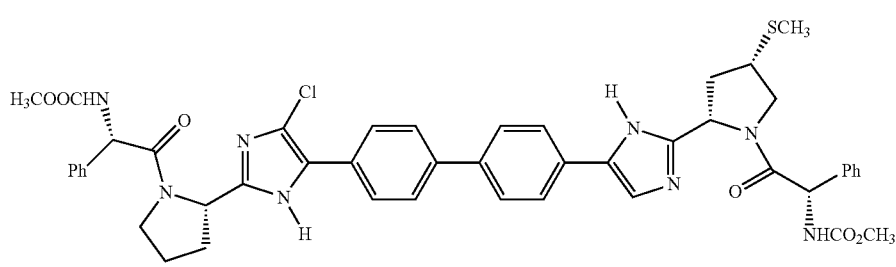

-continued

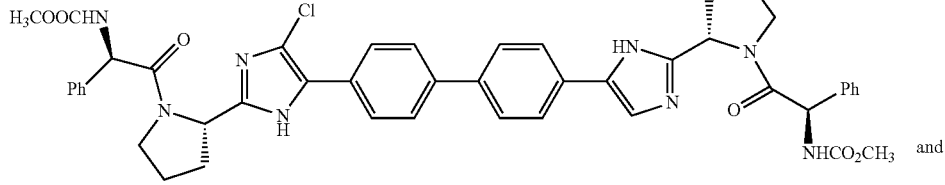

Faldepravir:

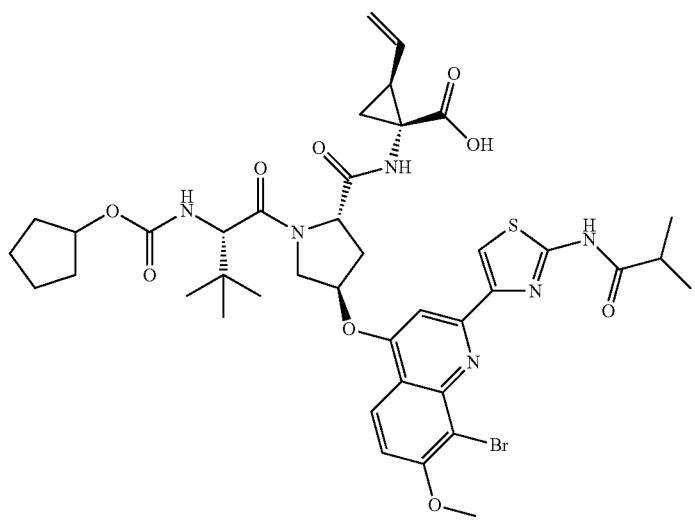

The compounds described herein can also be combined with Ledipasvir, which has the following formula:

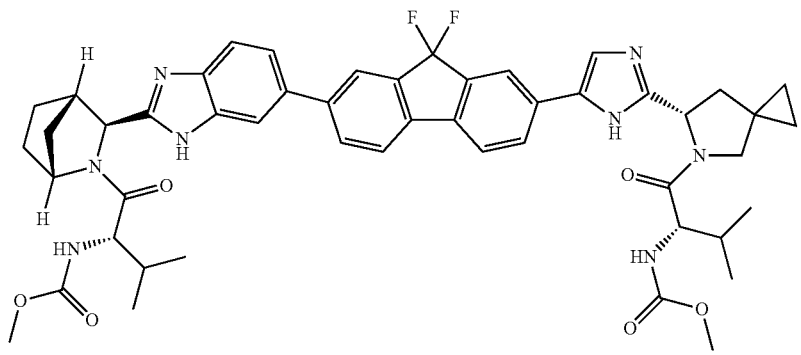 [SMILES: COC(=O)N[C@H](C(=O)N1CC2(CC2)C[C@H]1c1ncc(-c2ccc3c(c2)C(F)(F)c2cc(-c4ccc5nc([C@@H]6[C@H]7CC[C@H](C7)N6C(=O)[C@@H](NC(=O)OC)C(C)C)[nH]c5c4)ccc2-3)[nH]1)C(C)C]

The compounds can also be used to treat cancer. Patients that can be treated with the compounds described herein, and the pharmaceutically acceptable salts and prodrugs of these compounds, according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a method of and to a pharmaceutical composition for inhibiting abnormal cellular proliferation in a patient which comprises an amount of a compound described herein, or a pharmaceutically acceptable salt or prodrug thereof, and an amount of one or more substances selected from anti-angiogenesis agents, signal transduction inhibitors, and antiproliferative agents. When used to treat cancer, the compounds can be administered in combination or alternation with these or other types of anticancer agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of formula 1 and pharmaceutical compositions described herein. Examples of useful COX-II inhibitors include CELEBREX (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The compounds described herein can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), ABX-EGF (Abgenix/Cell Genesys), EMD-7200 (Merck KgaA), EMD-5590 (Merck KgaA), MDX-447/H-477 (Medarex Inc. of Annandale, N.J., USA and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co. of Whitehouse Station, N.J., USA), VRCTC-310 (Ventech Research), EGF fusion toxin (Seragen Inc. of Hopkinton, Mass.), DAB-389 (Seragen/Lilgand), ZM-252808 (Imperical Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGFR Vaccine (York Medical/Centro de Immunologia Molecular (CIM)). These and other EGFR-inhibiting agents can be used in the present invention.

VEGF inhibitors, for example CP-547,632 (Pfizer Inc., N.Y.), AG-13736 (Agouron Pharmceuticals, Inc. a Pfizer Company), SU-5416 and SU-6668 (Sugen Inc. of South San Francisco, Calif., USA), and SH-268 (Schering) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as CP-358,774 (OSI-774) (Tarceva) (OSI Pharmaceuticals, Inc.), GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compounds described herein in accordance with the present invention.

The compounds can also be used with other agents useful in treating abnormal cellular proliferation or cancer, including, but not limited to, agents capable of enhancing antitumor immune responses, such as CTLA4 (cytotoxic lymphocite antigen 4) antibodies, and other agents capable of blocking CTLA4; and antiproliferative agents such as other farnesyl protein transferase inhibitors, and the like. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

Other anti-angiogenesis agents, including, but not limited to, other COX-II inhibitors, other MMP inhibitors, other anti-VEGF antibodies or inhibitors of other effectors of vascularization can also be used.

VIII. Pharmaceutical Compositions

Hosts, including but not limited to humans, infected with HCV can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for will be in the range of between about 0.01 and about 10 mg/kg, more generally, between about 0.1 and 5 mg/kg, and, preferably, between about 0.5 and about 2 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 600 mg, preferably 70 to 600 mg of active ingredient per unit dosage form. An oral dosage of 5-400 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antiviral compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Transdermal Formulations

In some embodiments, the compositions are present in the form of transdermal formulations, such as that used in the FDA-approved agonist rotigitine transdermal (Neupro patch). Another suitable formulation is that described in U.S. Publication No. 20080050424, entitled "Transdermal Therapeutic System for Treating Parkinsonism." This formulation includes a silicone or acrylate-based adhesive, and can include an additive having increased solubility for the active substance, in an amount effective to increase dissolving capacity of the matrix for the active substance.

The transdermal formulations can be single-phase matrices that include a backing layer, an active substance-containing self-adhesive matrix, and a protective film to be removed prior to use. More complicated embodiments contain multiple-layer matrices that may also contain non-adhesive layers and control membranes. If a polyacrylate adhesive is used, it can be crosslinked with multivalent metal ions such as zinc, calcium, aluminum, or titanium ions, such as aluminum acetylacetonate and titanium acetylacetonate.

When silicone adhesives are used, they are typically polydimethylsiloxanes. However, other organic residues such as, for example, ethyl groups or phenyl groups may in principle be present instead of the methyl groups. Because the active compounds are amines, it may be advantageous to use amine-resistant adhesives. Representative amine-resistant adhesives are described, for example, in EP 0 180 377.

Representative acrylate-based polymer adhesives include acrylic acid, acrylamide, hexylacrylate, 2-ethylhexylacrylate, hydroxyethylacrylate, octylacrylate, butylacrylate, methylacrylate, glycidylacrylate, methacrylic acid, methacrylamide, hexylmethacrylate, 2-ethylhexylmethacrylate, octylmethacrylate, methylmethacrylate, glycidylmethacrylate, vinylacetate, vinylpyrrolidone, and combinations thereof.

The adhesive must have a suitable dissolving capacity for the active substance, and the active substance most be able to move within the matrix, and be able to cross through the contact surface to the skin. Those of skill in the art can readily formulate a transdermal formulation with appropriate transdermal transport of the active substance.

Certain pharmaceutically acceptable salts tend to be more preferred for use in transdermal formulations, because they can help the active substance pass the barrier of the stratum corneum. Examples include fatty acid salts, such as stearic acid and oleic acid salts. Oleate and stearate salts are relatively lipophilic, and can even act as a permeation enhancer in the skin.

Permeation enhancers can also be used. Representative permeation enhancers include fatty alcohols, fatty acids, fatty acid esters, fatty acid amides, glycerol or its fatty acid esters, N-methylpyrrolidone, terpenes such as limonene, alpha-pinene, alpha-terpineol, carvone, carveol, limonene oxide, pinene oxide, and 1,8-eucalyptol.

The patches can generally be prepared by dissolving or suspending the active agent in ethanol or in another suitable organic solvent, then adding the adhesive solution with stirring. Additional auxiliary substances can be added either to the adhesive solution, the active substance solution or to the active substance-containing adhesive solution. The solution can then be coated onto a suitable sheet, the solvents removed, a backing layer laminated onto the matrix layer, and patches punched out of the total laminate.

Nanoparticulate Compositions

The compounds described herein can also be administered in the form of nanoparticulate compositions.

In one embodiment, the controlled release nanoparticulate formulations comprise a nanoparticulate active agent to be administered and a rate-controlling polymer which functions to prolong the release of the agent following administration.

In this embodiment, the compositions can release the active agent, following administration, for a time period ranging from about 2 to about 24 hours or up to 30 days or longer. Representative controlled release formulations including a nanoparticulate form of the active agent are described, for example, in U.S. Pat. No. 8,293,277.

Nanoparticulate compositions comprise particles of the active agents described herein, having a non-crosslinked surface stabilizer adsorbed onto, or associated with, their surface.

The average particle size of the nanoparticulates is typically less than about 800 nm, more typically less than about 600 nm, still more typically less than about 400 nm, less than about 300 nm, less than about 250 nm, less than about 100 nm, or less than about 50 nm. In one aspect of this embodiment, at least 50% of the particles of active agent have an average particle size of less than about 800, 600, 400, 300, 250, 100, or 50 nm, respectively, when measured by light scattering techniques.

A variety of surface stabilizers are typically used with nanoparticulate compositions to prevent the particles from clumping or aggregating. Representative surface stabilizers are selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxy-poly-(glycidol), SA9OHCO, decanoyl-N-methylglucamide, n-decyl-D-glucopyranoside, n-decyl-D-maltopyranoside, n-dodecyl-D-glucopyranoside, n-dodecyl-D-maltoside, heptanoyl-N-methylglucamide, n-heptyl-D-glucopyranoside, n-heptyl-D-thioglucoside, n-hexyl-D-glucopyranoside, nonanoyl-N-methylglucamide, n-nonyl-D-glucopyranoside, octanoyl-N-methylglucamide, n-octyl-D-glucopyranoside, and octyl-D-thioglucopyranoside. Lysozymes can also be used as surface stabilizers for nanoparticulate compositions. Certain nanoparticles such as poly(lactic-co-glycolic acid) (PLGA)-nanoparticles are known to target the liver when given by intravenous (IV) or subcutaneously (SQ).

Because HCV and other viruses cause damage to, and are present in the liver, in one embodiment, the nanoparticles or other drug delivery vehicles are targeted to the liver. One such type of liver-targeted drug delivery vehicle is described in Park, et al., Mol Imaging. February 2011; 10(1): 69-77, and uses Glypican-3 (GPC3) as a molecular target. Park taught using this target for hepatocellular carcinoma (HCC), a primary liver cancer frequently caused by chronic persistent hepatitis.

In one aspect of this embodiment, this drug delivery vehicle is also used to target therapeutics to the liver to treat viral infections. Further, since the compounds described herein have anti-cancer uses, this type of system can target the compounds to the liver and treat liver cancers. GPC3 is a heparan sulfate proteoglycan that is not expressed in normal adult tissues, but significantly over-expressed in up to 80% of human HCC's. GPC3 can be targeted, for example, using antibody-mediated targeting and binding (See Hsu, et al., Cancer Res. 1997; 57:5179-84).

Another type of drug delivery system for targeting the liver is described in U.S. Pat. No. 7,304,045. The '045 patent discloses a dual-particle tumor or cancer targeting system that includes a first ligand-mediated targeting nanoparticle conjugated with galactosamine, with the ligand being on a target cell. The first nanoparticle includes poly(γ-glutamic acid)/poly(lactide) block copolymers and n antiviral compound, which in this case is a compound described herein, and in the '045 patent, was gancyclovir. A second nanoparticle includes poly(γ-glutamic acid)/poly(lactide) block copolymers, an endothelial cell-specific promoter, and a (herpes-simplex-virus)-(thymidine kinase) gene constructed plasmid, and provides enhanced permeability and retention-mediated targeting. The first and said second nanoparticles are mixed in a solution configured for delivering to the liver. When the disorder to be treated is a liver tumor or cancer, the delivery can be directly to, or adjacent to, the liver tumor or cancer.

Representative rate controlling polymers into which the nanoparticles can be formulated include chitosan, polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcelluose (HPMC), sodium carboxymethylcellulose (CMC), poly(ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly(vinyl acetate), polymers derived from acrylic or methacrylic acid and their respective esters, and copolymers derived from acrylic or methacrylic acid and their respective esters.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Nonionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly (ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−) Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive nanoparticulate compositions having cationic surface stabilizers;" U.S. Pat. No. 6,431,478 for "Small Scale Mill;" and U.S. Pat. No. 6,432,381 for "Methods for targeting drug delivery to the upper and/or lower gastrointestinal tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

The nanoparticle formulations including the compounds described herein, and also in the form of monophosphate prodrugs, and monophosphate, diphosphate, and triphosphate analogs, can be used to treat or prevent infections by flaviviruses, RSV, HEV, and influenza infections, and to treat or prevent certain types of cancers, including, but not limited to, liver cancer, acute myeloid leukemia, pancreatic cancer, lung cancer, ovarian cancer, colon cancer, rectal cancer, anal cancer, head and neck cancers, breast cancer, head and neck cancers, stomach cancer, some skin cancers, and other types of cancer described elsewhere herein that are treatable with anti-cancer nucleosides.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

Controlled Release Formulations

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:
ACN acetonitrile aq aqueous
BSA Bis(trimnethylsilyl)acetamide
BzCl Benzoyl chloride
CDI carbonyldiimidazole
DIPEA diisopropyl ethyl amine (Hünig's base)
DMF N,N-dimethylformamide
DMSO dimethylsulfoxide
EDC 1-ethyl-3-(3-dimethyllaminopropyl) carbodiimide hydrochloride
EtOAc ethyl acetate
h hour
HOBt N-hydroxybenzotriazole
LiHMDS Lithium Hexamethyldisilazide
M molar
min minute
Ms mesylate
NCS N-chlorosuccinimide
NBS N-bromosuccinimide
NFSI N-fluorobenzenesulfonimide
NIS N-iodosuccinimide
NMI 1-Methylimidazole
Pyr pyridine
rt or RT room temperature
TBDPSCl tert-Butyl(chloro)diphenylsilane
TBAF Tetrabutylammonium fluoride
TBAT tetrabutylammonium triphenyldifluorosilicate
TBTU O-Benzotriazol-1-yl)-N,N,N',N'-tetramethyluronium tetrafluoroborate
TEA triethylamine
THF tetrahydrofuran
Ts tosylate IX. General Methods for Preparing Active Compounds Methods for the facile preparation of active compounds are known in the art and result from the selective combination known methods. The compounds disclosed herein can be prepared as described in detail below, or by other methods known to those skilled in the art. It will be understood by one of ordinary skill in the art that variations of detail can be made without departing from the spirit and in no way limiting the scope of the present invention.

The various reaction schemes are summarized below.

Scheme 1 is a non-limiting example of the synthesis of active compounds of the present invention, and in particular, a synthetic approach to nucleosides 1.

Scheme 2 is a non-limiting example of the synthesis of active compounds of the present invention, and in particular, an alternate synthetic approach to nucleosides 1.

Scheme 3 is a non-limiting example of the synthesis of active compounds of the present invention, and in particular, a synthetic approach to monophosphate prodrugs I.

Scheme 4 is a non-limiting example of the synthesis of active compounds of the present invention, and in particular, a synthetic approach to monophosphate prodrugs IV, V and VI.

Scheme 5 is a non-limiting example of the synthesis of active compounds of the present invention, and in particular, a synthetic approach to monophosphate prodrugs VII.

Scheme 6 is a non-limiting example of the synthesis of active compounds of the present invention, and in particular, a synthetic approach to monophosphate prodrugs VIII.

Compounds of Formula A can be prepared by first preparing nucleosides 1, which in turn can be accomplished by one of ordinary skill in the art, using methods outlined in: (a) Rajagopalan, P.; Boudinot, F. D; Chu, C. K.; Tennant, B. C.; Baldwin, B. H.; Antiviral Nucleosides: Chiral Synthesis and Chemotheraphy: Chu, C. K.; Eds. Elsevier: 2003. b) Recent Advances in Nucleosides: Chemistry and Chemotherapy: Chu, C. K.; Eds. Elsevier: 2002. c) Frontiers in Nucleosides & Nucleic Acids, 2004, Eds. R. F. Schinazi & D. C. Liotta, IHL Press, Tucker, G A, USA, pp: 319-37 d) Handbook of Nucleoside Synthesis: Vorbruggen H. & Ruh-Pohlenz C. John Wiley & sons 2001), and by general Schemes 1-2. Specifically, nucleosides 1 can be prepared by coupling sugar 2 with a protected, silylated or free nucleoside base in the presence of Lewis acid such as TMSOTf. Deprotection of the 3'- and 5'-hydroxyls gives nucleoside 1.

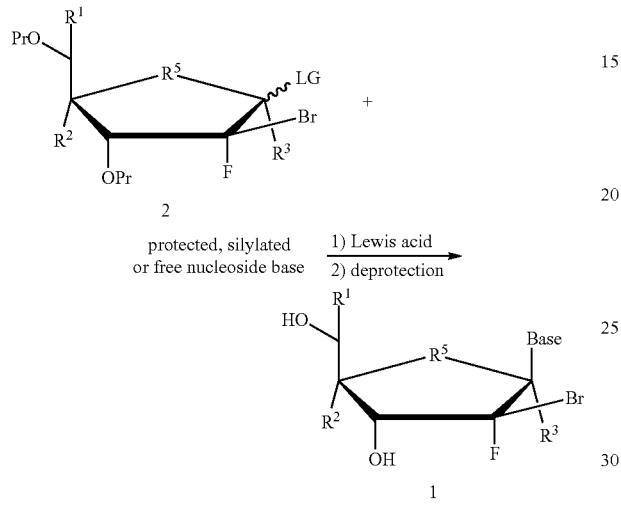

Scheme 1 A synthetic approach to nucleosides 1.
(Base are as defined in active compound section)

nucleoside base may contain suitable protection; Pr = protection; LG = OCOalkyl, OCOaryl, OCOalkylaryl; $R^1$, $R^2$, $R^3$, and $R^5$ are as defined in active compound section In the schemes described herein, if a nucleoside base includes functional groups that might interfere with, or be decomposed or otherwise converted during the coupling steps, such functional groups can be protected using suitable protecting groups. After the coupling step, protected functional groups, if any, can be deprotected.

Alternatively, nucleosides 1 can be prepared from 1'-halo, 1'-sulfonate or 1'-hydroxy compounds 3. For the case of 1'-halo or 1'-sulfonate a protected or free nucleoside base in the presence of a base such as triethyl amine or sodium hydride followed by deprotection would give nucleosides 1. For the case of 1'-hydroxy a protected or free nucleoside base in the presence of a Mitsunobu coupling agent such as diisopropyl azodicarboxylate followed by deprotection would give nucleosides 1.

Scheme 2 An alternate synthetic approach to nucleosides 1.
(Base are as defined in active compound section)

nucleoside base may contain suitable protection; Pr = protection; X = halogen, sulfonate or OH; $R^1$, $R^2$, $R^3$, and $R^5$ are as defined in active compound section In the case of C-nucleosides prepared from bases:

1)

2)

methods outlined in WO09132123, WO09132135, WO2011150288 and WO2011035250 can be used.

Monophosphate prodrugs I can be prepared as outlined in Scheme 3 starting from phenol 4. Exposure of 4 to phosphorous oxychloride or phosphorothioyl trichloride provides 5, which is subsequently allowed to react with an amino ester 6 to give phosphoramidate 7. Nucleoside 1 can next be converted to monophosphate analog 8 by reaction of the 5'-hydroxyl group with the chlorophosphorylamino propanoate, 7. Removal of protecting groups from the base and/or sugar of, if present, provides monophosphate prodrugs I.

Scheme 3 A synthetic approach to monophosphate prodrugs I.
(Base, $R^1$, $R^2$, $R^3$, $R^5$, $R^{16}$, $R^{17}$, and $R^{18}$ are as defined in active compound section).

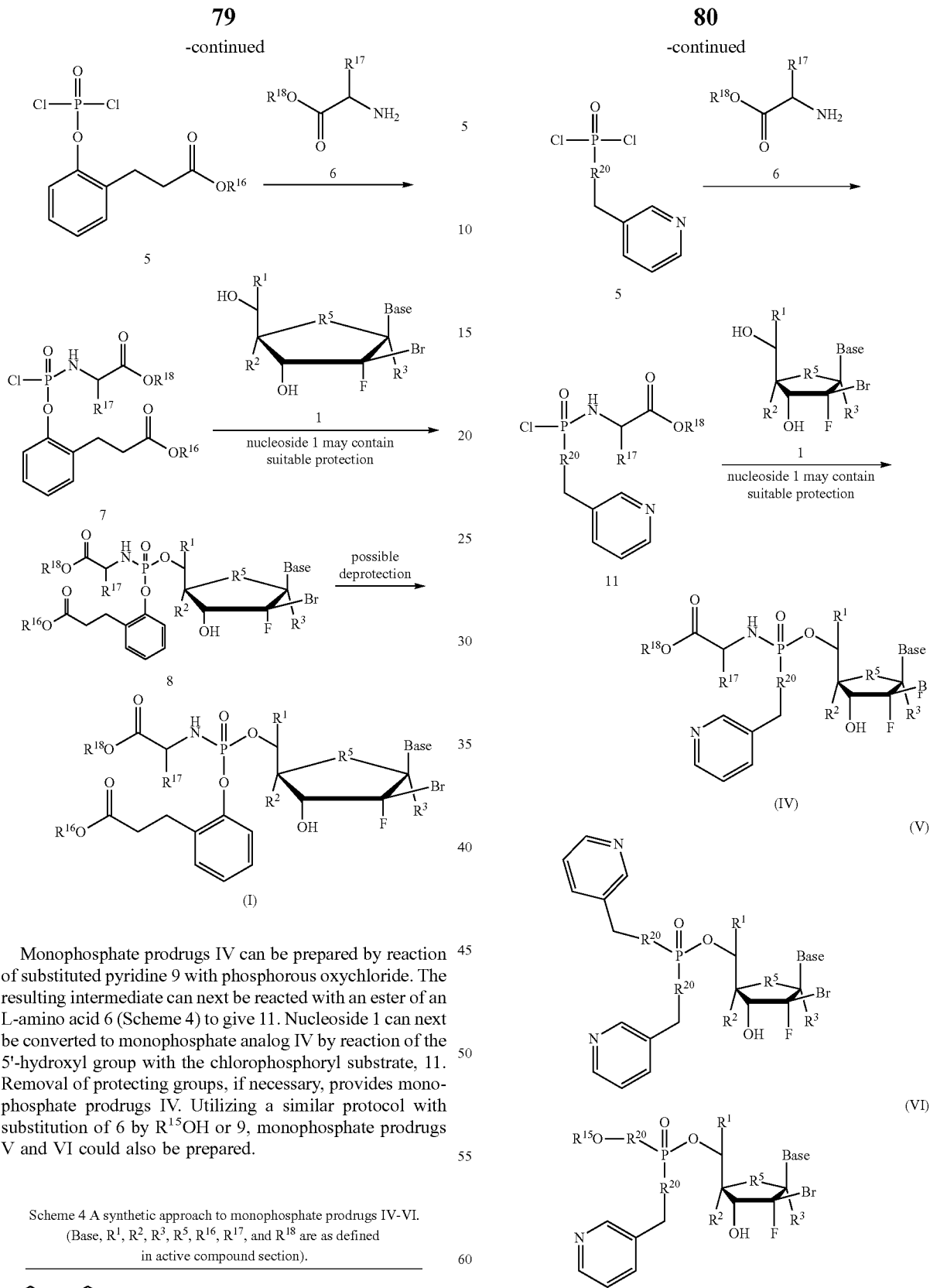

Monophosphate prodrugs IV can be prepared by reaction of substituted pyridine 9 with phosphorous oxychloride. The resulting intermediate can next be reacted with an ester of an L-amino acid 6 (Scheme 4) to give 11. Nucleoside 1 can next be converted to monophosphate analog IV by reaction of the 5'-hydroxyl group with the chlorophosphoryl substrate, 11. Removal of protecting groups, if necessary, provides monophosphate prodrugs IV. Utilizing a similar protocol with substitution of 6 by $R^{15}OH$ or 9, monophosphate prodrugs V and VI could also be prepared.

Scheme 4 A synthetic approach to monophosphate prodrugs IV-VI. (Base, $R^1$, $R^2$, $R^3$, $R^5$, $R^{16}$, $R^{17}$, and $R^{18}$ are as defined in active compound section).

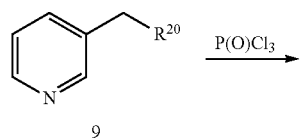

Monophosphate prodrugs VII can be prepared by reaction of 12 with phosphorous oxychloride to give 13 (Scheme 5). Nucleoside 1 can next be converted to monophosphate analog VII by reaction of the 5'-hydroxyl group with the chlorophosphoryl substrate, 13. Removal of protecting groups, if necessary, provides monophosphate prodrugs VII.

Scheme 5 A synthetic approach to monophosphate prodrugs VII.
(Base, $R^1$, $R^2$, $R^3$, $R^5$ and $R^{19}$ are as defined in active compound section).

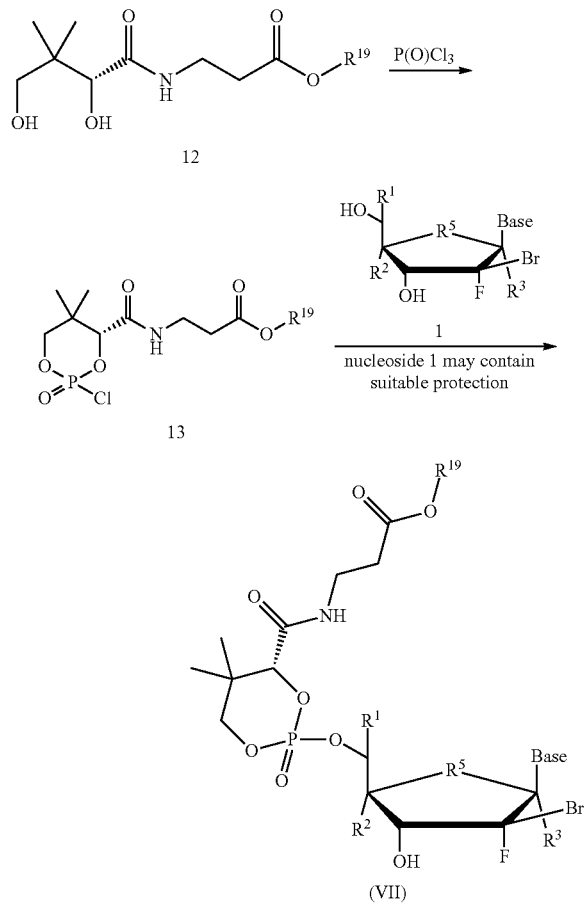

Monophosphate prodrugs VIII can be prepared by reaction of 14 with phosphorous oxychloride to give 15 (Scheme 6). Nucleoside 1 can next be converted to monophosphate analog VIII by reaction of the 5'-hydroxyl group with the chlorophosphoryl substrate, 15. Removal of protecting groups, if necessary, provides monophosphate prodrugs VIII.

Scheme 6 A synthetic approach to monophosphate prodrugs VIII.
(Base, $R^1$, $R^2$, $R^3$, $R^5$, and $R^{21}$ are as defined in active compound section).

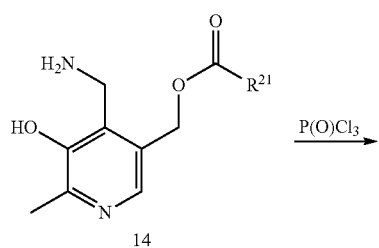

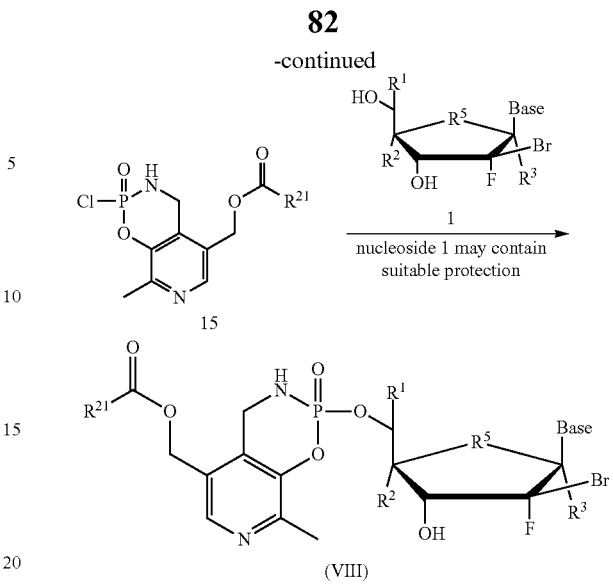

Incorporation of Deuterium:

It is expected that single or multiple replacement of hydrogen with deuterium (carbon-hydrogen bonds to carbon-deuterium bond) at site(s) of metabolism in the sugar portion of a nucleoside antiviral agent will slow down the rate of metabolism. This can provide a relatively longer half-life, and slower clearance from the body. The slow metabolism of a therapeutic nucleoside is expected to add extra advantage to a therapeutic candidate, while other physical or biochemical properties are not affected. Intracellular hydrolysis or deuterium exchanges my result in liberation of deuterium oxide ($D_2O$).

Methods for incorporating deuterium into amino acids, phenol, sugars, and bases, are well known to those of skill in the art. Representative methods are disclosed in U.S. Pat. No. 9,045,521.

A large variety of enzymatic and chemical methods have been developed for deuterium incorporation at both the sugar and nucleoside stages to provide high levels of deuterium incorporation (D/H ratio). The enzymatic method of deuterium exchange generally has low levels of incorporation. Enzymatic incorporation has further complications due to cumbersome isolation techniques which are required for isolation of deuterated mononucleotide blocks. Schmidt et al., Ann. Chem. 1974, 1856; Schmidt et al., Chem. Ber., 1968, 101, 590, describes synthesis of 5',5'-$^2H_2$-adenosine which was prepared from 2',3'-O-isopropylideneadenosine-5'-carboxylic acid or from methyl-2,3-isopropylidene-beta-D-ribofuranosiduronic acid, Dupre, M. and Gaudemer, A., Tetrahedron Lett. 1978, 2783. Kintanar, et al., Am. Chem. Soc. 1998, 110, 6367 reported that diastereoisomeric mixtures of 5'-deuterioadenosine and 5'(R/S)-deuteratedthymidine can be obtained with reduction of the appropriate 5'-aldehydes using sodium borodeuteride or lithium aluminum deuteride (98 atom % $^2H$ incorporation). Berger et al., Nucleoside & Nucleotides 1987, 6, 395 described the conversion of the 5'-aldehyde derivative of 2'deoxyguanosine to 5' or 4'-deuterio-2'-deoxyguanosine by heating the aldehyde in $^2H_2O$/pyridine mixture (1:1) followed by reduction of the aldehyde with $NaBD_4$.

Ajmera et al., Labelled Compd. 1986, 23, 963 described procedures to obtain 4'-deuterium labeled uridine and thymidine (98 atom % $^2H$). Sinhababu, et al., J. Am. Chem. Soc. 1985, 107, 7628) demonstrated deuterium incorporation at the C3' (97 atom % $^2H$) of adenosine during sugar synthesis upon stereoselective reduction of 1,2:5,6-di-O-isopropylidene-3-D-hexofuranos-3-ulose to 1,2:5,6-di-O-isopropylidene-3-deuterio-β-D-ribohexofuranose using sodium borodeuteride and subsequently proceeding further to the nucleoside synthesis. Robins, et al., Org. Chem. 1990, 55, 410 reported synthesis of more than 95% atom $^2$H incorporation at C3' of adenosine with virtually complete stereoselectivity upon reduction of the 2'-O-tert-butyldimethylsilyl (TBDMS) 3-ketonucleoside by sodium borodeuteride in acetic acid. David, S. and Eustache, J., Carbohyd. Res. 1971, 16, 46 and David, S. and Eustache, J., Carbohyd. Res. 1971, 20, 319 described syntheses of 2'-deoxy-2'(S)-deuterio-uridine and cytidine. The synthesis was carried out by the use of 1-methyl-2-deoxy-2'-(S)-deuterio ribofuranoside.

Radatus, et al., J. Am. Chem. Soc. 1971, 93, 3086 described chemical procedures for synthesizing 2'-monodeuterated (R or S)-2'-deoxycytidines. These structures were synthesized from selective 2-monodeuterated-2-deoxy-D-riboses, which were obtained upon stereospecific reduction of a 2,3-dehydro-hexopyranose with lithium aluminum deuteride and oxidation of the resulting glycal. Wong et al. J. Am. Chem. Soc. 1978, 100, 3548 reported obtaining deoxy-1-deuterio-D-erythro-pentose, 2-deoxy-2(S)-deuterio-D-erythro-pentose and 2-deoxy-1,2(S)-dideuterio-D-erythro-pentose from D-arabinose by a reaction sequence involving the formation and LiAlD$_4$ reduction of ketene dithioacetal derivatives.

Pathak et al. J., Tetrahedron 1986, 42, 5427) reported stereospecific synthesis of all eight 2' or 2'-deuterio-2'-deoxynucleosides by reductive opening of appropriate methyl 2,3-anhydro-beta-D-ribo or beta-D-lyxofuranosides with LiAlD$_4$. Wu et al. J. Tetrahedron 1987, 43, 2355 described the synthesis of all 2',2''-dideuterio-2'-deoxynucleosides, for both deoxy and ribonucleosides, starting with oxidation of C2' of sugar and subsequent reduction with NaBD$_4$ or LiAlD$_4$ followed by deoxygenation by tributyltin deuteride. Roy et al. J. Am. Chem. Soc. 1986, 108, 1675, reported 2',2'-dideuterio-2'-deoxyguanosine and thymidine can be prepared from 2-deoxyribose 5-phosphate using 2-deoxyribose 5-phosphate aldolase enzyme in $^2$H$_2$O achieving some 90 atom % deuteration. Similarly, the synthesis of 4',5',5'-$^2$H$_3$-guanosine can be carried out.

Therefore, it is clear that each position of the sugar residue can be selectively labeled.

A useful alternative method of stereospecific deuteration was developed to synthesize polydeuterated sugars. This method employed exchange of hydrogen with deuterium at the hydroxyl bearing carbon (i.e. methylene and methine protons of hydroxyl bearing carbon) using deuterated Raney nickel catalyst in $^2$H$_2$O.

Various techniques are available to synthesize fully deuterated deoxy and ribonucleosides. Thus in one method, exchange reaction of deuterated Raney nickel-$^2$H$_2$O with sugars, a number of deuterated nucleosides specifically labeled at 2', 3' and 4' positions were prepared. The procedure consisted of deuteration at 2', 3' and 4' positions of methyl beta-D-arabinopyranoside by Raney nickel-$^2$H$_2$O exchange reaction followed by reductive elimination of '2-hydroxyl group by tributyltin deuteride to give methyl beta-D-2',2',3',4'-$^2$H$_{4-2}$-deoxyribopyranoside, which was converted to methyl beta-D-2',2',3',4'-$^2$H$_4$-2'-deoxyribofuranoside and glycosylated to give various 2',2',3',4'-$^2$H$_4$-nucleosides (>97 atom % $^2$H incorporation for H3' & H4'.

The synthesis of deuterated phenols is described, for example, in Hoyer, H. (1950), Synthese des pan-Deutero-o-nitro-phenols. Chem. Ber., 83: 131-136. This chemistry can be adapted to prepare substituted phenols with deuterium labels. Deuterated phenols, and substituted analogs thereof, can be used, for example, to prepare phenoxy groups in phosphoramidate prodrugs.

The synthesis of deuterated amino acids is described, for example, in Matthews et al., Biochimica et Biophysica Acta (BBA)—General Subjects, Volume 497, Issue 1, 29 Mar. 1977, Pages 1-13. These and similar techniques can be used to prepare deuterated amino acids, which can be used to prepare phosphoramidate prodrugs of the nucleosides described herein.

One method for synthesizing a deuterated analog of the compounds described herein involves synthesizing a deuterated ribofuranoside with 2'-fluoro, 2'-chloro substitution; and attaching a nucleobase to the deuterated ribofuranoside to form a deuterated nucleoside. A prodrug, such as a phosphoramidate prodrug, can be formed by modifying the 5'-OH group on the nucleoside. Where a deuterated phenol and/or deuterated amino acid is used, one can prepare a deuterated phosphoramidate prodrug.

Another method involves synthesizing a ribofuranoside with 2'-fluoro, 2'-chloro substitution, and attaching a deuterated nucleobase to form a deuterated nucleoside. This method can optionally be performed using a deuterated furanoside to provide additional deuteration. As with the method described above, the nucleoside can be converted into a prodrug form, which prodrug form can optionally include additional deuteration.

A third method involves synthesizing a ribofuranoside with 2'-fluoro, 2'-chloro substitution, attaching a nucleobase to form a nucleoside, and converting the nucleoside to a phosphoramidate prodrug using one or both of a deuterated amino acid or phenol analog in the phosphoramidate synthesis.

Accordingly, using the techniques described above, one can provide one or more deuterium atoms in the sugar, base, and/or prodrug portion of the nucleoside compounds described herein.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

Anhydrous solvents were purchased from Aldrich Chemical Company, Inc. (Milwaukee, Wis.) and EMD Chemicals Inc. (Gibbstown, N.J.). Reagents were purchased from commercial sources. Unless noted otherwise, the materials used in the examples were obtained from readily available commercial suppliers or synthesized by standard methods known to one skilled in the art of chemical synthesis. Melting points (mp) were determined on an Electrothermal digit melting point apparatus and are uncorrected. $^1$H and $^{13}$C NMR spectra were taken on a Varian Unity Plus 400 spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were determined on a Micromass Platform LC spectrometer using electrospray techniques. Elemental analyses were performed by Atlantic Microlab Inc. (Norcross, Ga.). Analytic TLC was performed on Whatman LK6F silica gel plates, and preparative TLC on Whatman PK5F silica gel plates. Column chromatography was carried out on Silica Gel or via reverse-phase high performance liquid chromatography.

Example 1

Preparation of Nucleoside Analog 9

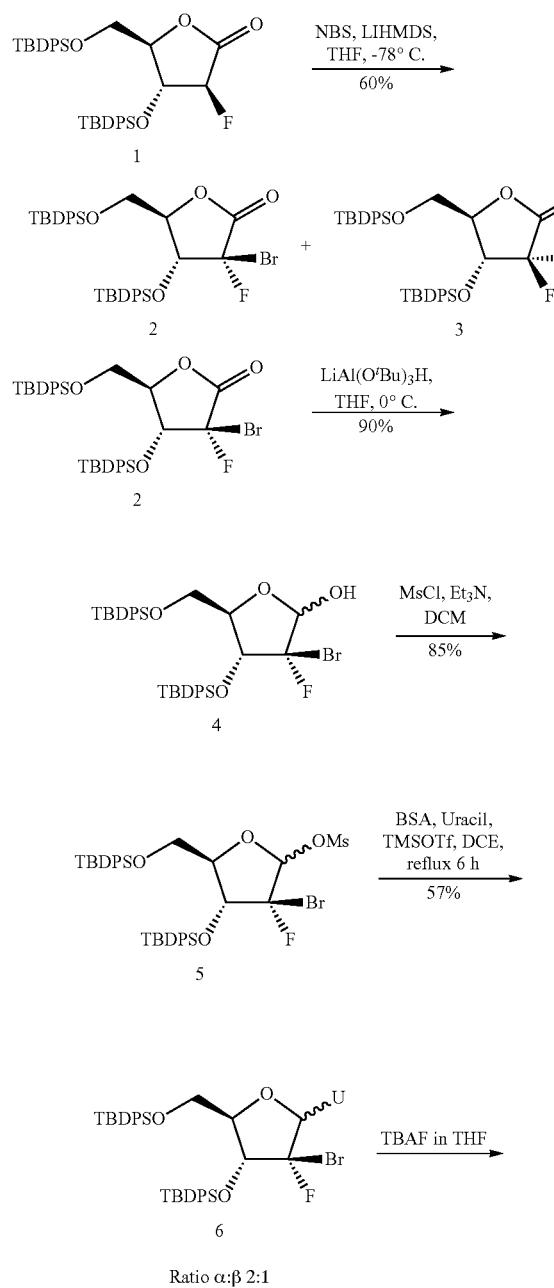

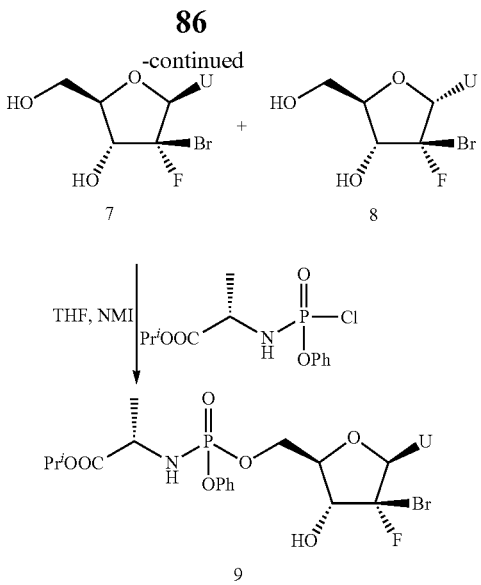

The techniques shown above in connection with Compounds 1-5 can be used to prepare other compounds described herein which include different bases than uracil. That is, Compound 5 is a common intermediate to a number of compounds described herein. Starting from Compounds 7 and/or 8, a variety of different prodrugs can be attached to the 5'-OH position. Further, analogs of Compound 5 can be prepared, with different functionality at the 1', 3', 4', and 5'-positions, and used as intermediates to prepare additional compounds.

EXPERIMENTAL

2-Deoxy-2-Bromo-2-Fluoro-3,5-di-O-(tert-butyldiphenylsilyl)-D-ribonolactone (2, 3)

To a flame dried round bottom flask were added 1 (5.6 g, 8.94 mmol) and NBS (3.18 g, 17.9 mmol) in 45 mL THF under an nitrogen atmosphere. The solution was cooled to −78° C., and a 1 M solution of LiHMDS in THF (14.31 mL, 14.31 mmol) was added dropwise. The reaction mixture was allowed to stir at −78° C. for 40 minutes and then quenched with a saturated NH$_4$Cl solution. The reaction mixture was allowed to warm to rt and the water layer was extracted with ethyl acetate (3×50 mL). The combined organic layer was washed with saturated NaHCO$_3$, water and finally brine, dried over Na$_2$CO$_3$, filtered and concentrated in vacuo. The $^{19}$F NMR of crude product showed roughly 1:1 diastereomeric mixture. The crude product was purified two times by flash chromatography using 0-1% EtOAc/hexane gradient to give 2 (1.82 g, 29% and 3 (1.94 g, 31%) as a white foam.

Compound 2: $^1$H NMR (CDCl$_3$, 400 MHz): δ 7.67-7.71 (m, 4H), 7.36-7.54 (m, 16H), 4.66 (m, 2H), 3.67 (m, 2H), 1.14 (s, 9H), 0.96 (s, 9H) $^{19}$F NMR (CD$_3$OD, 376 MHz): −135.92. LR-MS: calculated for C$_{21}$H$_{26}$BrFN$_3$O$_9$P 705.81, found 702.2, 704.4, 706.2.

Compound 3: $^1$H NMR (CDCl$_3$, 400 MHz): δ 7.63-7.69 (m, 4H), 7.32-7.50 (m, 16H), 4.54 (dd, J=15.3, 7.8 Hz) 4.24-4.26 (m, 1H), 3.72 (m, 1H), 3.47 (dd, J=12.7, 3.47 Hz) 1.14 (s, 9H), 0.87 (s, 9H) $^{19}$F NMR (CDCl$_3$, 376 MHz): −129.38 (d, J=14.45 Hz).

LR-MS: calculated for C$_{3-7}$H$_{42}$BrFO$_4$Si$_2$ 705.81, found 702.2, 704.4, 706.2.

2-Deoxy-2-Bromo-2-Fluoro-3,5-di-O-(tert-butyldiphenylsilyl)-D-ribofuranose (4)

Compound 2 (1.81 g, 2.57 mmol) was dissolved in THF (10 mL) and cooled to 0° C. To this solution was added a 1 M solution of LiAl(O$^t$Bu)$_3$H in THF (5.14 mL, 5.14 mmol). The reaction mixture was allowed to warm to rt. After two hours the reaction was quenched with saturated NH$_4$Cl at 0° C. The reaction mixture was filtered through a pad of silica gel and washed with ethyl acetate. The aqueous layer was extracted with ethyl acetate (3×25 mL), and the combined organic layer was washed with saturated NaHCO$_3$, water, and brine. The solution was dried over Na$_2$SO$_4$, filtered and concentrated in vacuo to give crude product 4 (1.63 g, 90%) as a anomeric mixture which was used directly in the next step.
$^{19}$F NMR (CDCl$_3$, 376 MHz): −131.4658 (dd, J=16.42, 5.65 Hz), −139.72.

1-Methylsulfonyl-2-Deoxy-2-Bromo-2-Fluoro-3,5-di-O-(tert-butyldiphenylsilyl)-D-ribofuranose (5)

Compound 4 (1.6 g, 2.26 mmol) was dissolved in CH$_2$Cl$_2$ (10 mL) and cooled to 0° C. To this solution was added triethyl amine (0.612 mL, 4.53 mmol) followed by methanesulfonyl chloride (0.263 mmol, 3.39 mmol). The reaction was stirred for 1 h toward rt. The reaction mixture was then diluted with CH$_2$Cl$_2$ (100 mL), washed with 1N HCl followed by 5% NaHCO$_3$ and brine. The organic layer was dried over Na$_2$SO$_4$, filtered and concentrated in vacuo to give crude product 5 (1.50 g, 85%) as a sticky solid. This anomeric mixture was used directly in the next step.
$^{19}$F NMR (CDCl$_3$, 376 MHz): −131.08 (s), 133.42 (dd, J=19.47, 7.72 Hz).

3,5-di-O-(tert-butyldiphenylsilyl)-2'-Deoxy-2'-Bromo-2'-Fluoro Uridine (6)

A solution of uracil (0.187 g, 1.67 mmol) and BSA (0.817 mL, 3.34 mmol) in 1,2-dichloroethane (1 mL) was stirred for 15 min at 60° C. The reaction was cooled to rt and compound 5 (0.655 g, 0.835 mmol) and TMSOTf (0.604 mL, 3.34 mmol) were added. The reaction vessel was heated in an oil bath at reflux for 6 h. The reaction was quenched by addition of 5% aqueous solution of NaHCO$_3$ (15 mL) at 0° C. The aqueous layer was extracted with ethyl acetate, and the combined organic layers were washed with a saturated solution of NaHCO$_3$, water, and brine. The solution was dried over Na$_2$SO$_4$, and concentrated in vacuo. The residue was purified by flash chromatography (using 0-1% EtOAc/hexane gradient to afford 6 (0.385 g, 57%) as a 2/1 α/β mixture.
$^{19}$F NMR (CDCl$_3$, 376 MHz): −120.2470 (t, J=15 Hz), 138.31 (t, J=16 Hz); LR-MS: calculated for C$_{41}$H$_{46}$BrFN$_2$O$_5$Si$_2$ 801.90, found 802.6, 825.4.

2'-Deoxy-2'-Bromo-2'-Fluoro Uridine (7, 8)

To a stirred solution of compound 6 (0.385 g, 0.48 mmol) in THF (2.5 mL), was added 1M solution of TBAF in THF (0.962 mL, 0.962 mmol). The reaction mixture was allowed to stir for 1 h. The solvent was evaporated and under reduced pressure and the residue was purified by flash chromatography using 0-6% MeOH/CH$_2$Cl$_2$ gradient to afford 7 (f-isomer, 28 mg, 18%) and 8 (α-isomer, 60 mg, 38%).
Compound 7 $^1$H NMR (CD$_3$OD, 400 MHz): δ 7.97 (d, J=8.2 Hz, 1H), 6.37 (d, J=16.2 Hz, 1H1'), 5.77 (d, J=8.2, 1H, H5), 4.45 (dd, J=20.2, 9.88 Hz, 1H, H3'), 3.99 (dd, J=12.6, 2.10 Hz, 1H, H5"), 3.94 (m, 1H, H4'), 3.81 (dd, J=12.7, 2.6 Hz); $^{19}$F NMR (CD$_3$OD, 376 MHz): −122.58; LR-MS: calculated for C$_9$H$_{10}$BrFN$_2$O$_5$ 325.09, found 327.

(2S)-isopropyl (((2R,3R,4S,5R)-4-bromo-5-(2,4-dioxo-3,4-dihydropyrimidin-1 (2H)-yl)-4-fluoro-3-hydroxytetrahydrofuran-2-yl)methoxy)(phenoxy)phosphoryl)-Propanoate (9)

To a stirred solution of 7 (21 mg, 0.064 mmol) and (2S)-isopropyl 2-((chloro(phenoxy)phosphoryl)amino)propanoate (39 mg, 0.13 mmol) in 1 mL of anhydrous THF under nitrogen atmosphere, was added 1-methylimidazole (10 μL, 0.13.0 mmol) slowly. After stirring for 2 h at 0° C., the reaction was stirred for 2 h toward rt. The reaction was quenched with isopropyl alcohol (0.2 mL). The solvent was removed under reduced pressure and the residue was purified by flash chromatography using 0-6% MeOH/CH$_2$Cl$_2$ to afford 8 (17 mg, 45%) as a diastereomeric (R$_p$/S$_p$) mixture.
$^1$H NMR (CD$_3$OD, 400 MHz): δ 7.58 (2d merged, J=8.2 Hz, 1H), 7.39 (m, 2H), 7.22-7.29 (m, 3H), 6.35 (2d merged, J=16.9 Hz, 1H), 5.66-5.73 (2d, J=8.2 Hz, 1H), 4.96-5.01 (m, 1H), 4.49-4.61 (m, 1H), 4.36-4.46 (m, 2H), 4.13-4.15 (m, 1H), 3.88-3.97 (m, 1H), 1.30-1.37 (m, 3H), 1.24 (m, 6H); $^{19}$F NMR (CD$_3$OD, 376 MHz): δ −122.08, −121.78; $^{31}$P NMR (CD$_3$OD, 162 MHz): δ 3.63. 3.54; LR-MS: calculated for C$_{21}$H$_{26}$BrFN$_3$O$_9$P 594.33, found 596.1.

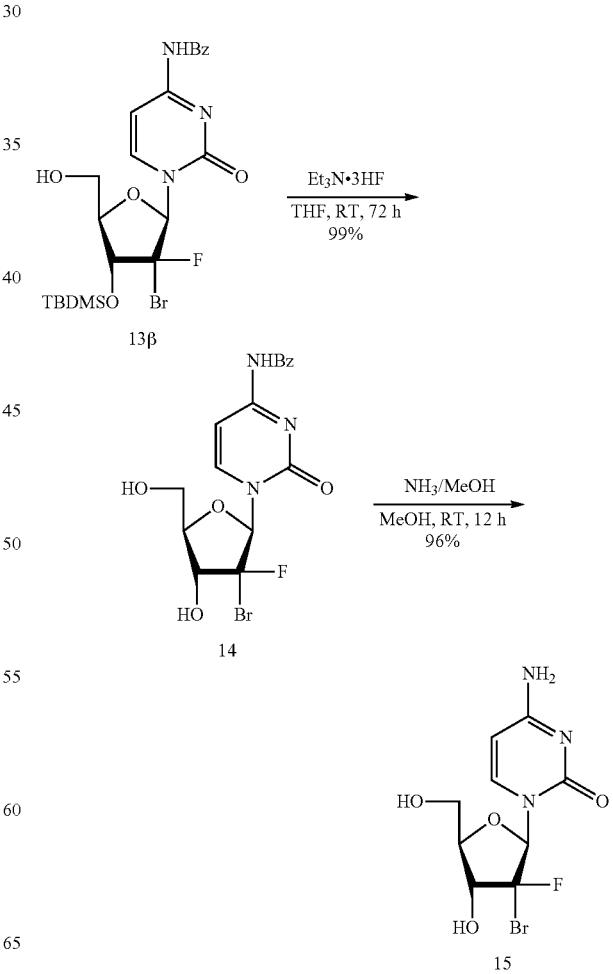

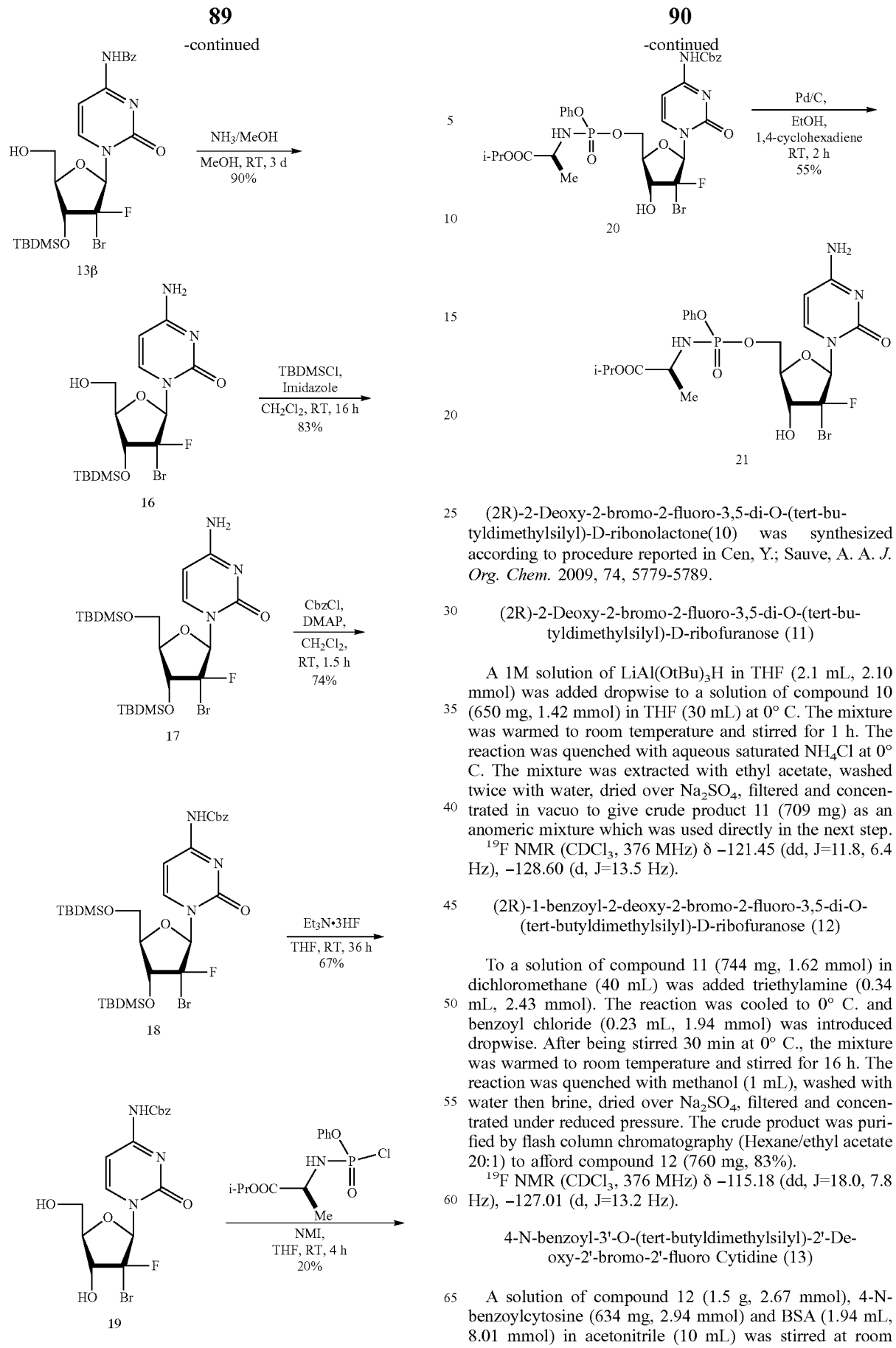

(2R)-2-Deoxy-2-bromo-2-fluoro-3,5-di-O-(tert-butyldimethylsilyl)-D-ribonolactone(10) was synthesized according to procedure reported in Cen, Y.; Sauve, A. A. *J. Org. Chem.* 2009, 74, 5779-5789.

(2R)-2-Deoxy-2-bromo-2-fluoro-3,5-di-O-(tert-butyldimethylsilyl)-D-ribofuranose (11)

A 1M solution of LiAl(OtBu)$_3$H in THF (2.1 mL, 2.10 mmol) was added dropwise to a solution of compound 10 (650 mg, 1.42 mmol) in THF (30 mL) at 0° C. The mixture was warmed to room temperature and stirred for 1 h. The reaction was quenched with aqueous saturated NH$_4$Cl at 0° C. The mixture was extracted with ethyl acetate, washed twice with water, dried over Na$_2$SO$_4$, filtered and concentrated in vacuo to give crude product 11 (709 mg) as an anomeric mixture which was used directly in the next step.
$^{19}$F NMR (CDCl$_3$, 376 MHz) δ −121.45 (dd, J=11.8, 6.4 Hz), −128.60 (d, J=13.5 Hz).

(2R)-1-benzoyl-2-deoxy-2-bromo-2-fluoro-3,5-di-O-(tert-butyldimethylsilyl)-D-ribofuranose (12)

To a solution of compound 11 (744 mg, 1.62 mmol) in dichloromethane (40 mL) was added triethylamine (0.34 mL, 2.43 mmol). The reaction was cooled to 0° C. and benzoyl chloride (0.23 mL, 1.94 mmol) was introduced dropwise. After being stirred 30 min at 0° C., the mixture was warmed to room temperature and stirred for 16 h. The reaction was quenched with methanol (1 mL), washed with water then brine, dried over Na$_2$SO$_4$, filtered and concentrated under reduced pressure. The crude product was purified by flash column chromatography (Hexane/ethyl acetate 20:1) to afford compound 12 (760 mg, 83%).
$^{19}$F NMR (CDCl$_3$, 376 MHz) δ −115.18 (dd, J=18.0, 7.8 Hz), −127.01 (d, J=13.2 Hz).

4-N-benzoyl-3'-O-(tert-butyldimethylsilyl)-2'-Deoxy-2'-bromo-2'-fluoro Cytidine (13)

A solution of compound 12 (1.5 g, 2.67 mmol), 4-N-benzoylcytosine (634 mg, 2.94 mmol) and BSA (1.94 mL, 8.01 mmol) in acetonitrile (10 mL) was stirred at room temperature for 15 min before introducing TMSOTf (1.45 mL, 8.01 mmol). The reaction vessel was then placed into the cavity of microwave reactor (CEM Discover), and irradiated for 12 min at 150° C. The reaction was quenched by addition of 5% aqueous solution of NaHCO$_3$ at 0° C. The aqueous layer was extracted with ethyl acetate, and the combined organic layers were washed with a saturated solution of NaHCO$_3$, water, and brine. The solution was dried over Na$_2$SO$_4$, and concentrated in vacuo. The residue was purified by flash column chromatography (hexanes/ethyl acetate 2:1) to afford 13α (300 mg) and 13β (200 mg).

Compound 13α: $^1$H NMR (CDCl$_3$, 400 MHz) δ (ppm) 8.91 (s, 1H), 7.94 (d, J=7.6 Hz, 2H), 7.90 (d, J=7.6 Hz, 1H), 7.70-7.47 (m, 4H), 6.75 (d, J=8.0 Hz, 1H), 4.65 (dd, J=13.5, 7.2 Hz, 1H), 4.25-4.18 (m, 1H), 4.01-3.71 (m, 2H), 2.78 (s, 1H), 0.96 (s, 9H), 0.21 (s, 3H), 0.20 (s, 3H). $^{19}$F NMR (CDCl$_3$, 376 MHz) δ −114.51 (s).

Compound 13β: $^1$H NMR (CDCl$_3$, 400 MHz) δ (ppm) 8.24 (d, J=7.5 Hz, 1H), 7.86 (d, J=7.5 Hz, 2H), 7.60 (ddd, J=6.9, 4.0, 1.2 Hz, 1H), 7.56-7.52 (m, 1H), 7.48 (dd, J=10.5, 4.8 Hz, 2H), 6.72 (d, J=5.6 Hz, 1H), 4.36 (dd, J=17.1, 7.6 Hz, 1H), 4.14-4.08 (m, 1H), 3.95 (dt, J=4.9, 2.2 Hz, 1H), 3.84 (dd, J=12.4, 2.8 Hz, 1H), 0.94 (s, 9H), 0.17 (s, 3H), 0.15 (s, 3H). $^{19}$F NMR (CDCl$_3$, 376 MHz) δ −121.28 (dd, J=12.0, 7.8 Hz). LR-MS: calculated for C$_{22}$H$_{29}$BrFN$_3$O$_5$Si 542.48, found 542.1, 544.1, 576.0, 578.0, 1185.3, 1187.3.

4-N-benzoyl-2'-Deoxy-2'-bromo-2'-fluoro Cytidine (14)

To a solution of compound 13P (40 mg, 0.074 mmol) in THF (8 mL) was added Et$_3$N.3HF (0.1 mL, 0.59 mmol). The reaction mixture was stirred for 72 h at 25° C. Then Et$_3$N (0.1 mL) was added to quench the reaction. After removal of the volatiles under reduced pressure, the crude product was purified using silica gel chromatography (CH$_2$Cl$_2$/MeOH 95:5) to afford compound 14 (32 mg, 99%).

$^1$H NMR (CD$_3$OD, 400 MHz) δ (ppm) 8.56 (d, J=7.6 Hz, 1H), 7.98 (d, J=6.8 Hz, 2H), 7.67-7.53 (m, 4H), 6.68 (d, J=5.6 Hz, 1H), 4.28 (dd, J=16.8, 7.6 Hz, 1H), 4.01-3.93 (m, 2H), 3.83 (dd, J=12, 0, 2.4 Hz, 1H). $^{19}$F NMR (CD$_3$OD, 376 MHz) δ −123.50 (d, J=18.4 Hz). LR-MS: calculated for C$_{16}$H$_{15}$BrFN$_3$O$_5$ 428.21, found 428.0, 430.0, 857.0, 859.0.

2'-Deoxy-2'-bromo-2'-fluoro Cytidine (15)

To a solution of compound 14 (32 mg, 0.074 mmol) in MeOH (6 mL) was added saturated NH$_3$ in MeOH (2 mL). The reaction mixture was stirred for 12 h at 25° C. After the solvent was removed under reduced pressure, the crude product was purified using silica gel chromatography (CH$_2$Cl$_2$/MeOH 3:1) to afford nucleoside 15 (23 mg, 96%).

$^1$H NMR (CD$_3$OD, 400 MHz) δ (ppm) 7.96 (dd, J=7.6, 1.8 Hz, 1H), 6.60 (d, J=8.2 Hz, 1H), 5.90 (d, J=7.6 Hz, 1H), 4.20 (dd, J=17.6, 7.2 Hz, 1H), 3.96-3.89 (m, 1H), 3.89-3.84 (m, 1H), 3.78 (dd, J=12.4, 3.3 Hz, 1H). $^{19}$F NMR (CD$_3$OD, 376 MHz) δ −123.82−−124.18 (m). LR-MS: calculated for C$_9$H$_{11}$BrFN$_3$O$_4$ 324.11, found 325.9, 648.8.

3'-O-(tert-butyldimethylsilyl)-2'-Deoxy-2'-bromo-2'-fluoro Cytidine (16)

To a solution of compound 13β (140 mg, 0.26 mmol) in methanol (24 mL) was added saturated NH$_3$ in MeOH (8 mL). After 3 days at room temperature, the mixture was concentrated in vacuo to give compound 16 (103 mg, 90%). The crude material was used without further purification in the next step.

$^1$H NMR (CD$_3$OD, 400 MHz) δ (ppm) 8.00 (dd, J=7.6, 1.4 Hz, 1H), 6.63 (d, J=6.2 Hz, 1H), 5.91 (d, J=7.6 Hz, 1H), 4.36 (dd, J=17.1, 7.4 Hz, 1H), 3.98-3.90 (m, 1H), 3.89-3.82 (m, 1H), 3.73 (dd, J=12.5, 2.9 Hz, 1H), 0.98-0.95 (m, 9H), 0.19 (d, J=2.9 Hz, 3H), 0.18 (s, 3H). $^{19}$F NMR (CD$_3$OD, 376 MHz) δ −123.10 (d, J=11.1 Hz). LR-MS: calculated for C$_{1-5}$H$_{25}$BrFN$_3$O$_4$Si 438.37, found 438.0, 440.0, 877.1, 879.1.

3',5'-di-O-(tert-butyldimethylsilyl)-2'-Deoxy-2'-bromo-2'-fluoro Cytidine (17)

Imidazole (18 mg, 0.26 mmol) was added to a mixture of compound 16 (26 mg, 0.086 mmol) and TBDMSCl (26 mg, 0.17 mmol) in dichloromethane (4 mL). The mixture was stirred overnight at 25° C., quenched with water and the crude mixture was extracted with ethyl acetate. The organic layer was washed with a saturated aqueous solution of NH$_4$Cl, dried over Na$_2$SO$_4$, filtrated and concentrated under reduced pressure. The crude product was purified by flash column chromatography using CH$_2$Cl$_2$/MeOH (10:1) to afford compound 17 (27 mg, 83%).

$^1$H NMR (CDCl$_3$, 400 MHz) δ (ppm) 7.75 (dd, J=7.5, 1.0 Hz, 1H), 6.69 (d, J=5.7 Hz, 1H), 5.72 (d, J=7.5 Hz, 1H), 4.23 (dd, J=16.8, 7.5 Hz, 1H), 3.97 (dt, J=11.6, 2.6 Hz, 1H), 3.83 (dd, J=7.5, 2.3 Hz, 1H), 3.78 (dd, J=11.7, 2.2 Hz, 1H), 0.93 (s, 9H), 0.92 (s, 9H), 0.16 (s, 3H), 0.11 (s, 9H). $^{19}$F NMR (CDCl$_3$, 376 MHz) δ −121.70 (dd, J=16.9, 4.6 Hz). 13C NMR (CDCl$_3$, 101 MHz) δ 165.98 (s), 155.80 (s), 141.02 (s), 112.36 (s), 109.65 (s), 95.12 (s), 89.34 (d, J=19.0 Hz), 81.23 (s), 73.50 (d, J=25.3 Hz), 60.34 (s), 26.14 (s), 25.84 (s), 18.60 (s), 18.25 (s), −4.12 (s), −4.71 (s), −5.19 (s), −5.26 (s).

4-N-carboxybenzyl-3',5'-di-O-(tert-butyldimethylsilyl)-2'-Deoxy-2'-bromo-2'-fluoro Cytidine (18)

To a solution of compound 17 (27 mg, 0.049 mmol) and benzyl chloroformate (21 μL, 0.15 mmol) in dichloromethane (5 mL) was added DMAP (36 mg, 0.29 mmol). The reaction was stirred at room temperature for 1.5 h, quenched with water and extracted with ethyl acetate. The organic layer was washed with HCl 1N, NaHCO$_3$ sat., brine, dried over Na$_2$SO$_4$, filtrated and concentrated under reduced pressure. The crude product was purified by flash chromatography (hexane/ethyl acetate 1:1) to afford compound 18 (25 mg, 74%).

$^1$H NMR (CDCl$_3$, 400 MHz) δ (ppm) 8.18 (d, J=7.6 Hz, 1H), 7.75 (s, 1H), 7.37 (brs, 5H), 7.22 (d, J=7.6 Hz, 1H), 6.72 (d, J=4.5 Hz, 1H), 5.22 (brs, 2H), 4.26 (dd, J=16.6, 7.8 Hz, 1H), 4.02 (d, J=11.8 Hz, 1H), 3.90 (d, J=7.7 Hz, 1H), 3.81 (dd, J=11.8, 1.9 Hz, 1H), 0.96 (s, 9H), 0.93 (s, 9H), 0.16 (s, 3H), 0.14 (s, 3H), 0.13 (s, 3H), 0.11 (s, 3H). $^{19}$F NMR (CDCl$_3$, 376 MHz) δ −122.22 (d, J=16.6 Hz).

4-N-carboxybenzyl-2'-Deoxy-2'-bromo-2'-fluoro Cytidine (19)

To a solution of compound 18 (25 mg, 0.036 mmol) in THF (4 mL) was added Et$_3$N.3HF (0.06 mL, 0.36 mmol). The reaction mixture was stirred for 36 h at 25° C. then Et$_3$N (0.06 mL) was added to quench the reaction. After removal of the volatiles under reduced pressure, the crude product was purified using silica gel chromatography ($CH_2Cl_2$/MeOH 10:1) to afford compound 19 (11 mg, 67%).

$^1$H NMR ($CD_3OD$, 400 MHz) δ (ppm) 8.44 (dd, J=7.7, 1.1 Hz, 1H), 7.50-7.26 (m, 6H), 6.64 (d, J=6.2 Hz, 1H), 5.23 (s, 2H), 4.25 (dd, J=17.2, 7.6 Hz, 1H), 3.98-3.91 (m, 2H), 3.81 (dd, J=12.5, 2.9 Hz, 1H). $^{19}$F NMR ($CD_3OD$, 376 MHz) δ -124.35 (dd, J=17.0, 4.8 Hz). LR-MS: calculated for $C_{17}H_{17}BrFN_3O_6$ 458.24, found 458.0, 460.0, 917.0, 919.0.

Isopropyl (((((2R,3R,4R,5R)-5-(4-(((benzyloxy)carbonyl)amino)-2-oxopyrimidin-1(2H)-yl)-4-bromo-4-fluoro-3-hydroxytetrahydrofuran-2-yl)methoxy)(phenoxy)phosphoryl)-L-alaninate (20)

To a solution of compound 19 (35 mg, 0.076 mmol) in THF (3 mL) was added NMI (30 μL, 0.38 mmol) then (2S)-isopropyl 2-((chloro(phenoxy)phosphoryl)amino)propanoate (70 mg, 0.23 mmol) in THF (0.23 mL). The mixture was stirred at rt for 4 h, quenched with water and extracted with ethyl acetate. The organic layer was washed with water twice, dried over $Na_2SO_4$, filtrated and concentrated under reduced pressure. The crude product was purified by flash chromatography ($CH_2Cl_2$/MeOH 20:1) to afford compound 20 (11 mg, 20%).

$^1$H NMR ($CD_3OD$, 400 MHz) δ (ppm) 8.00 (ddd, J=43.8, 7.7, 1.8 Hz, 1H), 7.47-7.15 (m, 11H), 6.65 (dd, J=9.0 Hz, 1H), 5.24 (s, 2H), 5.04-4.94 (m, 1H), 4.59-4.35 (m, 2H), 4.26-4.19 (m, 1H), 4.16-4.12 (m, 1H), 3.97-3.86 (m, 1H), 1.38-1.31 (m, 3H), 1.22 (dd, J=6.2, 2.1 Hz, 6H). $^{19}$F NMR ($CD_3OD$, 376 MHz) δ -124.22--124.67 (m). $^{31}$P NMR ($CD_3OD$, 162 MHz) δ 3.66 (d, J=13.5 Hz). LR-MS: calculated for $C_{29}H_{33}BrFN_4O_{10}P$ 727.48, found 729.1, 730.4, 1129.0.

Isopropyl (((((2R,3R,4R,5R)-5-(4-amino-2-oxopyrimidin-1(2H)-yl)-4-bromo-4-fluoro-3-hydroxytetrahydrofuran-2-yl)methoxy)(phenoxy)phosphoryl)-L-alaninate (21)

To a round bottom flask charged with compound 20 (23 mg, 0.032 mmol) in ethanol (2 mL) was added 1,4-cyclohexadiene (0.1 mL, 0.70 mmol) and Pd/C (10 mg, 0.01 mmol). After 2 h at 25° C., the mixture was filtrated on a celite pad and the filtrate was then concentrated under reduced pressure. Purification by flash column chromatography ($CH_2Cl_2$/MeOH 10:1) gave nucleotide 21 in 55% yield (13 mg).

$^1$H NMR ($CD_3OD$, 400 MHz) δ (ppm) 7.61 (ddd, J=28.8, 7.6, 2.3 Hz, 1H), 7.40-7.34 (m, 2H), 7.27-7.20 (m, 3H), 6.61 (dd, J=11.2, 8.4 Hz, 1H), 5.86 (dd, J=12.0, 7.6 Hz, 1H), 5.04-4.95 (m, 1H), 4.54-4.31 (m, 2H), 4.19 (ddd, J=17.5, 6.5, 2.0 Hz, 1H), 4.10 (brs, 1H), 3.93-3.88 (m, 1H), 1.37-1.31 (m, 3H), 1.29 (brs, 2H), 1.25-1.20 (m, 4H). $^{19}$F NMR ($CD_3OD$, 376 MHz) δ -124.36--124.53 (m). $^{31}$P NMR ($CD_3OD$, 162 MHz) δ 3.57 (d, J=11.7 Hz). LR-MS: calculated for $C_{21}H_{27}BrFN_4O_8P$ 593.34, found 595.1, 597.0, 1187.4.

Example 2

Cellular Toxicity Assays

The toxicity of the compounds was assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67).

Cycloheximide was included as positive cytotoxic control, and untreated cells exposed to solvent were included as negative controls. The cytotoxicity $IC_{50}$ was obtained from the concentration-response curve using the median effective method described previously (see Chou T.-C. & Talalay P. *Adv. Enzyme Regul.* 1984, 22, 27-55; Belen'kii M. S. & Schinazi R. F. Antiviral Res. 1994, 25, 1-11). The results are shown in Table 2 below:

TABLE 2

Cytotoxicity, $CC_{50}$, μM (% inhibition)

PBM > 100 μM (-24%)
CEM > 100 μM (21%)
Vero > 100 μM (4.2%)

7

PBM > 100 μM (-3.8%)
CEM > 100 μM (14%)
Vero > 100 μM (2.6%)

9

Mitochondrial Toxicity Assays in HepG2 Cells:
i) Effect of Compounds on Cell Growth and Lactic Acid Production:
The effect on the growth of HepG2 cells was determined by incubating cells in the presence of 0 μM, 0.1 μM, 1 μM, 10 μM and 100 μM drug. Cells ($5 \times 10^4$ per well) were plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number was determined using a hemocytometer. Also taught by Pan-Zhou X-R, Cui L, Zhou X-J, Sommadossi J-P, Darley-Usmer VM. "Differential effects of antiretroviral nucleoside analogs on mitochondrial function in HepG2 cells," Antimicrob. Agents Chemother. 2000; 44: 496-503.

To measure the effects of the compounds on lactic acid production, HepG2 cells from a stock culture were diluted and plated in 12-well culture plates at $2.5 \times 10^4$ cells per well. Various concentrations (0 μM, 0.1 μM, 1 μM, 10 μM and 100 μM) of compound were added, and the cultures were incubated at 37° C. in a humidified 5% $CO_2$ atmosphere for 4 days. At day 4, the number of cells in each well was determined and the culture medium collected. The culture medium was then filtered, and the lactic acid content in the medium was determined using a colorimetric lactic acid assay (Sigma-Aldrich). Since lactic acid product can be considered a marker for impaired mitochondrial function, elevated levels of lactic acid production detected in cells grown in the presence of test compounds would indicate a drug-induced cytotoxic effect.

ii) Effect on Compounds on Mitochondrial DNA Synthesis:

a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay was used reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug indicated mitochondrial toxicity.

The effect of compounds 7 and 9 on the levels of mitochondrial and nuclear DNA, and lactic acid production was evaluated in HepG2 cells (14-day assay), and the data is tabulated below in Table 3:

TABLE 3

| Compound | [ ], µM | % inhibition MitDNA/nDNA | $IC_{50}$, µM MitDNA/nDNA | MitDNA Content (% of control) | Lactic acid Production (% of control) | Summary |
|---|---|---|---|---|---|---|
| Untreated control | | 0/0 | | 100 (93-107) | 100 ± 3.4 | |
| 7 | 10 | <1/4.4 | >50/>50 | 117 (98-138) | 85.0 ± 16.3 | not toxic |
| | 50 | 13.5/<1 | | 72 (63-83) | 69.0 ± 13.5 | |
| 9 | 10 | <1/5.2 | >10/>10 | 187 (169-206) | 89.5 ± 2.0 | not toxic up to 10 µM |
| | 50 | 67.8/49.8 | <50/≥50 | 64 (45-91) | 111 ± 38.5 | |
| SOVALDI* (sofosbuvir)[1] | 1 | −12/−98 | 36/38 | 57 (35-93) | | Slightly toxic |
| | 10 | −18/−51 | | 78 (69-89) | | |
| | 50 | 87/93 | | 200 (136-278) | | |
| 3TC (control) | 10 | 33.3/26.8 | >10/>10 | 91 (90-92) | 94.9 ± 12.2 | not toxic |
| ddc (control) | 10 | 99.9/88.7 | <10/<10 | 0.5 (0.4-0.5) | 267 ± 25.2 | toxic |

[1]Sofosbuvir data generated in a separate experiment in all studies described in this application that determine the effect of compounds on mitochondrial DNA content. In this assay, low-passage-number HepG2 cells were seeded at 5,000 cells/well in collagen-coated 96-well plates. Test compounds were added to the medium to obtain final concentrations of 0 µM, 0.1 µM, 10 µM and 100 µM. On culture day 7, cellular nucleic acids were prepared by using commercially available columns (RNeasy 96 kit; Qiagen). These kits co-purify RNA and DNA, and hence, total nucleic acids are eluted from the columns. The mitochondrial cytochrome c oxidase subunit II (COXII) gene and the ß-actin or rRNA gene were amplified from 5 µl of the eluted nucleic acids using a multiplex Q-PCR protocol with suitable primers and probes for both target and reference amplifications. For COXII the following sense, probe and antisense primers were used, respectively: 5'-TGCCCGCCATCATCCTA-3' (SEQ ID NO. 1), 5'-tetrachloro-6-carboxyfluorescein-TCCTCATCGCCCTC-CCATCCC-TAMRA-3' (SEQ ID NO. 2) and 5'-CGTCTGT-TATGTAAAGGATGCGT-3' (SEQ ID NO. 3). For exon 3 of the ß-actin gene (GenBank accession number E01094) the sense, probe, and antisense primers are 5'-GCGCGGCTA-CAGCTTCA-3' (SEQ ID NO. 4), 5'-6-FAMCACCACGGC-CGAGCGGGATAMRA-3' (SEQ ID NO. 5) and 5'-TCTC-CTTAATGTCACGCACGAT-3' (SEQ ID NO. 6), respectively. The primers and probes for the rRNA gene are commercially available from Applied Biosystems. Since equal amplification efficiencies are obtained for all genes, the comparative CT method was used to investigate potential inhibition of mitochondrial DNA synthesis. The comparative CT method uses arithmetic formulas in which the amount of target (COXII gene) is normalized to the amount of an endogenous reference (the B-actin or rRNA gene) and is relative to a calibrator (a control with no drug at day 7). The arithmetic formula for this approach is given by 2-ΔΔCT, where ΔΔCT is (CT for average target test sample−CT for target control)−(CT for average reference test−CT for The data show that compounds 7 and 9, as described herein, are non-toxic up to 10 µM and are less toxic than Sofosbuvir.

Example 4

Mitochondrial Toxicity-Glu/Gal

Protocol Summary

HepG2 cells are plated on 96 or 384 well tissue culture polystyrene plates. After 24 hr the cells are dosed with test compound at a range of concentrations and incubated for 72 hr in medium supplemented with either galactose or glucose. Test compounds are said to cause mitochondrial toxicity if the cells grown in galactose-containing medium are more sensitive to the test compound than the cells grown in glucose-containing medium.

Objective:

To measure the sensitivity of HepG2 cells grown in medium containing either galactose or glucose to the test compound.

Experimental Procedure

HepG2 human hepatocellular carcinoma cells are plated on 96 or 384-well tissue culture polystyrene plates containing either galactose or glucose containing medium supplemented with 10% fetal bovine serum and antibiotics and incubated overnight. The cells are dosed with increasing concentrations of the test compound (final DMSO concentration 0.5%; typical final test compound concentrations of 100, 30, 10, 3, 1, 0.3, 0.1, 0.03 µM for an eight point dose response curve; n=3 replicates per concentration) and the cells are incubated for 72 hr. Appropriate controls are simultaneously used as quality controls. Cell viability is measured using Hoechst staining and cell counting by a HCS reader.

Data Analysis

The vehicle control wells are used to determine significance limits. $AC_{50}$ values are determined provided a clear dose-response relationship is observed.

Figure 3A:
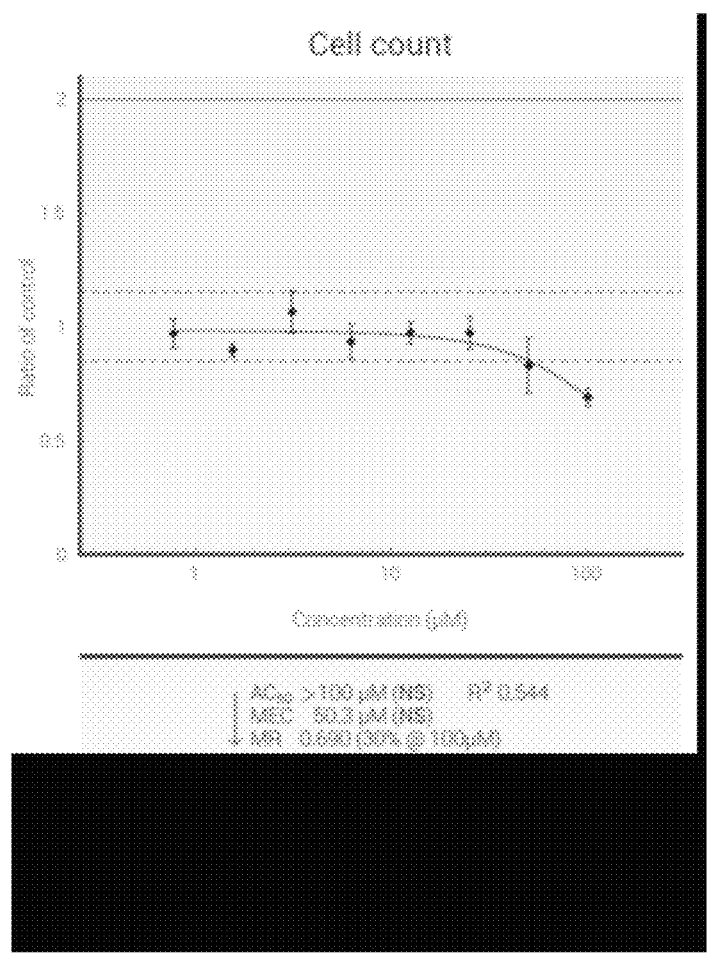
FIGS. 3a and 3b are charts showing the results for a 3 day assessment of the mitochondrial toxicity of nucleoside prodrug 9, showing cell count as a function of the ratio of control and glucose (FIG. 3a) and galactose (FIG. 3b) concentrations (µM).
Figure 3B:
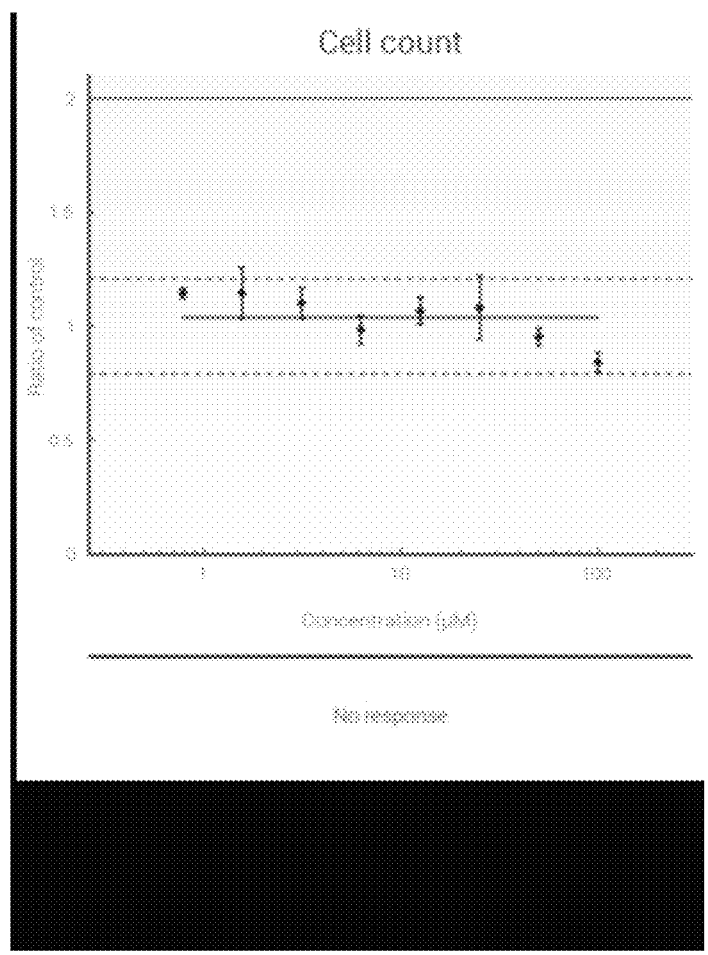
Figure 3C:
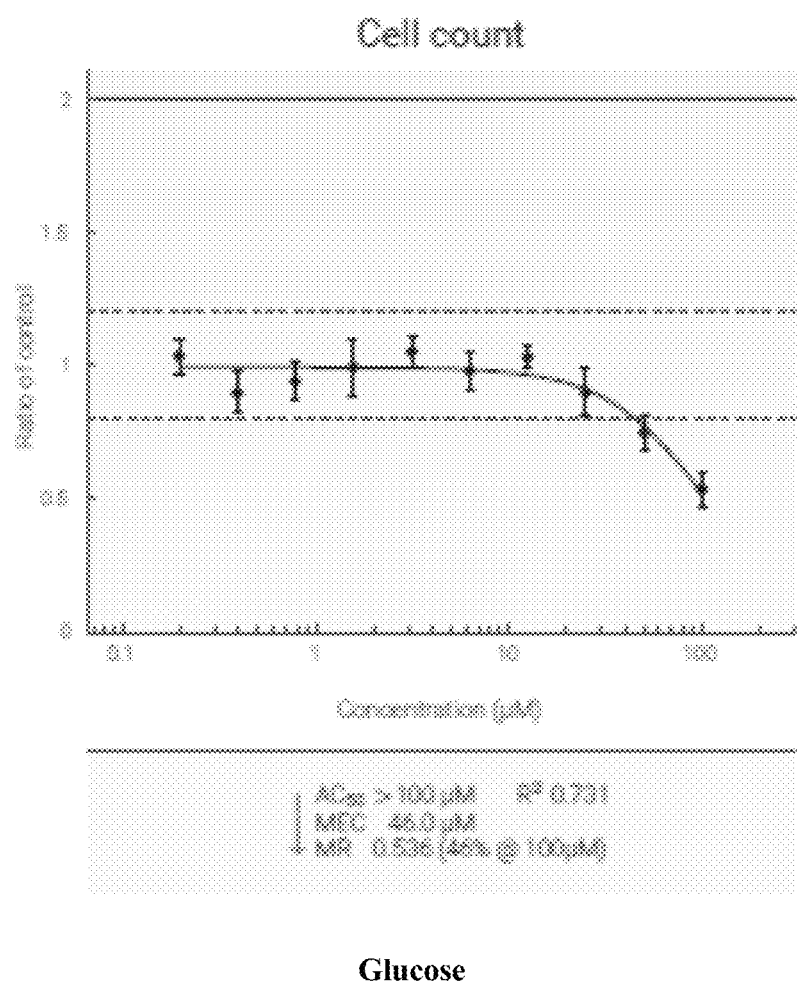
FIGS. 3c and 3d are charts showing the results for a 3 day assessment of the mitochondrial toxicity of nucleoside prodrug 23, showing cell count as a function of the ratio of control and glucose (FIG. 3a) and galactose (FIG. 3b) concentrations (µM).
Figure 3D:
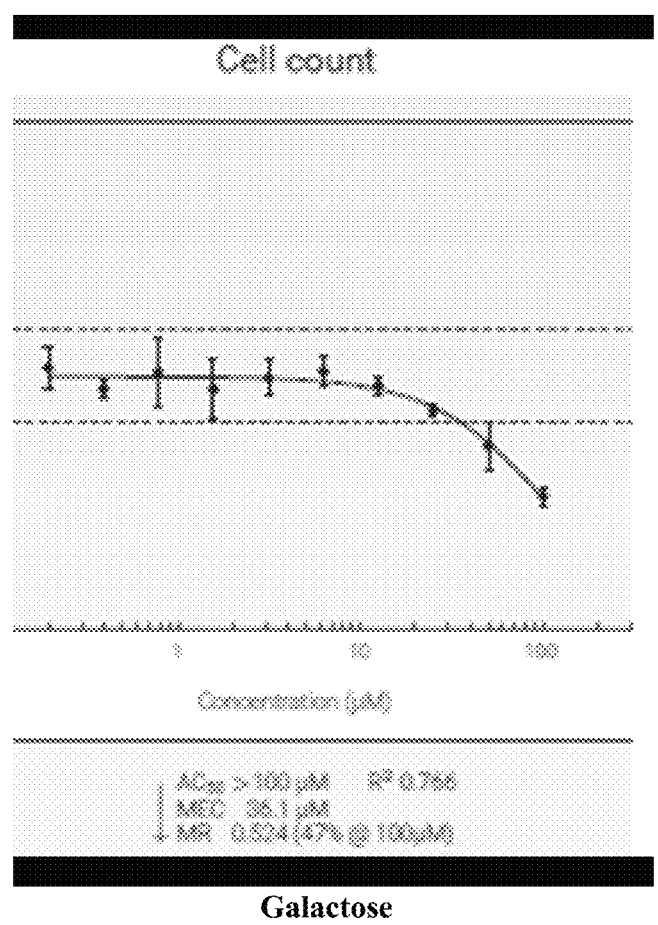
Figure 3E:
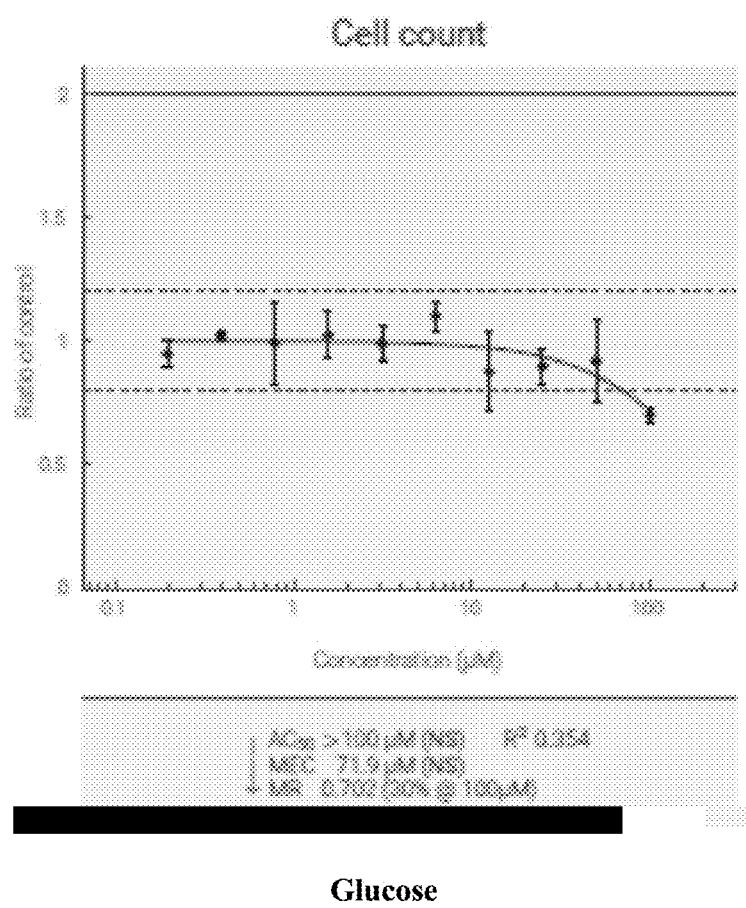
FIGS. 3e and 3f are charts showing the results for a 3 day assessment of the mitochondrial toxicity of nucleoside prodrug 22, showing cell count as a function of the ratio of control and glucose (FIG. 3a) and galactose (FIG. 3b) concentrations (µM).
Figure 3F:
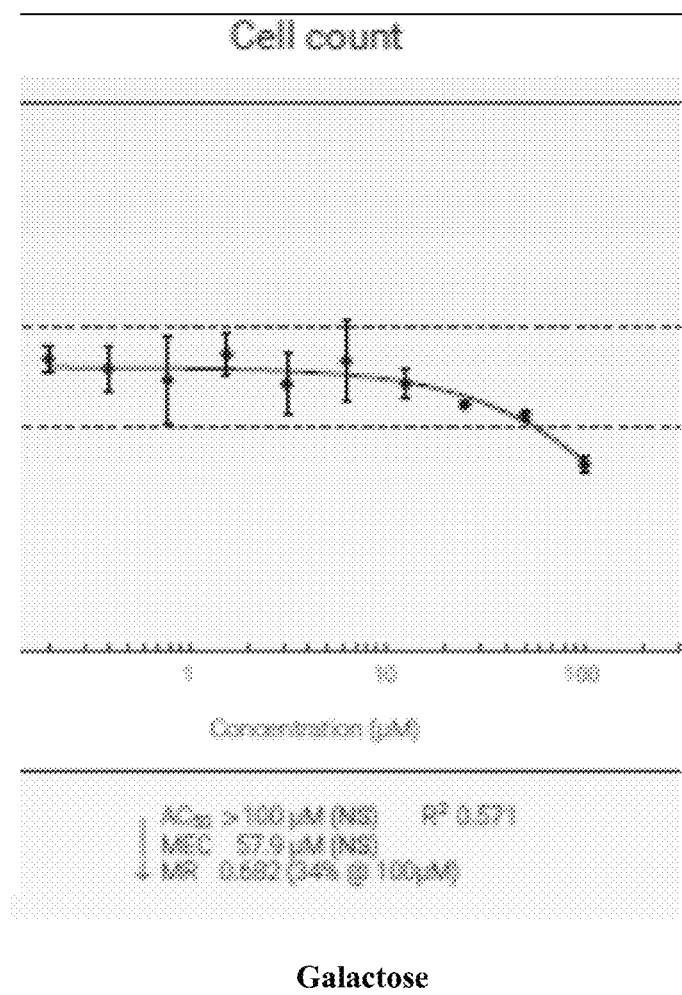

The effect of nucleoside prodrug 9 on cell count in HepG2 cells and results for mitochondrial toxicity Glu/Gal (3-day assay) is shown in FIGS. 3a-b below. FIGS. 3c-e show the Glu/Gal mitochondrial toxicity data for the single phosphorous diastereomers 23 and 22. The structures for these compounds are shown below:

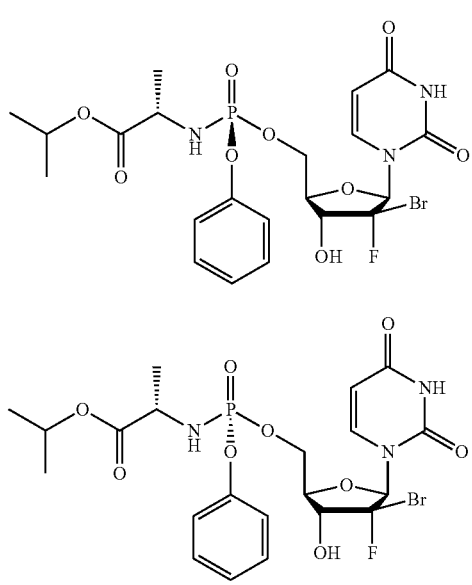

Example 5

Mitochondrial Toxicity Assays in Neuro2A Cells

To estimate the potential of the compounds of this invention to cause neuronal toxicity, mouse Neuro2A cells (American Type Culture Collection 131) can be used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. *Antimicrob. Agents Chemother.* 2005, 49, 1994-2001). The concentrations necessary to inhibit cell growth by 50% (CC50) can be measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug can be carried out as described above. ddC and AZT can be used as control nucleoside analogs.

Example 6

Assay for Bone Marrow Cytotoxicity

Primary human bone marrow mononuclear cells can be obtained commercially from Cambrex Bioscience (Walkersville, Md.). CFU-GM assays is carried out using a bilayer soft agar in the presence of 50 units/mL human recombinant granulocyte/macrophage colony-stimulating factor, while BFU-E assays used a ethylcellulose matrix containing 1 unit/mL erythropoietin (see Sommadossi J P, Carlisle R. Toxicity of 3'-azido-3'-deoxythymidine and 9-(1,3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of cytotoxicity of the (−) and (+) enantiomer of 2',3'-dideoxy-3'-thiacytidine in normal human bone marrow progenitor cells. Biochem. Pharmacol. 1992; 44:1921-1925). Each experiment can be performed in duplicate in cells from three different donors. AZT is used as a positive control. Cells can be incubated in the presence of the compound for 14-18 days at 37° C. with 5% $CO_2$, and colonies of greater than 50 cells can be counted using an inverted microscope to determine the $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples. The Bone Marrow Cytotoxicity results for compounds 7 and 9 are shown in Table 4.

TABLE 4

| | Bone marrow toxicity, $CC_{50}$, µM | |
|---|---|---|
| organization | 9 | 7 |
| LOBP | >100 | >100 |
| Stem cell | >100 | NA |

Example 7

HCV Replicon Assay[1]

Huh 7 Clone B cells containing HCV Replicon RNA were seeded in a 96-well plate at 5000 cells/well, and the compounds tested at 10 µM in triplicate immediately after seeding. Following five days incubation (37° C., 5% $CO_2$), total cellular RNA was isolated by using versaGene RNA purification kit from Gentra. Replicon RNA and an internal control (TaqMan rRNA control reagents, Applied Biosystems) were amplified in a single step multiplex Real Time RT-PCR Assay. The antiviral effectiveness of the compounds was calculated by subtracting the threshold RT-PCR cycle of the test compound from the threshold RT-PCR cycle of the no-drug control (ΔCt HCV). A ΔCt of 3.3 equals a 1-log reduction (equal to 90% less starting material) in Replicon RNA levels. The cytotoxicity of the compounds was also calculated by using the ΔCt rRNA values. 2'-C-Me-C was used as the positive control. To determine $EC_{90}$ and $IC_{50}$ values[2], ΔCt: values were first converted into fraction of starting material[3] and then were used to calculate the % inhibition.

REFERENCES

1. Stuyver L et al., Ribonucleoside analogue that blocks replication or bovine viral diarrhea and hepatitis C viruses in culture. Antimicrob. Agents Chemother. 2003, 47, 244-254.

2. Reed I J & Muench H, A simple method or estimating fifty percent endpoints. Am. J. Hyg. 27: 497, 1938.

3. Applied Biosystems Handbook

The Median Effective Concentrations ($EC_{50}$) ranges of compounds 7, 9, 15, 21, 22 and 23 against HCV 1b are shown in Table 5:

TABLE 5

| Drug | EC$_{50}$ (μM or letter value) | EC$_{90}$ (μM or letter value) or % inhib HCV | CC$_{50}$ or % inhibit cytotoxicity |
| --- | --- | --- | --- |
| Compound 7 (parent nucleoside) | A | | >10 |
| Compound 9 (prodrug) | C | | >10 |
| Compound 15 (parent nucleoside) | | 99.9% @ 10 μM | 67.9% @ 10 μM |
| Compound 21 (prodrug) | 67.9% @ 10 μM | | |
| Compound 22 | C | B | |
| Compound 23 | C | C | |
| Sofosbuvir | 0.2 | 0.8 | |

A = >10 μM
B = 1-10 μM
C = 0.1-1 μM
D = <0.1 μM

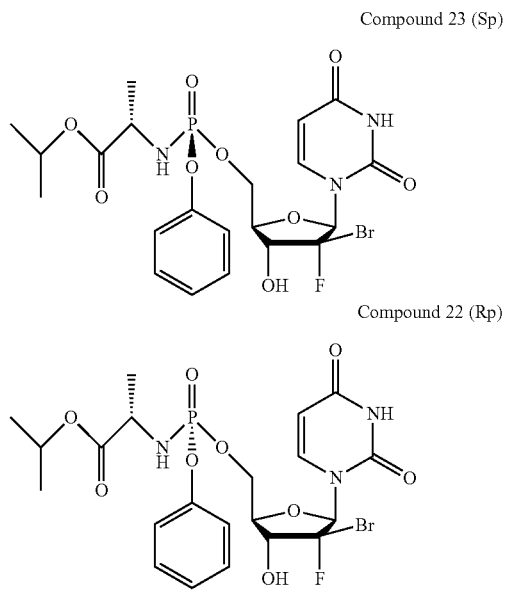

Compound 23 (Sp)

Compound 22 (Rp)

Structures for Compounds 7, 9, 15, and 21 shown elsewhere herein.

Example 8

IC$_{50}$ in HepaRG Cells for a 14-Day Assay (Non-Proliferating Liver Cells) Using Cell Titer GLO HepaRG cells are plated one week prior to dosing to allow for the cells to regain its maximal metabolic activity and structure. HepaRG cells are dosed with increasing concentrations of the test compound (final DMSO concentration=0.5%); final test compound concentrations of 100, 30, 10, 3, 1, 0.3, 0.1, 0.03 μM for an eight point dose response curve (n=3 replicates per concentration) and the microtissues are incubated for 14 days with 4 repeat doses. Appropriate controls are simultaneously used as quality controls. Following the dosing period the medium is removed the cell viability is determined using CellTiter-Glo® reagent. The test sample is subsequently transferred to designated wells of a white assay plate and the luminescence determined using a luminometer.

Data Analysis

IC$_{50}$ values are also determined provided a clear dose-response relationship is observed.

Figure 4A:
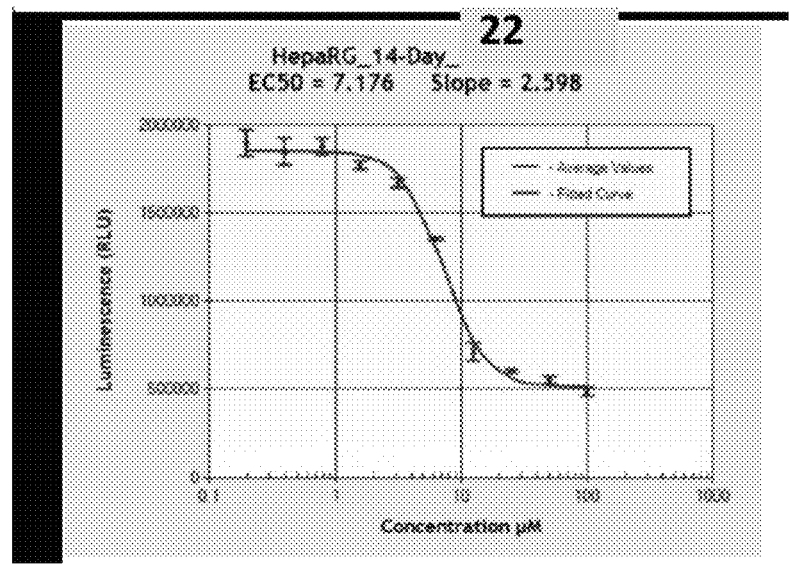
FIGS. 4a and 4b are charts showing the results of HepaRG cells treated with compounds 22 (FIG. 4a) and 23 (FIG. 4b), in terms of luminescence (RLU) vs. drug concentration (µM). Average values are shown with bars, and a fitted curve is also shown.
Figure 4B:
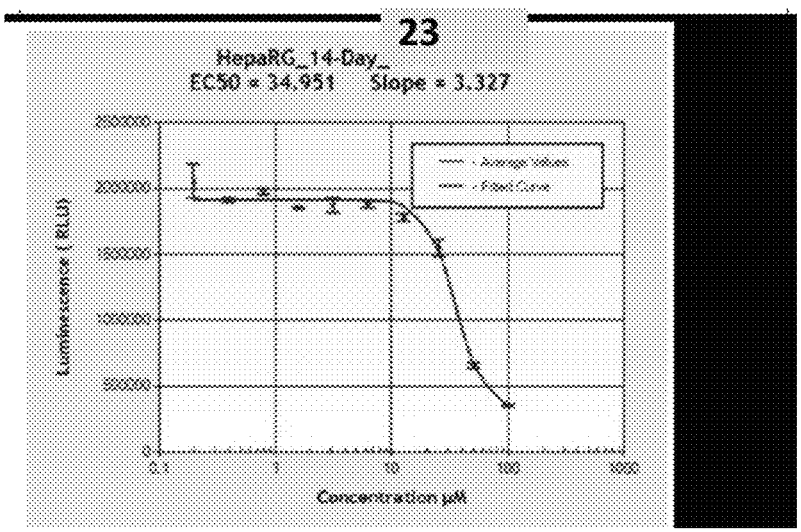

Results for compounds 22 and 23 are presented in Table 6 and FIGS. 4a and 4b.

TABLE 6

| Test Article | Cell Viability; IC$_{50}$ (μM) | Comments |
| --- | --- | --- |
| Carbonyl cyanide m-chlorophenyl hydrazone (CCCP) | 5.082 | Control |
| Tunicamycin | 0.011 | Control |
| Compound 22 | 7.176 | |
| Compound 23 | 34.951 | |

Example 9

NS5B Enzyme Assay

The 21-amino-acid C-terminal truncated HCV NS5B RNA polymerase can be cloned from the HCV replicon cells, modified with a six-His-terminal tail, expressed in a prokaryotic expression vector (pQE60; Qiagen), and subsequently purified over a Talon cobalt affinity resin column (Clontech, Palo Alto, Calif.).[1] Purification can be monitored by SDS-PAGE and Western blotting. The resulting purified protein can be dialyzed overnight against 50 mM sodium phosphate (pH 8.0)-300 mM sodium chloride-0.5% Triton X-100-50% glycerol-2 mM dithiothreitol. The dialysate maintains consistent activity for more than 6 months when stored at −20° C. Protein can be quantified with the Coomassie Plus protein assay reagent (Pierce) by using a bovine serum albumin standard from the same supplier.

NS5B RNA polymerase reaction can be studied by monitoring the incorporation of $^{32}$P-labeled UMP into the newly synthesized RNA strand by using minus IRES as the template. A steady-state reaction can be performed in a total volume of 140 mL containing 2.8 mg of minus IRES RNA template, 140 units of anti-RNase (Ambion), 1.4 mg of NS5B, an appropriate amount of [a-$^{32}$P]UTP, various concentrations of natural and modified nucleotides, 1 mM MgCl$_2$, 0.75 mM MnCl$_2$, and 2 mM dithiothreitol in 50 mM HEPES buffer (pH 7.5). The nucleotide concentration can be changed depending on the inhibitor. The reaction temperature is typically around 27° C. At the desired times, 20-mL aliquots can be taken and the reaction quenched by mixing the reaction mixture with 80 mL of stop solution containing 12.5 mM EDTA, 2.25 M NaCl, and 225 mM sodium citrate. In order to determine steady-state parameters for a natural nucleotide TP (NTP) substrate, one NTP concentration can be varied and the concentrations of the other three NTPs can be fixed at saturating concentrations. For determining the K$_i$ for an A analog, the concentrations of UTP, GTP, and CTP can be fixed at 10, 100, and 100 mM, respectively, and the concentrations of ATP and the A analog can be varied. The radioactive RNA products can be separated from unreacted substrates by passing the quenched reaction mixture through a Hybond N+ membrane (Amersham Biosciences) by using a dot blot apparatus. The RNA products can be retained on the membrane and the free nucleotides can be washed out. The membrane can be washed, for example, four times, with a solution containing 0.6 M NaCl and 60 mM sodium citrate. After the membrane is rinsed with water followed by rinsing with ethanol, the dots can be cut out and the radioactivity counted in a Packard liquid scintillation counter. The amount of product can be calculated on the basis of the total radioactivity in the reaction mixture. The rate of the reaction can be determined from the slope of the time course of product formation. To determine the inhibition constant ($K_i$), reaction rates can be determined with different concentrations of the substrate and the inhibitor and fit to a competitive inhibition equation: $v=(V_{max}\cdot[s])/\{K_m\cdot(1+[I]/K_i)+[S]\}$, where v is the observed rate, [S] is the substrate concentration, [I] is the inhibitor concentration, and $V_{max}$ is the maximum rate. $K_m$ is the Michaelis constant, and $K_i$ is the inhibition constant.

Using the protocol outlined above, the active triphosphates of Compound, of 2'-methyl urindine, and 2'-fluoro, 2'-methyl uridine were prepared and screened. Comparative results of the active triphosphates of Compound, of 2'-methyl urindine, and 2'-fluoro, 2'-methyl uridine are shown in Table 7.

REFERENCES

1) Stuyver L J, Whitaker T, McBrayer T R, Hernandez-Santiago B I, Lostia S, Tharnish P M, Ramesh M, Chu C K, Jordan R, Shi J, Rachakonda S, Watanabe K A, Otto M J, Schinazi R F. Ribonucleoside Analogue That Blocks Replication of Bovine Viral Diarrhea and Hepatitis C Viruses in Culture Antimicrob. Agents Chemother. 2003, 47, 244.

TABLE 7

| | $EC_{50}$ (µM)[a] | | |
|---|---|---|---|
| NS5B enzyme | 7-TP 2'-F-2'-F-UTP | 2'-Me-UTP | 2'-Me-2'-F-UTP[b] |
| GT 1b WT | 21 ± 8.7 | 2.2 ± 0.8 | 2.9 ± 0.6 |
| GT 1b S96T | 65 ± 4.0 | 9.2 ± 0.7 | 0.6 ± 0.1 |
| GT 1b S282T | TBD | TBD | TBD |
| GT 1b L159F | TBD | 2.4 ± 0.9 | 6.9 ± 1.5 |
| GT 1b L320F | 36 ± 1.5 | 3.3 ± 2.4 | 2.2 ± 0.6 |
| GT 1b V321A | 27 ± 23 | 2.5 ± 1.3 | 6.5 ± 3.2 |
| GT 2a WT | 11 ± 1.5 | TBD | 1.1 ± 0.01 |
| GT 3a WT | 15 ± 6.5 | 1.8 | 7.2 ± 2.1 |
| GT 3a L159F | 41 ± 26 | 1.5 | 5.2 ± 1.4 |

[a]In vitro $EC_{50}$ values are an average of two to three replicates ± SD.
[b]2'-Me-2'-F-UTP is the active metabolite of sofosbuvir.

Example 10

In Vitro Human Mitochondrial RNA Polymerase (POLRMT) Assay

In vitro RNA nucleotide incorporation assays with POLRMT (INDIGO Biosciences) were performed as previously described (Arnold et al. 2012). Briefly, $^{32}$P-radiolabeled RNA primer (5'-UUUUGCCGCGCC) (SEQ ID NO. 7) was hybridized to 3 molar excess of the appropriate DNA template (5'-GGGAATGCANGGCGCGGC (SEQ ID NO. 8) where position N was replaced by A, T, or C). 125 nM of POLRMT was incubated with 500 nM of 5'-radiolabeled RNA/DNA hybrid, 10 mM $MgCl_2$ and 100 µM of the corresponding nucleoside triphosphate. For non-nucleoside analogs, 100 µM of inhibitor was added at the same time as 100 µM UTP. Incorporation was allowed to proceed for 2 h at 30° C. and reactions were stopped by the addition of 10 mM EDTA and formamide. Samples were visualized on 20% denaturing polyacrylamide gel. Data were analyzed by normalizing the product fraction for each nucleoside triphosphate analog to that of the corresponding natural nucleoside triphosphate.

Figure 5:
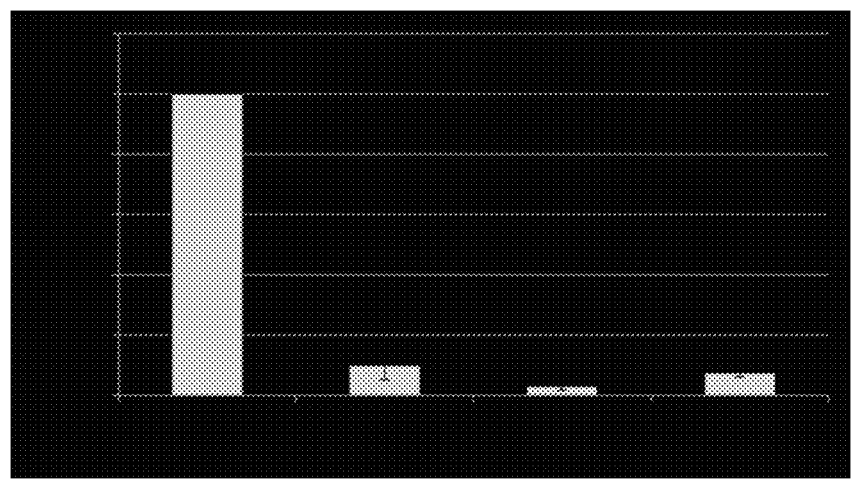
FIG. 5 is a chart showing rNTP incorporation with the POLRMT enzyme.

We tested whether nucleoside triphosphate analog of 7 was a substrate for the human mitochondrial RNA polymerase (POLRMT). 100 µM of each rNTP was incubated with POLRMT enzyme and the appropriate DNA/RNA primer/template hybrid and incorporation was evaluated at 2 hr. Nucleoside triphosphate analog incorporation was normalized to that of natural rNTP substrates. As shown in FIG. 5, 7-TP was incorporated 7.4% as compared to natural UTP. This value was comparable to the active metabolite of sofosbuvir (3.1%) and 2'-C-Me-UTP (9.8%).

Example 11

RNA Synthesis and Chain Termination
i) Expression and Purification of HCV NS5B:

The HCV NS5B sequence, inserted into the expression vector pET-22 (Novagen), can be expressed as a C terminally truncated enzyme (Δ21) in *Escherichia coli* BL21 (DE3) and purified utilizing metal ion affinity chromatography (Talon kit from Clonetech). Sequences can be confirmed by sequencing (Sequetech).

ii) Standard Reaction Conditions:

Reaction mixtures can consist of 1 µM RNA template (RNA20), 1.5 µM HCV NS5B, and 0.25 µM radiolabeled primer (P16) in a buffer containing 40 mM HEPES, pH 8, 10 mM NaCl, 1 mM dithiothreitol, and 0.2 mM $MnCl_2$. In addition, reactions contained 10 µM GTP-UTP and 3 µM test analog-TP. Reactions can be stopped after 30 minutes and products can be precipitated with isopropanol, heat denatured for 5 minutes at 95° C., and separated on 12% polyacrylamide, 7 µM urea gels. The concentration of chain terminator required to inhibit 50% of full-length product formation ($EC_{50}$) can be determined for a single site of nucleotide analog incorporation with template/primer.

iii) Data Acquisition and Analysis:

Gels can be scanned and analyzed with a phosphorimager (FLA-7000, Fujifilm), and $EC_{50}$ values can be calculated.

Example 12

Effect of Nucleotide Analogs on the DNA Polymerase and Exonuclease Activities of Mitochondrial DNA Polymerase γ
i) Purification of Human Polymerase γ:

The recombinant large and small subunits of polymerase γ can be purified as described previously (see Graves S W, Johnson A A, Johnson K A. Expression, purification, and initial kinetic characterization of the large subunit of the human mitochondrial DNA polymerase. *Biochemistry*. 1998, 37, 6050-8; Johnson A A, Tsai Y, Graves S W, Johnson K A. Human mitochondrial DNA polymerase holoenzyme: reconstitution and characterization. Biochemistry 2000; 39: 1702-8). The protein concentration can be determined spectrophotometrically at 280 nm, with extinction coefficients of 234,420, and 71,894 M-1 cm-1 for the large and the small subunits of polymerase γ, respectively.

ii) Kinetic Analyses of Nucleotide Incorporation.

Pre-steady-state kinetic analyses can be carried out to determine the catalytic efficiency of incorporation (k/K) for DNA polymerase γ for nucleoside-TP and natural dNTP substrates. This allowed determination of the relative ability of this enzyme to incorporate modified analogs and predict toxicity. Pre-steady-state kinetic analyses of incorporation of nucleotide analogs by DNA polymerase γ would be carried out essentially as described previously (see Murakami E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. *Antiviral Res.* 2004, 62, 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. *Antimicrob Agents Chemother.* 2004, 48, 1300-6). Briefly, a pre-incubated mixture of large (250 nM) and small (1.25 mM) subunits of polymerase γ and 60 nM DNA template/primer in 50 mM Tris-HCl, 100 mM NaCl, pH 7.8, can be added to a solution containing $MgCl_2$ (2.5 mM) and various concentrations of nucleotide analogs. Reactions can be quenched and analyzed as described previously. Data can be fit to the same equations as described above.

iii) Assay for Human Polymerase γ 3' 5' Exonuclease Activity:

The human polymerase γ exonuclease activity can be studied by measuring the rate of formation of the cleavage products in the absence of dNTP. The reaction can be initiated by adding $MgCl_2$ (2.5 mM) to a pre-incubated mixture of polymerase γ large subunit (40 nM), small subunit (270 nM), and 1,500 nM chain-terminated template/primer in 50 mM Tris-HCl, 100 mM NaCl, pH 7.8, and quenched with 0.3M EDTA at the designated time points. All reaction mixtures would be analyzed on 20% denaturing polyacrylamide sequencing gels (8M urea), imaged on a Bio-Rad GS-525 molecular image system, and quantified with Molecular Analyst (Bio-Rad). Products formed from the early time points would be plotted as a function of time. Data would be fitted by linear regression with Sigma Plot (Jandel Scientific). The slope of the line can be divided by the active enzyme concentration in the reaction to calculate the kexo for exonuclease activity (see Murakami E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. Antiviral Res. 2004; 62: 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. Antimicrob Agents Chemother. 2004; 48: 1300-6).

Example 13

Synthesis of Nucleoside Analog Triphosphates

Nucleoside analog triphosphates can be synthesized from the corresponding nucleosides, using the Ludwig and Eckstein's method. (Ludwig J, Eckstein F. "Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one" *J. Org. Chem.* 1989, 54 631-5) The crude nucleoside analog triphosphates can be purified, for example, by FPLC using a HiLoad 26/10 Q Sepharose Fast Flow Pharmacia column and gradient of TEAB buffer (pH 7.0). The product can be characterized by one or more of UV spectroscopy, proton NMR, phosphorus NMR, mass spectroscopy and/or HPLC.

The resulting triphosphates can be used as controls for the cellular pharmacology assays described above and for kinetic work with HCV and human Pols.

Example 14

Inhibition of Human DNA Polymerases by NTP's
Study Objectives

To determine whether a nucleoside-Triphosphate analog inhibits human DNA polymerases Alpha, Beta and Gamma and to calculate $IC_{50}$ values.

Materials and Methods

Human DNA Polymerase Alpha Enzyme was purchased from Chimerx (cat#1075) and assayed based on their recommendations with some modifications. The 2'-Me-UTP was treated with Inorganic Pyrophosphatase (Sigma) to remove any pyrophosphate contamination. A final concentration of 500 μM 2'-Me-UTP was incubated with 1 mM DTT, 50 mM Tris, 50 mM NaCl, 6 mM $MgCl_2$, and 1 unit of pyrophosphatase for 1 hour at 37° C. followed by inactivation at 95° C. for 10 minutes. A mixture of 0.05 units of Human DNA Polymerase Alpha and a 5'end radiolabeled 24nt DNA primer (5'-TCAGGTCCCTGTTCGGGCGC-CACT) (SEQ ID NO. 9) annealed to a 48nt DNA template (5'-CAGTGTGGAAAATCTCTAGCAGTGGCGC-CCGAACAGGGACCTG AAAGC) (SEQ ID NO. 10) was mixed with increasing concentrations of compound from 0 to 100 μM in 60 mM Tris-HCl (pH 8.0), 5 mM magnesium acetate, 0.3 mg/ml bovine serum albumin, 1 mM dithiothreitol, 0.1 mM spermine, 0.05 mM of each dCTP, dGTP, dTTP, dATP in a final reaction volume of 20 μl for 5 min at 37° C. (all concentrations represent final concentrations after mixing). The reactions were stopped by mixing with 0.3 M (final) EDTA. Products were separated on a 20% polyacrylamide gel and quantitated on a Bio-Rad Molecular Imager FX. Results from the experiments were fit to a dose response equation, (y min+((y max)−(y min)))/(1+(compound concentration)/$IC_{50}$)^slope) to determine $IC_{50}$ values using Graphpad Prism or SynergySoftware Kaleidagraph. Data was normalized to controls.

Human DNA Polymerase Beta—Enzyme was purchased from Chimerx (cat#1077) and assayed based on their recommendations with some modifications. A mixture of 0.1 units of Human DNA Polymerase Beta and a 5'end radiolabeled 24nt DNA primer (5'-TCAGGTCCCTGT-TCGGGCGCCACT) (SEQ ID NO. 9) annealed to a 48nt DNA template (5'-CAGTGTGGAAAATCTCTAGCAGTG-GCGCCCGAACAGGGACCTG AAAGC) (SEQ ID NO. 10) was mixed with increasing concentrations of compound from 0 to 100 μM in 50 mM Tris-HCl (pH 8.7), 10 mM KCl, 10 mM $MgCl_2$, 0.4 mg/ml bovine serum albumin, 1 mM dithiothreitol, 15% (v/v) glycerol, and 0.05 mM of each dCTP, dGTP, dTTP, dATP in a final reaction volume of 20 μl for 5 min at 37° C. (all concentrations represent final concentrations after mixing). The reactions were stopped by mixing with 0.3 M (final) EDTA. Products were separated on a 20% polyacrylamide gel and quantitated on a Bio-Rad Molecular Imager FX. Results from the experiments were fit to a dose response equation, (y min+((y max)−(y min)))/(1+ (compound concentration)/$IC_{50}$)^slope) to determine $IC_{50}$ values using Graphpad Prism or SynergySoftware Kaleidagraph. Data was normalized to controls.

Human DNA Polymerase Gamma—Enzyme was purchased from Chimerx (cat#1076) and assayed based on their recommendations with some modifications. A mixture of 0.625 units of Human DNA Polymerase Gamma and a 5' end radiolabeled 24nt DNA primer (5'-TCAGGTCCCTGT-TCGGGCGCCACT) (SEQ ID NO. 9) annealed to a 36nt DNA template (5'-TCTCTAGAAGTGGCGCCCGAACA-GGGACCTGAAAGC) (SEQ ID NO. 11) was mixed with increasing concentrations of compound from 0 to 100 μM in 50 mM Tris-HCl (pH 7.8), 100 mM NaCl, 5 mM $MgCl_2$, and 0.05 mM of each dCTP, dGTP, dTTP, dATP in a final reaction volume of 20 µl for 200 min at 37° C. (all concentrations represent final concentrations after mixing). The reactions were stopped by mixing with 0.3 M (final) EDTA. Products were separated on a 20% polyacrylamide gel and quantitated on a Bio-Rad Molecular Imager FX. Results from the experiments were fit to a dose response equation, (y min+((y max)−(y min)))/(1+(compound concentration)/$IC_{50}$)^slope) to determine $IC_{50}$ values using Graphpad Prism or SynergySoftware Kaleidograph. Data was normalized to controls.

Results

7-TP was tested against human DNA polymerase Alpha, Beta and Gamma to determine $IC_{50}$ values. $IC_{50}$' for 7-TP were found to be >100 µM for human DNA polymerase Alpha, Beta and Gamma.

Example 15

Cellular Pharmacology in HepG2 Cells

HepG2 cells are obtained from the American Type Culture Collection (Rockville, Md.), and are grown in 225 $cm^2$ tissue culture flasks in minimal essential medium supplemented with non-essential amino acids, 1% penicillin-streptomycin. The medium is renewed every three days, and the cells are subcultured once a week. After detachment of the adherent monolayer with a 10 minute exposure to 30 mL of trypsin-EDTA and three consecutive washes with medium, confluent HepG2 cells are seeded at a density of 2.5×10$^6$ cells per well in a 6-well plate and exposed to 10 µM of [$^3$H] labeled active compound (500 dpm/pmol) for the specified time periods.

The cells are maintained at 37° C. under a 5% $CO_2$ atmosphere. At the selected time points, the cells are washed three times with ice-cold phosphate-buffered saline (PBS). Intracellular active compound and its respective metabolites are extracted by incubating the cell pellet overnight at −20° C. with 60% methanol followed by extraction with an additional 20 pal of cold methanol for one hour in an ice bath. The extracts are then combined, dried under gentle filtered air flow and stored at −20° C. until HPLC analysis.

Example 16

Cellular Pharmacology in Huh7 Cells

Similar to the method outlined for HepG2 cellular pharmacology, compounds were incubated in Huh-7 cells for 4 hr at the concentration of 50 µM in triplicate. 3TC was used as a positive control and done in duplicate, while DMSO (10 µL) was incubated as a blank control in duplicate. Ice-cold 70% methanol was used as the extraction solvent. ddATP (10 nM) was used as the internal standard.

The triphosphate production of compound 9, versus Sofosbuvir (SOF), in Huh-7 cells, is shown in FIG. 1 and in Table 8 below.

TABLE 8

| pmol/10$^6$ cells | 7 | 9 | pmol/10$^6$ cells | Sofosbuvir |
|---|---|---|---|---|
| 7* | NA | NA | SOF-nuc | BLOQ |
| 7-MP | BLOQ | 12.4 ± 1.5 | SOF-MP | 7.3 ± 0.1 |
| 7-DP | BLOQ | 252 ± 14 | SOF-DP | 12.5 ± 0.4 |

TABLE 8-continued

| pmol/10$^6$ cells | 7 | 9 | pmol/10$^6$ cells | Sofosbuvir |
|---|---|---|---|---|
| 7-TP | BLOQ | 98.2 ± 2.2 | SOF-TP | 317.2 ± 3.4 |
| 9 | BLOQ | 318.4 ± 26.6 | SOF | 206.4 ± 3.2 |

*7 shows very poor signal in both positive and negative mode in LC-MS (LLOQ is around 200 pmol/millon cells)

Example 17

Cellular Pharmacology in PBM Cells

Test compounds are incubated in PBM cells at 50 µM for 4 h at 37° C. Then the drug containing media is removed and the PBM cells are washed twice with PBS to remove extracellular drugs. The intracellular drugs are extracted from 10×10$^6$ PBM cells using 1 mL 70% ice-cold methanol (containing 10 nM of the internal standard ddATP). Following precipitation, the samples are maintained at room temperature for 15 min followed by vortexing for 30 sec, and then stored 12 h at −20° C. The supernatant is then evaporated to dryness. Dry samples would be stored at −20° C. until LC-MS/MS analysis. Prior to analysis, each sample is reconstituted in 100 µL mobile phase A, and centrifuged at 20,000 g to remove insoluble particulates.

Gradient separation is performed on a Hypersil GOLD column (100×1.0 mm, 3 µm particle size; Thermo Scientific, Waltham, Mass., USA). Mobile phase A consists of 2 mM ammonium phosphate and 3 mM hexylamine. Acetonitrile is increased from 10 to 80% in 15 min, and kept at 80% for 3 min. Equilibration at 10% acetonitrile lasts 15 min.

The total run time is 33 min. The flow rate is maintained at 50 µL/min and a 10 µL injection is used. The autosampler and the column compartment are typically maintained at 4.5 and 30° C., respectively.

The first 3.5 min of the analysis is diverted to waste. The mass spectrometer is operated in positive ionization mode with a spray voltage of 3.2 kV.

Example 18

A West Nile virus drug susceptibility assay can also be performed as previously described in: Song, G. Y., Paul, V., Choo, H., Morrey, J., Sidwell, R. W., Schinazi, R. F., Chu, C. K. Enantiomeric synthesis of D- and L-cyclopentenyl nucleosides and their antiviral activity against HIV and West Nile virus. *J. Med. Chem.* 2001, 44, 3985-3993, Example 19

A yellow fever drug susceptibility assay can also be performed as previously described in: Julander, J. G., Furuta, Y., Shafer, K., Sidwell, R. W. Activity of T-1106 in a Hamster Model of Yellow Fever Virus Infection. *Antimicrob. Agents Chemother.* 2007, 51, 1962-1966.

Example 20

The essential role of a particular viral protein (Dengue virus envelope protein (E)) in viral propogation. Mondotte et al., J. Virol. July 2007, vol. 81 no. 13 7136-7148 discloses an assay useful for identifying compounds for treating infections caused by the Dengue virus, and this assay can be used to identify those compounds described herein which are active against Dengue.

Another assay is described in Levin, 14th International Symposium on Hepatitis C Virus & Related Viruses, Glasgow, UK, 9-13 Sep. 2007. The assay relates to human and Dengue virus polymerase, where putative compounds can be tested against the enzymes, preferably in duplicate, over a range of concentrations, such as from 0.8 mM to 100 mM. The compounds can also be run alongside a control (no inhibitor), a solvent dilution (0.016% to 2% DMSO) and a reference inhibitor.

A suitable high throughput assay for Dengue is described in Lim et al., Antiviral Research, Volume 80, Issue 3, December 2008, Pages 360-369. Dengue virus (DENV) NS5 possesses methyltransferase (MTase) activity at its N-terminal amino acid sequence and is responsible for formation of a type 1 cap structure, m7GpppAm2'-O in the viral genomic RNA. Optimal in vitro conditions for DENV2 2'-O-MTase activity can be characterized using purified recombinant protein and a short biotinylated GTP-capped RNA template. Steady-state kinetics parameters derived from initial velocities can be used to establish a robust scintillation proximity assay for compound testing. Pre-incubation studies by Lim et al., Antiviral Research, Volume 80, Issue 3, December 2008, Pages 360-369, showed that MTase-AdoMet and MTase-RNA complexes can be equally catalytically competent and the enzyme supports a random bi kinetic mechanism. Lim validated the assay with competitive inhibitory agents, S-adenosyl-homocysteine and two homologues, sinefungin and dehydrosinefungin. A GTP-binding pocket present at the N-terminal of DENV2 MTase can be previously postulated to be the cap-binding site. This assay allows rapid and highly sensitive detection of 2'-O-MTase activity, and can be readily adapted for high-throughput screening for inhibitory compounds.

Example 21

Anti-Norovirus Activity

Compounds can exhibit anti-norovirus activity by inhibiting norovirus polymerase and/or helicase, by inhibiting other enzymes needed in the replication cycle, or by other pathways.

There is currently no approved pharmaceutical treatment for Norovirus infection (http://www.cdc.gov/ncidod/dvrd/revb/gastro/norovirus-qa.htm), and this has probably at least in part been due to the lack of availability of a cell culture system. Recently, a replicon system has been developed for the original Norwalk G-I strain (Chang, K. O., et al. (2006) Virology 353:463-473).

Both Norovirus replicons and Hepatitis C replicons require viral helicase, protease, and polymerase to be functional in order for replication of the replicon to occur. Most recently, an in vitro cell culture infectivity assay has been reported utilizing Norovirus genogroup I and II inoculums (Straub, T. M. et al. (2007) Emerg. Infect. Dis. 13(3):396-403). This assay is performed in a rotating-wall bioreactor utilizing small intestinal epithelial cells on microcarrier beads. The infectivity assay may be useful for screening entry inhibitors.

Example 22

Diagnosis of Norovirus Infection

One can diagnose a norovirus infection by detecting viral RNA in the stools of affected persons, using reverse transcription-polymerase chain reaction (RT-PCR) assays. The virus can be identified from stool specimens taken within 48 to 72 hours after onset of symptoms, although one can obtain satisfactory results using RT-PCR on samples taken as long as 7 days after the onset of symptoms. Other diagnostic methods include electron microscopy and serologic assays for a rise in titer in paired sera collected at least three weeks apart. There are also commercial enzyme-linked immunoassays available, but these tend to have relatively low sensitivity, limiting their use to diagnosis of the etiology of outbreaks. Clinical diagnosis of norovirus infection is often used, particularly when other causative agents of gastroenteritis have been ruled out.

Example 23

Anti-Chikungunya Activity

Anti-Chikungunya Activity can be evaluated as outlined in "Anti-Chikungunya Viral Activities of Aplysiatoxin-Related Compounds from the Marine Cyanobacterium *Trichodesmium erythraeum*" Gupta, D. K.; Kaur, P.; Leong, S. T.; Tan, L. T.; Prinsep, M. R.; Chu, J J. H. Mar Drugs. January 2014; 12(1): 115-127; 10.3390/md12010115 and references cited therein.

Example 24

Anti-Cancer Assays

Anti-cancer assays may be found in the following references and those references cited therein:
"Handbook of Anticancer Drug Development" Lippincott Williams & Wilkins, by Daniel R. Budman, Alan Hilary Calvert, Eric Keith Rowinsky, 2003 (400 pages)
"Apoptosis assays for quantifying the bioactivity of anti-cancer drug products" Joslyn K. Brunelle, Baolin Zhang Drug Resistance Updates, 13(6) 2010, Pages 172-179.

Example 25

Anti-RSVActivity

Anti-RSV activity may be evaluated as outlined in the references below:
"Polyadenylation-dependent screening assay for respiratory syncytial virus RNA transcriptase activity and identification of an inhibitor" Stephen W. Mason, Carol Lawetz, Yvon Gaudette, Florence Dô, Erika Scouten, Lisette Lagacé, Bruno Simoneaul Michel Liuzzi. Nucl. Acids Res. (2004) 32 (16): 4758-4767; doi: 10.1093/nar/gkh809.
"Screening and evaluation of anti-respiratory syncytial virus compounds in cultured cells" Lundin A1, Bergström T, Trybala E. Methods Mol Biol. 2013; 1030: 345-63. doi: 10.1007/978-1-62703-484-5_27.
"A fluorescence-based high-throughput antiviral compound screening assay against respiratory syncytial virus" Kwanten L I, De Clerck B, Roymans D. Methods Mol Biol. 2013; 1030:337-44. doi: 10.1007/978-1-62703-484-5_26.

Example 26

Anti-Influenza Activity

Anti-influenza activity may be evaluated as outlined in the references below: Schmidtke et al., "A rapid assay for evaluation of antiviral activity against coxsackie virus B3, influenza virus A, and herpes simplex virus type 1," J Virol Methods. 2001 June; 95(1-2):133-43.
Ching-Yao Su, "High-throughput identification of compounds targeting influenza RNA-dependent RNA polymerase activity," PNAS, vol. 107 no. 45, 19151-19156 (Nov. 9, 2010).

"In vitro and in vivo assay systems for study of influenza virus inhibitors" Robert W. Sidwell; Donald F. Smee. Antiviral Research 48(1) 2000, Pages 1-16.

"A cell-based luminescence assay is effective for high-throughput screening of potential influenza antivirals" James W. Noah; William Severson; Diana L. Noah; Lynn Rasmussen; E. Lucile White; Colleen B. Jonsson. Antiviral Research 73(1) 2007, Pages 50-59.

"High-Throughput Screening of a 100,000-Compound Library for Inhibitors of Influenza A Virus (H3N2)" William E. Severson; Michael McDowell; Subramaniam Ananthan; Dong-Hoon Chung; Lynn Rasmussen; Melinda I. Sosa; E. Lucile White; James Noah; Colleen B. Jonsson. J Biomol Screen 2008 13: 879-887, doi: 10.1177/1087057108323123.

Example 27

Anti-HEV Activity

Hepatitis E virus (HEV) is a major cause of hepatitis. Hepatitis E virus (HEV) is the principal cause of acute hepatitis on the Indian subcontinent, in southeastern and central Asia, in the Middle East, in Mexico, and in parts of Africa. It is associated with the consumption of fecally contaminated drinking water. Although HEV is associated with a low case fatality rate in the general population, pregnant women in the second and third trimesters are at greater risk (case fatality rates of 10 to 24%) for fulminant hepatitis and fetal loss.

There are several commercial HEV diagnostic assays that can be used to identify infection with HEV (Myint et al., J Clin Microbiol. 2006 April; 44(4): 1581-1583). Myint determined that HEV viremia is universal and has the highest diagnostic score (sensitivity, 85%). The viremia also appears prolonged, starting from the onset of illness and lasting for ≥2 weeks. Given these findings, and in the absence of reference serological assays, HEV RT-PCR can be used as a reference assay for HEV detection.

As viremia does not always coincide with the antibody response in the natural course of HEV infection, detection of IgA alone or together with IgM can provide better specificity and a longer duration of positivity for diagnosis of HEV infection (Takahashi, M., S. Kusakai, H. Mizuo, K. Fujimura, K. Masuko, Y. Sugai T. Aikawa, T. Nishizawa, and H. Okamoto. 2005. Simultaneous detection of immunoglobulin A (IgA) and IgM antibodies against hepatitis E virus (HEV) is highly specific for diagnosis of acute HEV infection. J. Clin. Microbiol. 43:49-56).

Commercial IgM anti-HEV assays can be used, such as the WRAIR assay (Walter Reed Army Institute of Research) and the Genelabs IgM assay (Genelabs Diagnostics (GLD) Pty. Ltd., Singapore).

Commercial enzyme immunoassays (EIAs) for detecting total Ig or IgG anti-HEV can be used, including the Abbott IgG anti-HEV EIA (Abbott Diagnostika, Wiesbaden-Delkenheim, Germany), the GLD IgG (Genelabs Diagnostics (GLD) Pty. Ltd., Singapore), and the WRAIR total Ig anti-HEV EIA (Walter Reed Army Institute of Research).

Of these screens, Myint noted that the Abbott immunoglobulin G (IgG), Genelabs IgG, and Walter Reed Army Institute of Research (WRAIR) IgM assays were about 90% sensitive, and the Abbott IgG and WRAIR total Ig and IgM assays were more than 90% specific.

All HEV strains identified to date appear to belong to the same serotype, and recombinant HEV antigens react well with sera from all geographical origins. However, the Myint study noted that the sensitivity of the serological assays was greater for symptomatic than for asymptomatic HEV infections.

Example 28

Intracellular Metabolism in Human Hepatocytes

Figure 2:
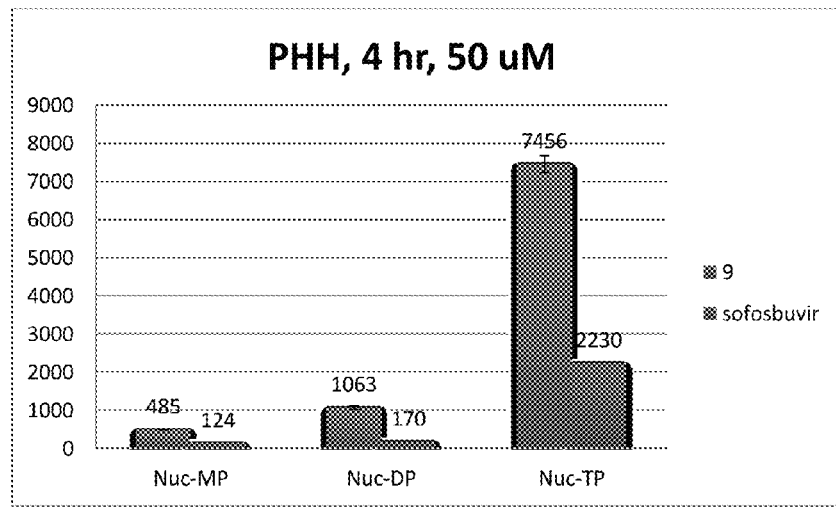
FIG. 2 is a chart showing the triphosphate production from Compound 9, versus Sofosbuvir, in human hepatocytes.

Fresh plated human primary hepatocytes (Bioreclamation IVT, Baltimore, Md.) were seeded at $1 \times 10^6$ per well in 12-well plates. After acclimating overnight, hepatocytes cells were exposed to 50 μM of compound. At 4 h, medium was removed from the cell layers and cells were washed twice with ice-cold phosphate buffered saline (PBS) to remove any residual medium. Cells were re-suspended in 70% methanol containing 20 nM ddATP overnight at −20° C. The supernatants were dried under a flow of air and dried samples stored at −20° C. until analysis by LC-MS/MS. The triphosphate production of compound 9, versus Sofosbuvir, in human hepatocytes, is shown in FIG. 2. The results show that roughly 300% more active triphosphate is produced when compound 9 is incubated in human hepatocytes than when Sofosbuvir is incubated, at the same concentration, in the same cell line.

FIGS. 6a-b shows the cellular egress of Compound 9 (FIG. 6a) and sofosbuvir (FIG. 6b) in Primary Human Hepatocytes. The results are tabulated in Tables 9 (Compound 9) and 10 (Sofosbuvir).

TABLE 9

| Time (hr) | 9-MP | 9-DP | 9-TP |
|---|---|---|---|
| 0 | 168 ± 35 | 361 ± 27 | 2045 ± 21 |
| 1 | 192 ± 1.4 | 461 ± 8.7 | 2072 ± 25 |
| 2 | 166 ± 21 | 472 ± 11 | 1882 ± 92 |
| 4 | 167 ± 17 | 440 ± 12 | 1733 ± 45 |
| 10 | 103 ± 13 | 270 ± 27 | 1020 ± 131 |
| 24 | 87.3 ± 6.8 | 192 ± 13 | 441 ± 30 |
| 48 | 66.8 ± 6.2 | 83.6 ± 2.7 | 74.3 ± 8.3 |
| $T_{1/2}$ (hr) | 31.0 | 18.9 | 9.9 |

TABLE 10

| Time (hr) | 2'-F, 2'Me UMP | 2'-F, 2'Me UDP | 2'-F, 2'Me UTP | MI |
|---|---|---|---|---|
| 0 | 185 ± 31 | 254 ± 1.0 | 2600 ± 79 | 276 ± 19 |
| 1 | 216 ± 14 | 311 ± 9.1 | 2585 ± 117 | 230 ± 16 |
| 2 | 239 ± 24 | 332 ± 4.9 | 2632 ± 143 | 183 ± 13 |
| 4 | 261 ± 40 | 415 ± 50 | 2903 ± 129 | 119 ± 0.03 |
| 10 | 129 ± 21 | 182 ± 34 | 1296 ± 189 | 8.2 ± 2.8 |
| 24 | 59.2 ± 10 | 111 ± 17 | 860 ± 73 | 0.91 ± 0.12 |
| 48 | BLOQ | 10.5 ± 2.6 | 129 ± 25 | BLOQ |
| $t_{1/2}$ (hr) | 9.8 | 8.7 | 10.4 | 2.8 |

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

We claim:

1. A compound of Formula (A) or (B):

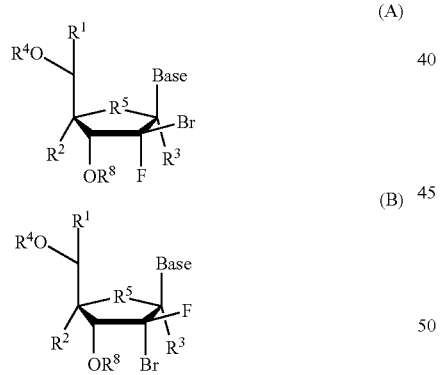

or a pharmaceutically acceptable salt, wherein:

$R^1$ is H or Me, wherein, when $R^1$ is Me it may be wholly or partially R or S or any mixture thereof;

$R^2$ is H, $N_3$, F, $(C_{1-8})$alkyl, $(C_{2-8})$alkenyl or $(C_{2-8})$alkynyl;

$R^4$ is H or $P(O)R^6R^7$, wherein, when chirality exists at the phosphorous center of $R^4$, it may be wholly or partially $R_p$ or $S_p$ or any mixture thereof, $R^5$ is O, $CH_2$, S, Se, CHF, $CF_2$, or $C=CH_2$, $R^3$ is H or CN when $R^5$ is O, and $R^3$ is selected from the group consisting of H, CN, $(C_{1-8})$alkyl, $(C_{2-8})$alkenyl, $(C_{2-8})$alkynyl and $O-(C_{1-8})$ alkyl when $R^5$ is $CH_2$, CHF, $CF_2$, or $C=CH_2$, $R^8$ is selected from the group consisting of H, C(O) $(C_{1-8})$alkyl, $C(O)(C_{1-8})$branched alkyl, C(O)NH $(C_{1-8})$alkyl, $C(O)NH(C_{1-8})$branched alkyl, C(O)aryl $C(O)(C_{1-8})$alkyl-aryl, $C(O)NH(C_{1-8})$alkyl-aryl C(O) $O(C_{1-8})$alkyl, $C(O)O(C_{1-8})$branched alkyl, C(O)O $(C_{1-8})$alkyl-aryl or $OR^8$ as it appears in Formulas A or B is an ester derived from an alpha amino acid, $R^6$ and $R^7$ are independently selected from the group consisting of:

(a) $OR^{15}$ where $R^{15}$ selected from the group consisting of H,

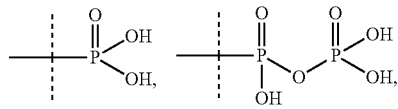

Li, Na, K, $C_{1-20}$alkyl, $C_{3-6}$ cycloalkyl, $C_{1-4}$ (alkyl) aryl, benzyl, $C_{1-6}$haloalkyl, $C_{2-3}$(alkyl)$OC_{1-20}$alkyl,

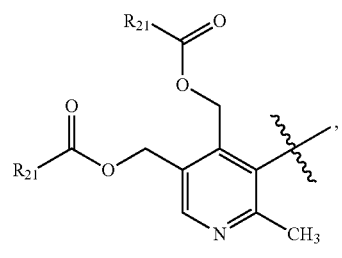

aryl, and heteroaryl, wherein phenyl and pyridinyl are optionally substituted with zero to three substituents independently selected from the group consisting of $(CH_2)_{0-6}CO_2R^{16}$ and $(CH_2)_{0-6}CON(R^{16})_2$;

$R^{16}$ is independently H, $C_{1-20}$ alkyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(b)

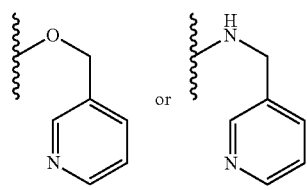

(c) the ester of a D- or L-amino acid

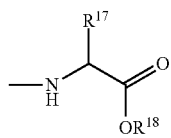

where $R^{17}$ is restricted to those occurring in natural L-amino acids, and $R^{18}$ is H, $C_{1-20}$ alkyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(d) $R^6$ and $R^7$ can come together to form a ring

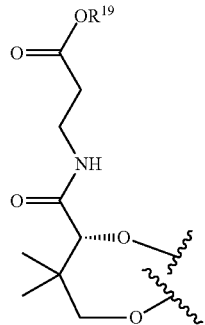

where $R^{19}$ is H, $C_{1-20}$ alkyl, $C_{1-20}$ alkenyl, the carbon chain derived from a fatty alcohol or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(e) $R^6$ and $R^7$ can come together to form a ring selected from the group consisting of

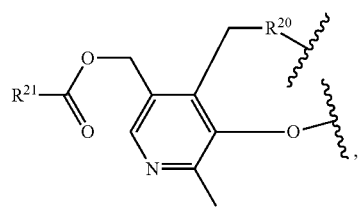

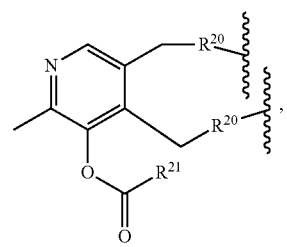

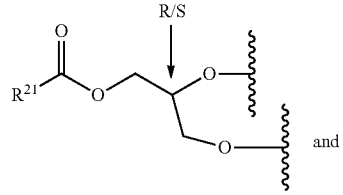

and

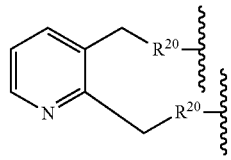

where $R^{20}$ is O or NH, and $R^{21}$ is selected from the group consisting of H, $C_{1-20}$ alkyl, $C_{1-20}$ alkenyl, the carbon chain derived from a fatty acid, and $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, heteroaryl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl, Base is selected from the group consisting of:

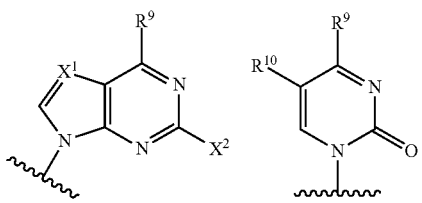

-continued

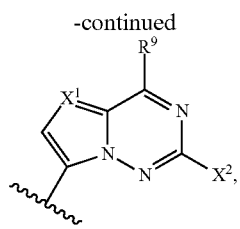

X[1] is CH, C—(C_{1-6})alkyl, C—(C_{2-6})alkenyl, C—(C_{2-6})alkynyl, C—(C_{3-7})cycloalkyl, C—(C_{1-6})haloalkyl, C—(C_{1-6})hydroxyalkyl, C—OR[22], C—N(R[22])_2 C-halo, C—CN or N, R[22] is independently H, (C_{1-10})alkyl, (C_{1-10})haloalkyl or (C_{3-7})cycloalkyl, R[9] is OH, NH_2, O(C_{1-10})alkyl, O(C_{3-7})cycloalkyl, NH(C_{1-10})alkyl, N((C_{1-10})alkyl)_2, NH(C_{3-7})cycloalkyl, NH(CO)(C_{1-20})alkyl, NH(CO)O(C_{1-20})alkyl, NHOH, NHO(CO)(C_{1-20})alkyl, NHO(CO)NH(C_{1-20})alkyl, R[10] is H, F or CH_3 and X[2] is H, F, Cl (C_{1-6})alkyl, (C_{2-6})alkenyl, (C_{2-6})alkynyl, C—(C_{3-7})cycloalkyl, C—(C_{1-6}) haloalkyl, (C_{1-6})haloalkyl, (C_{3-7})cycloalkyl, (C_{1-6})hydroxyalkyl, OR[22], SR[22], N(R[22])_2, NHC(O)OR[22], NHC(O)N(R[22])_2, NHC(O)R[22], CN or NH_2.

2. The compounds of claim 1, wherein the compounds can be present in the β-D or β-L configuration.

3. The compounds of claim 1, having one of the following formulas:

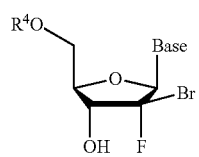
(A)

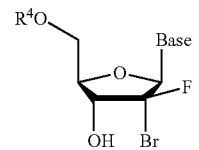
(B)

where R[4] and Base are as defined above in claim 1.

4. A compound of claim 1, having one of the following formulas:

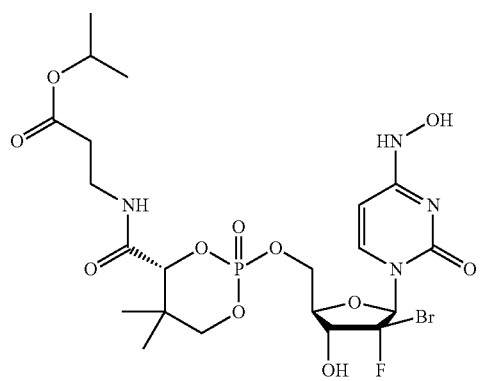

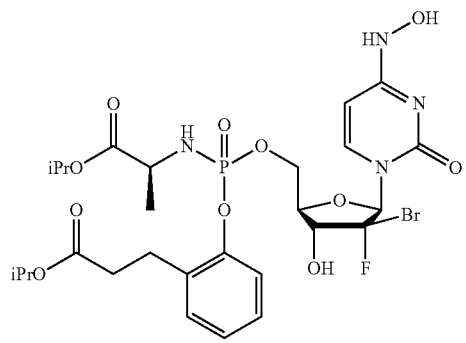

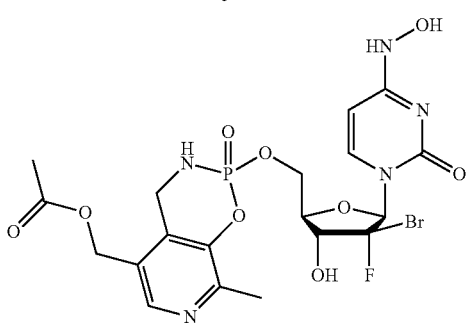

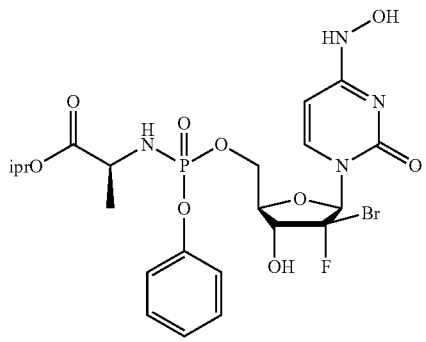

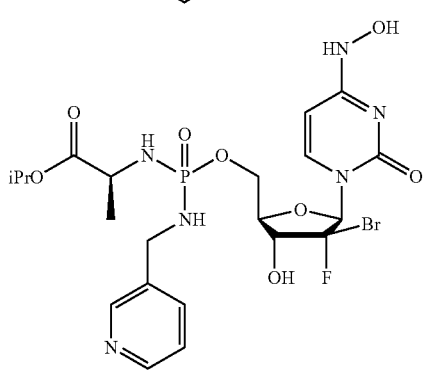

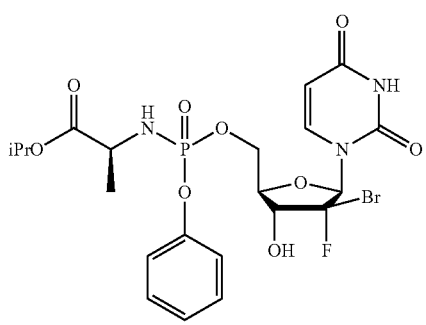

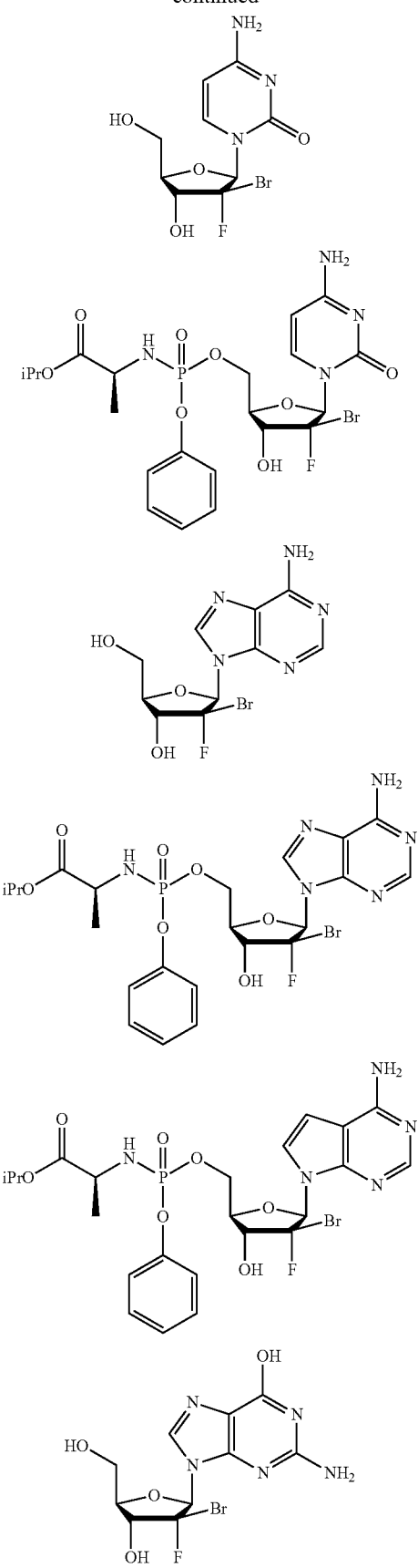
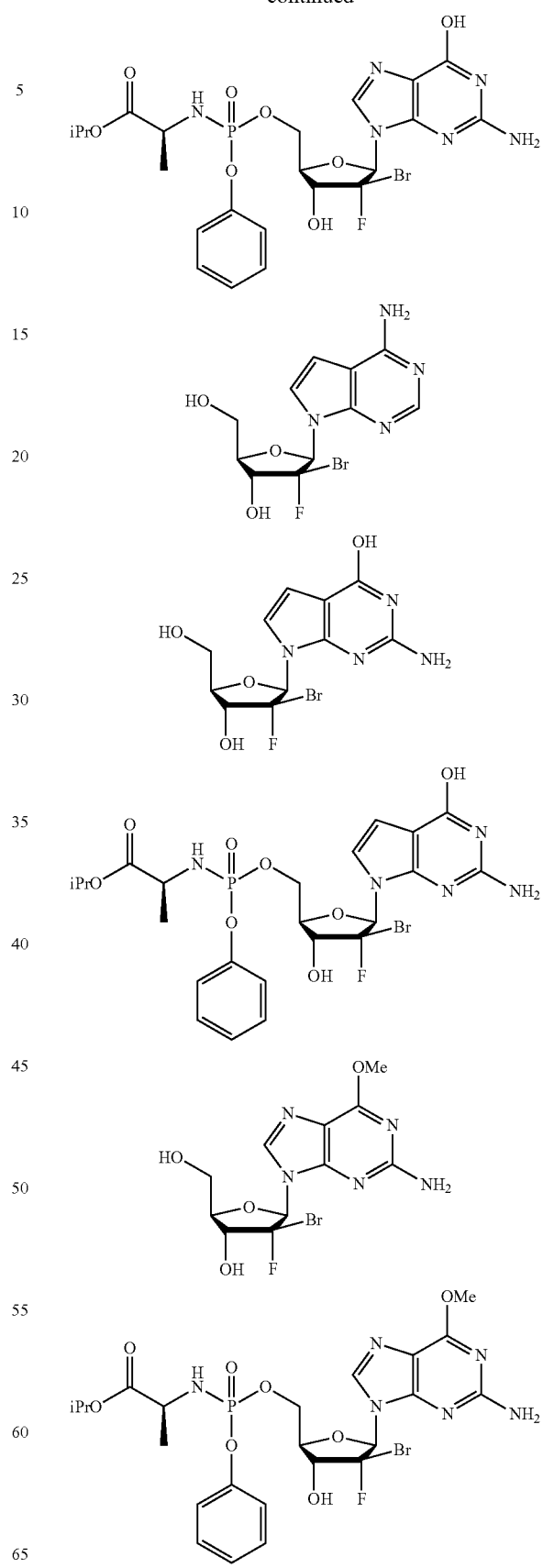

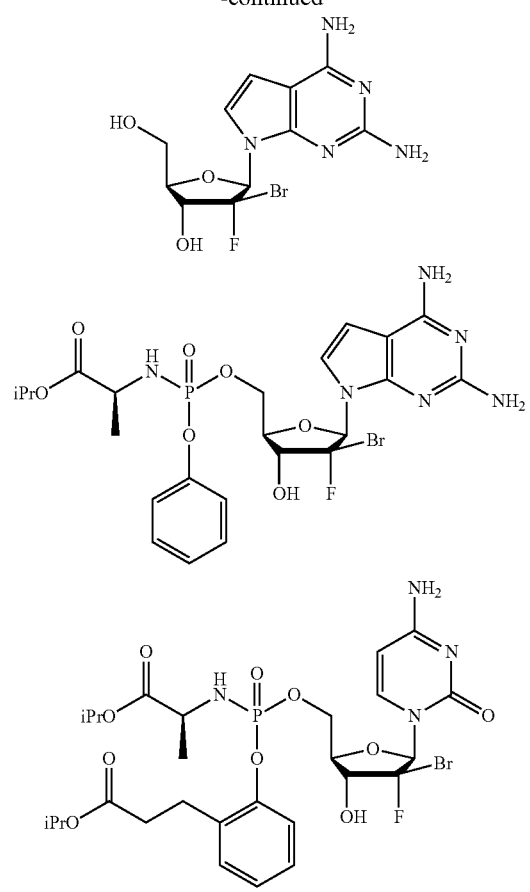
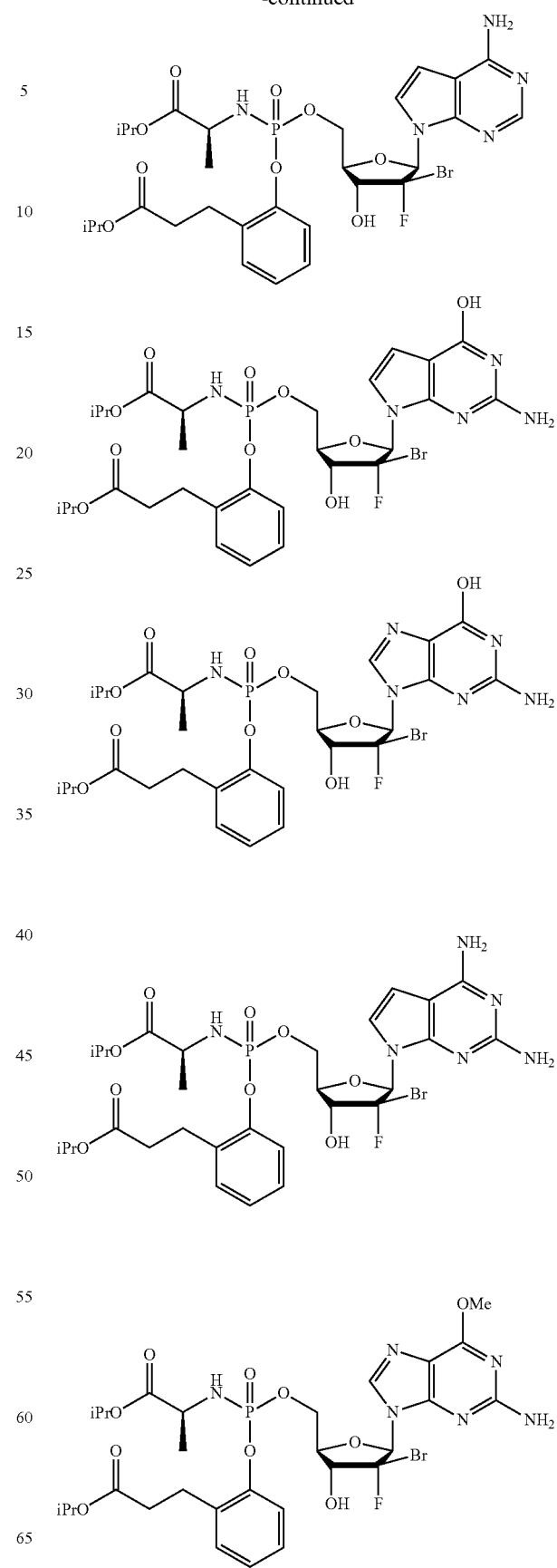

123
-continued
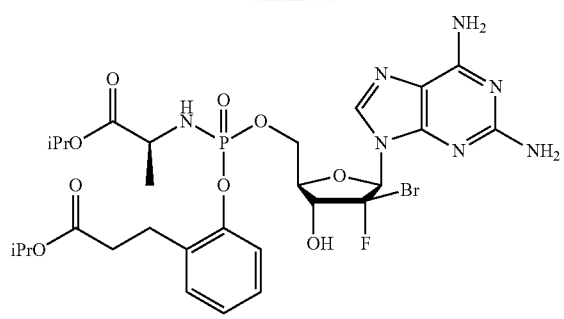
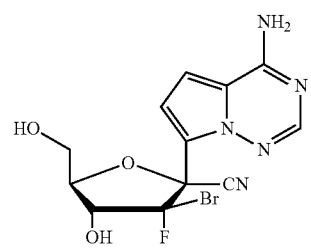
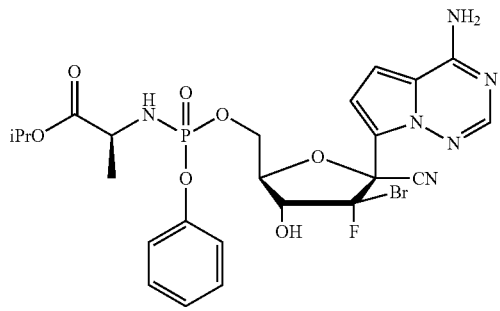
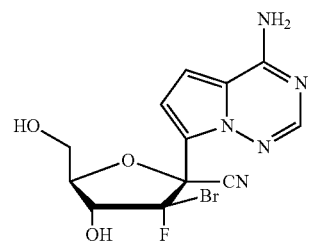
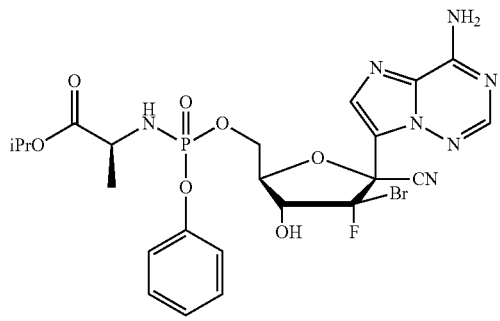
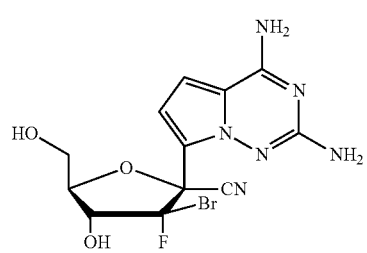
124
-continued
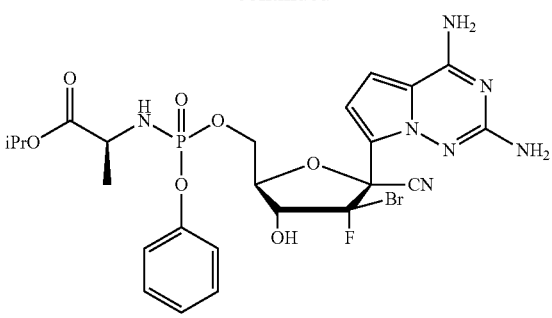
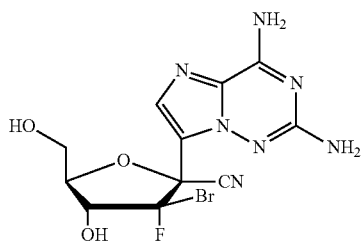
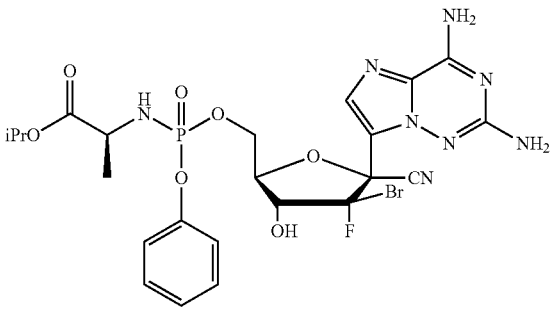
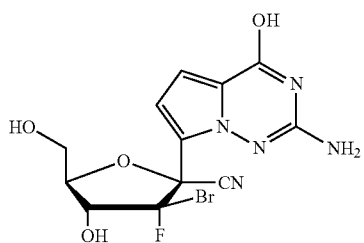
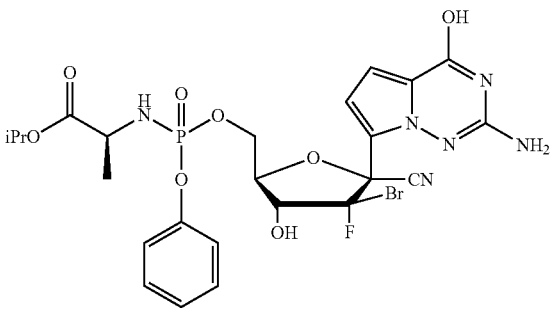
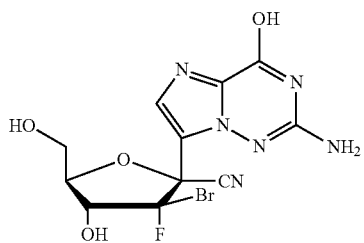

125
-continued
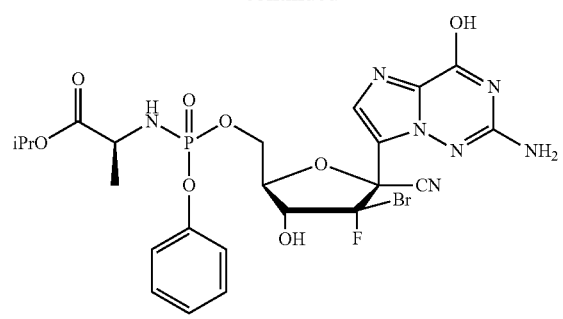
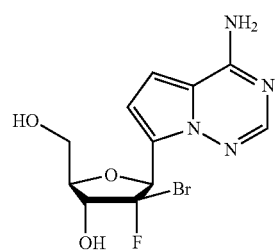
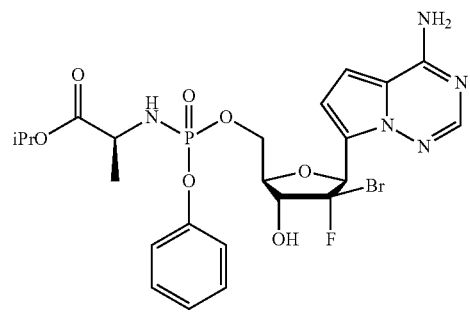
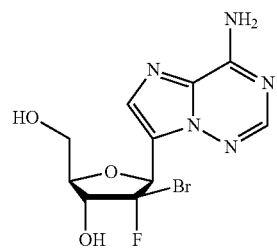
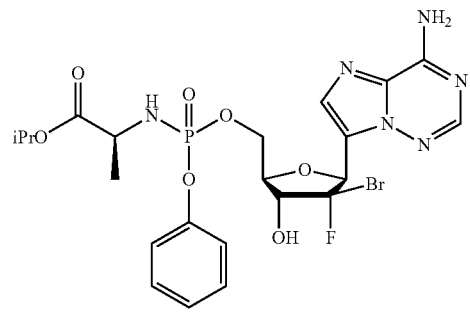
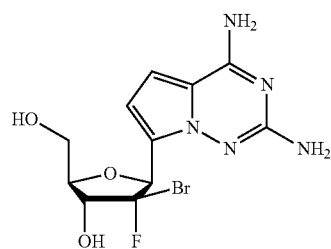
126
-continued
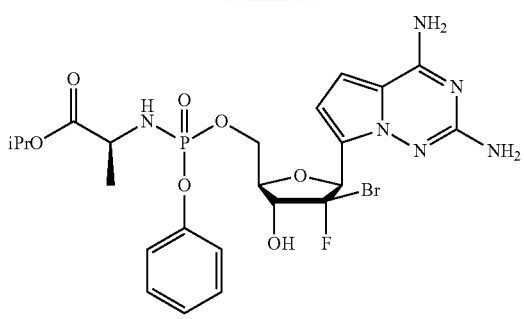
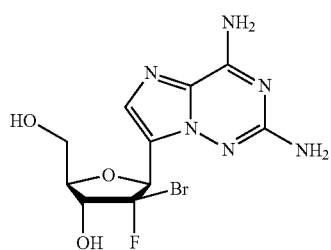
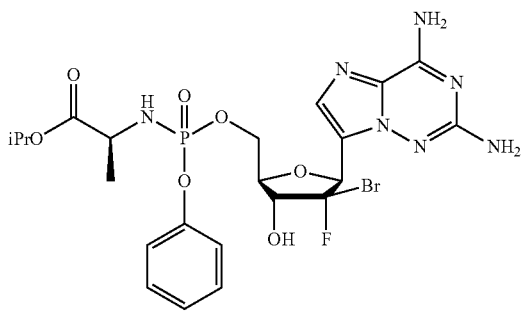
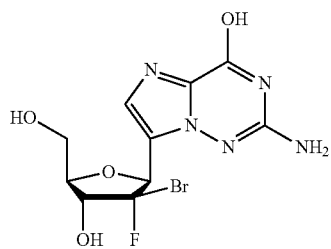
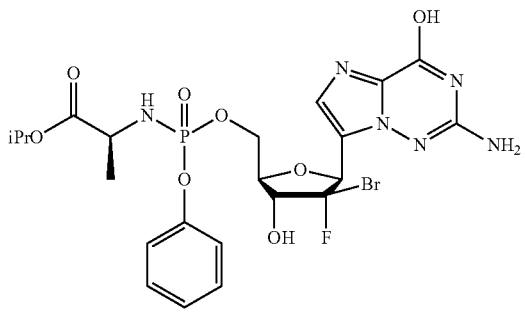
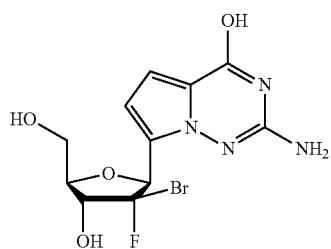

127
-continued
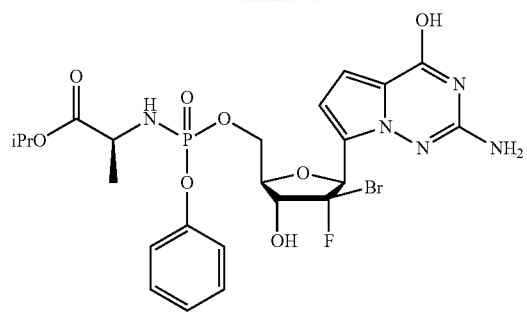
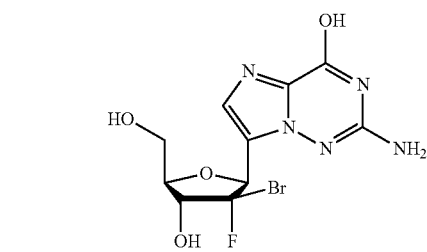
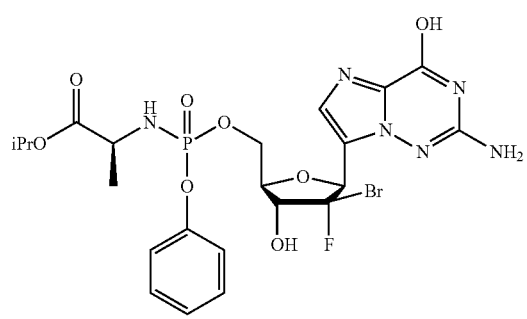
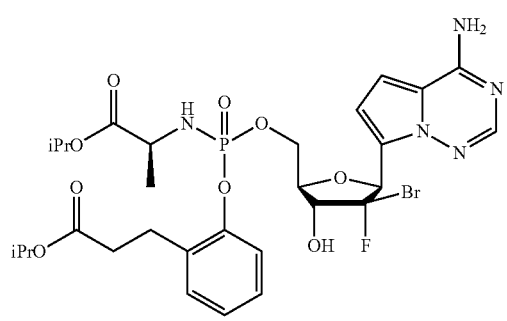
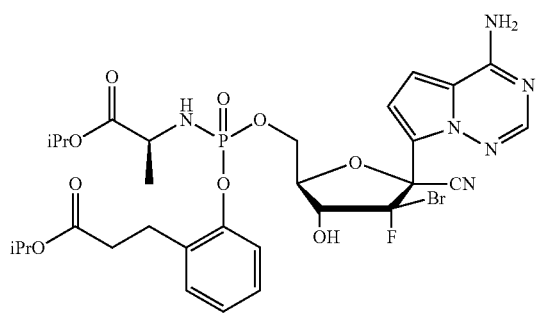
128
-continued
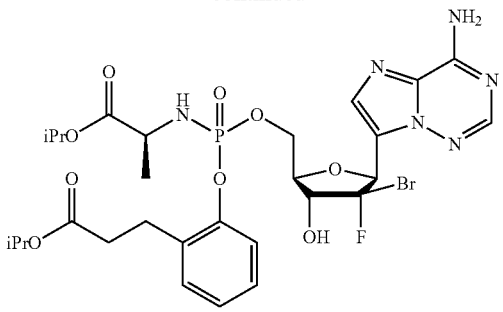
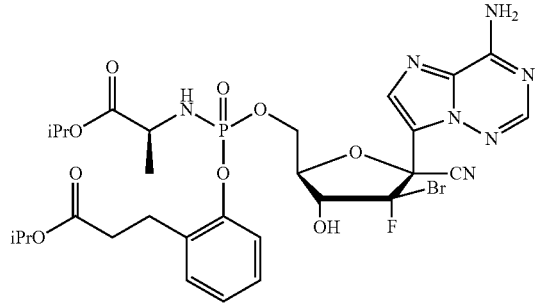
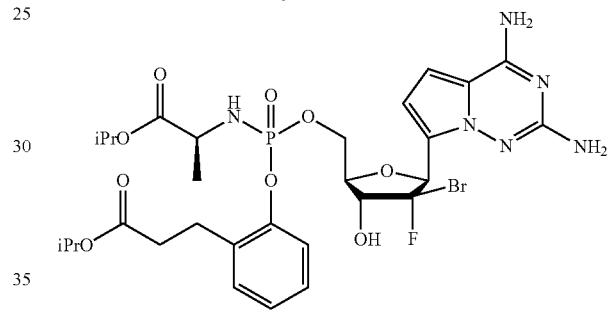
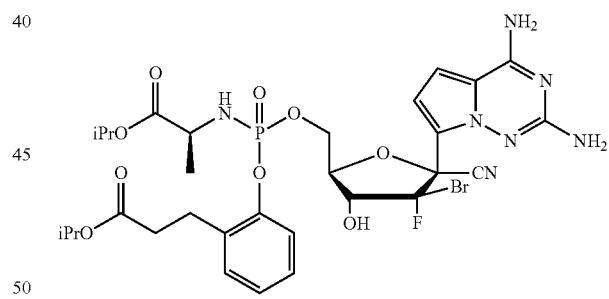
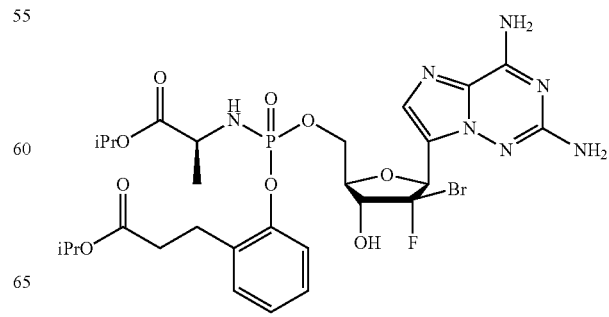

129
-continued
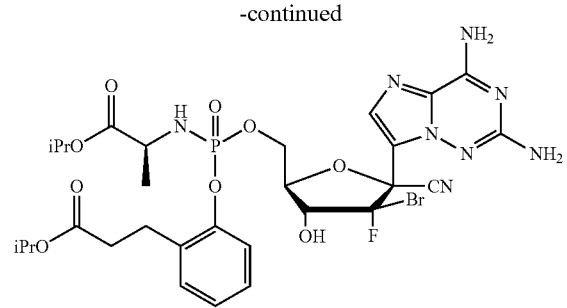
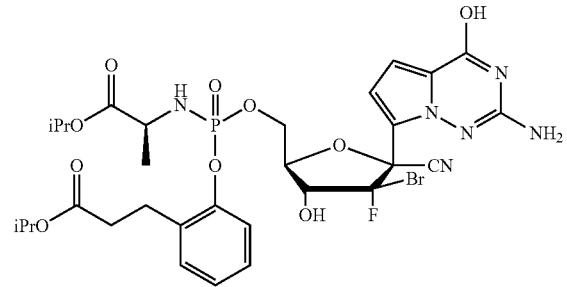
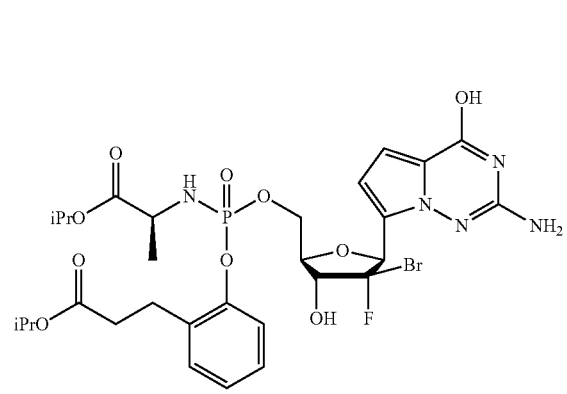
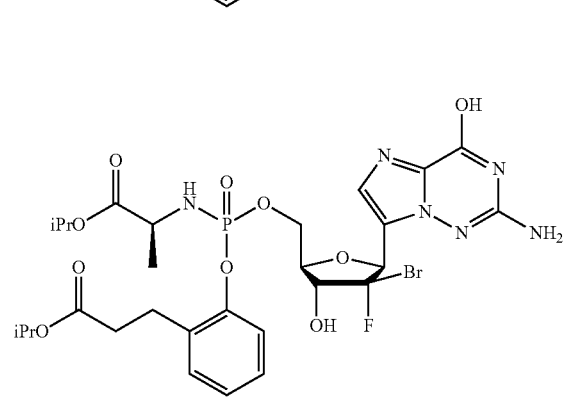
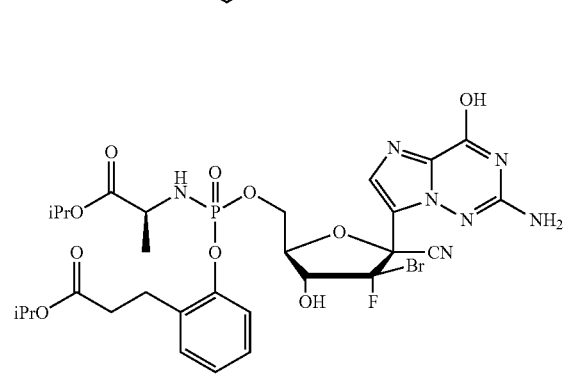
130
-continued
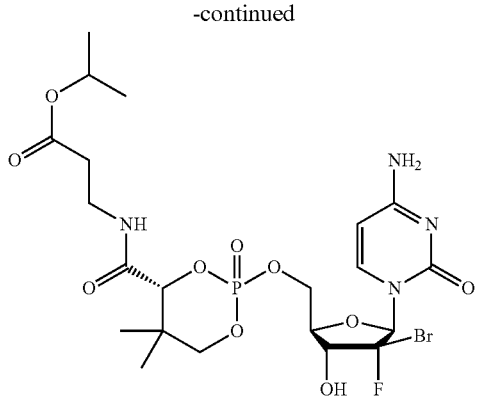
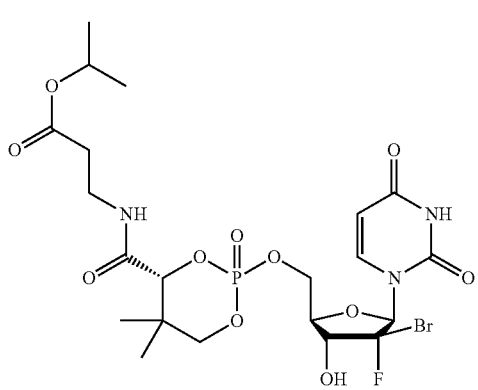
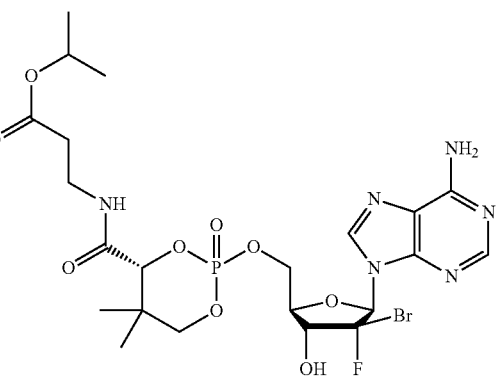
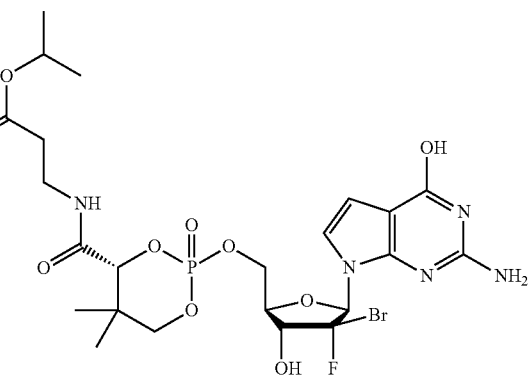

131
-continued
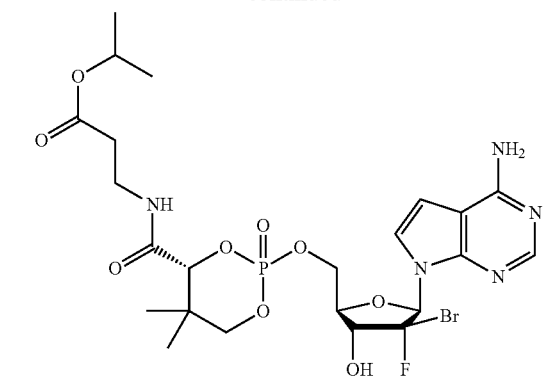
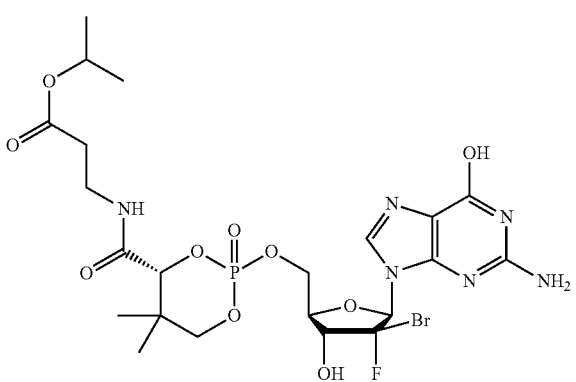
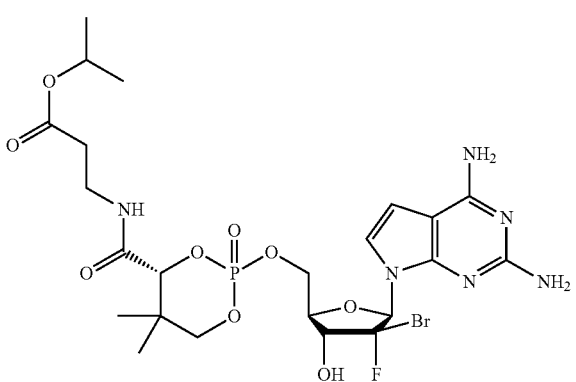
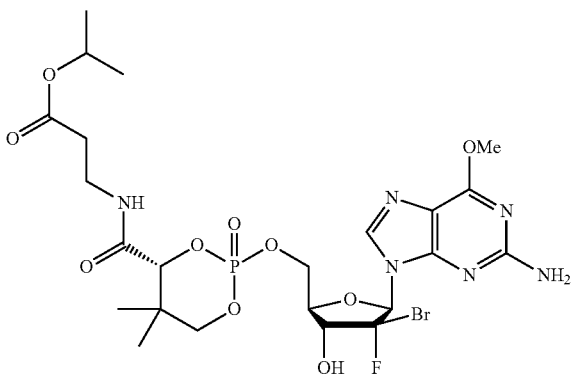
132
-continued
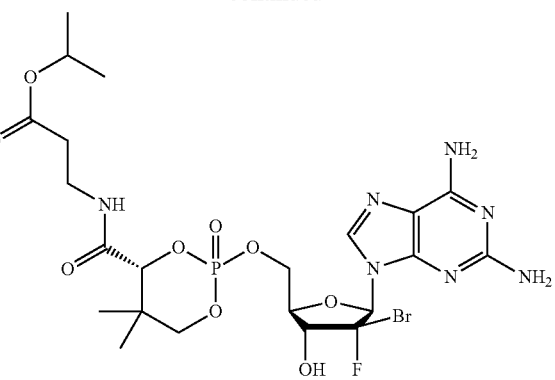
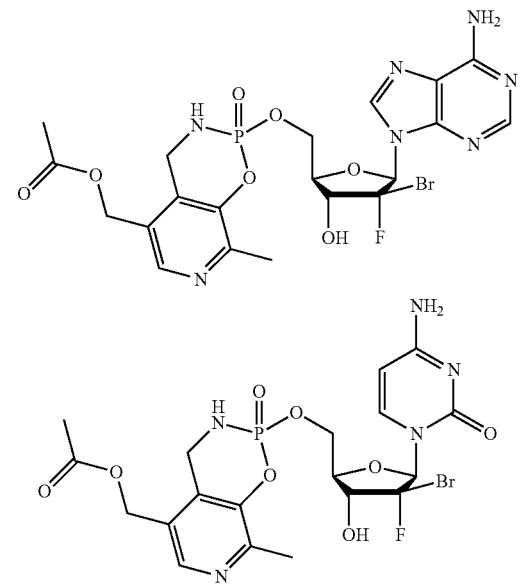
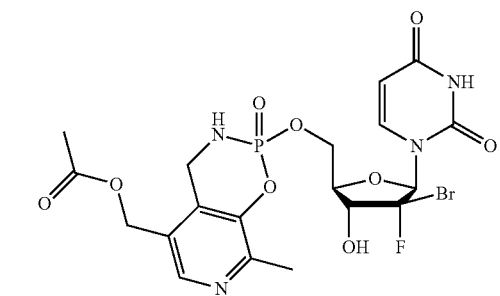
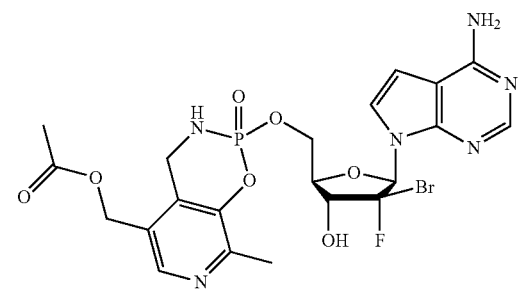

133
-continued
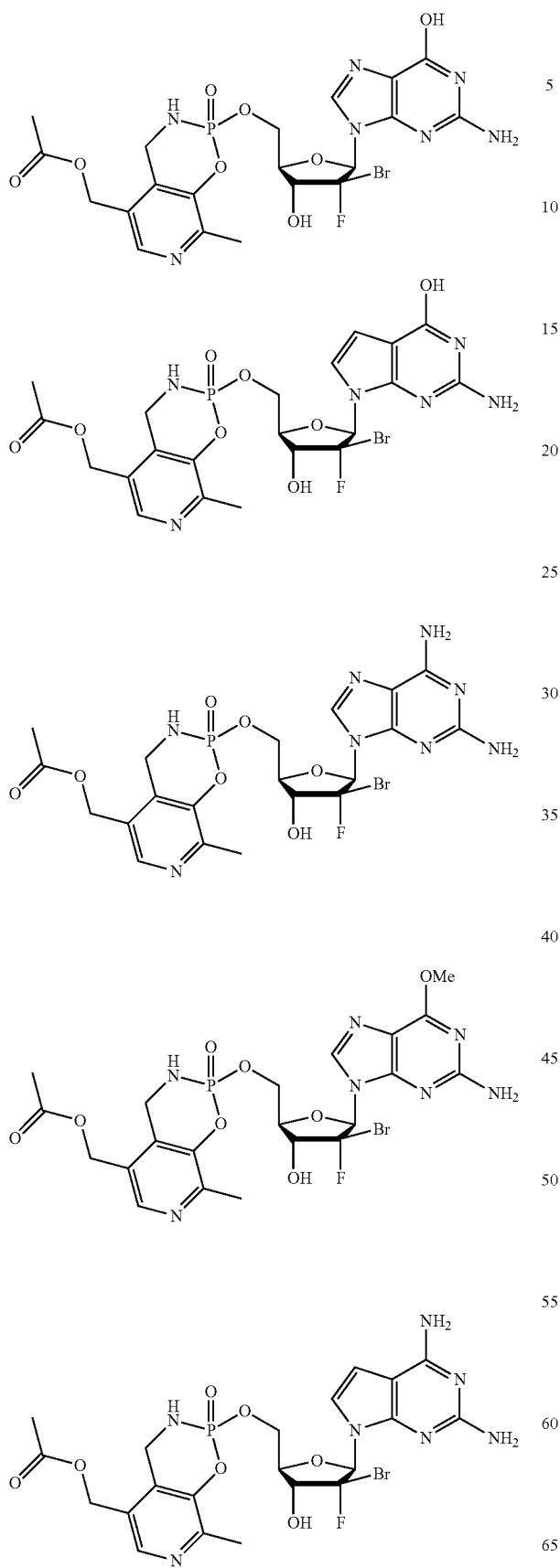
134
-continued
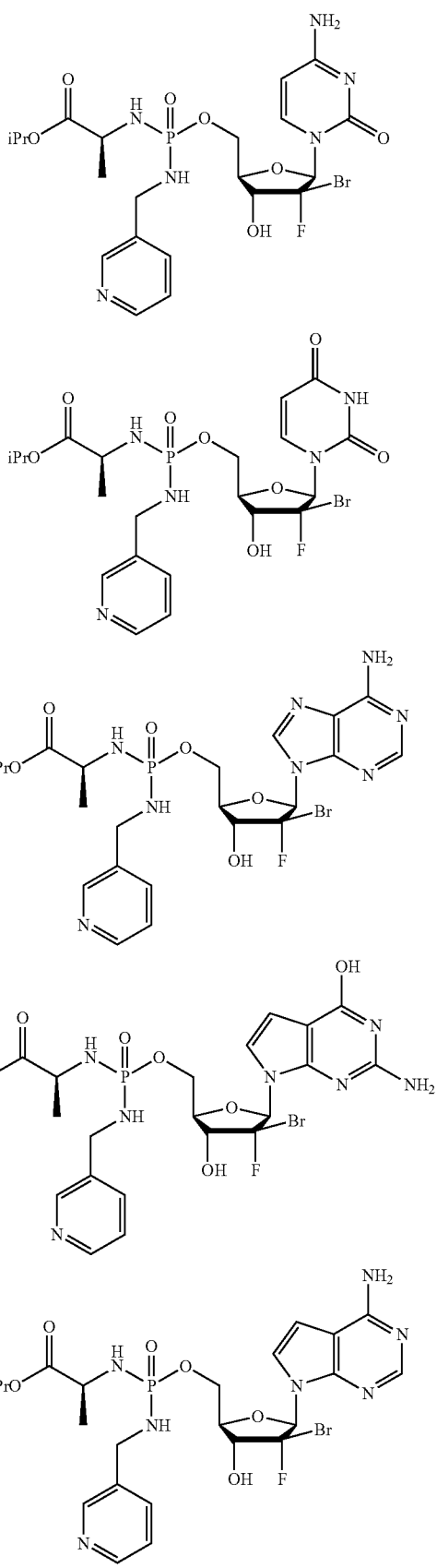

135
-continued
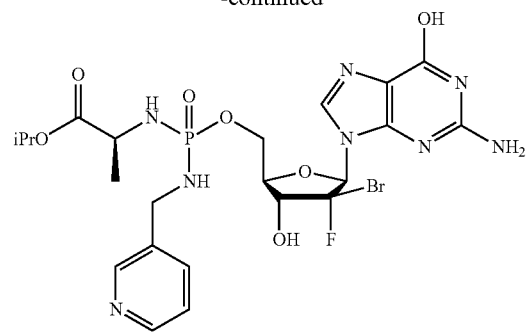
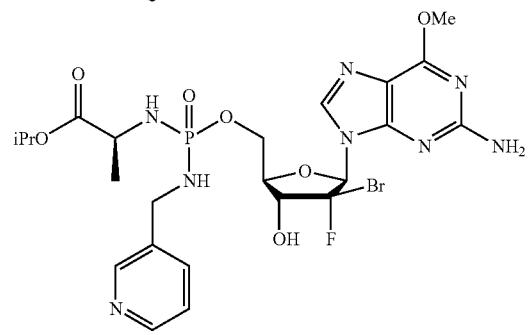
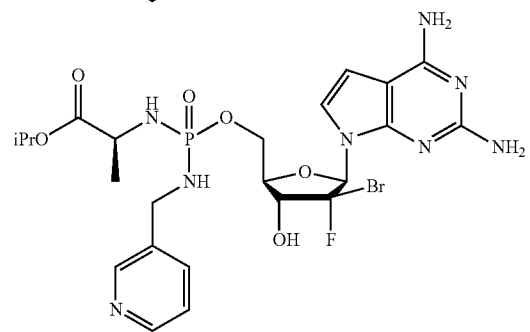
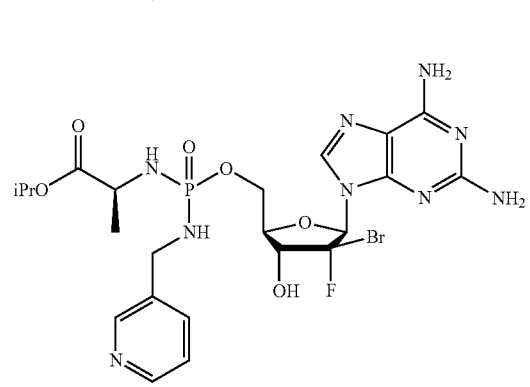
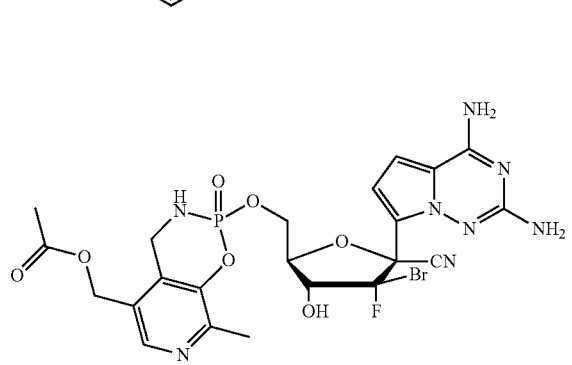
136
-continued
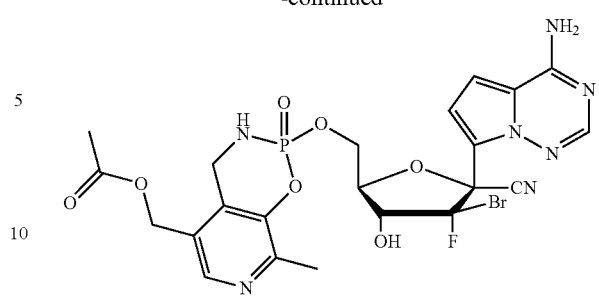
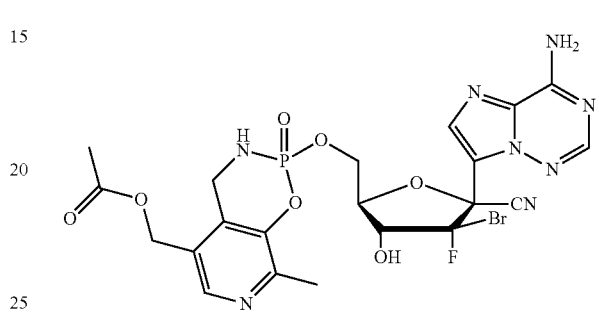
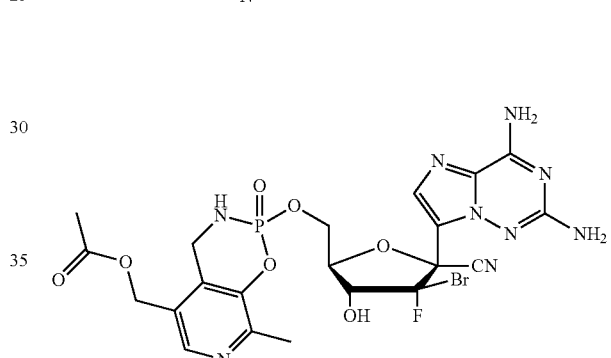
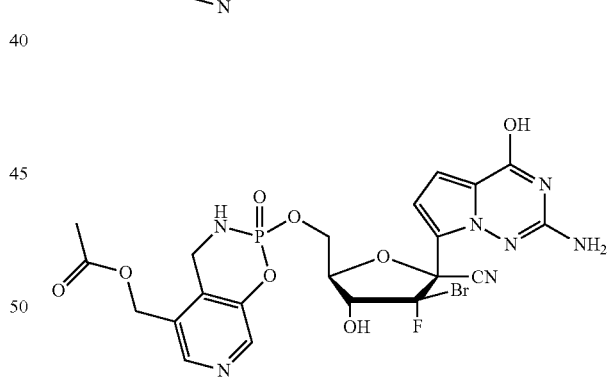
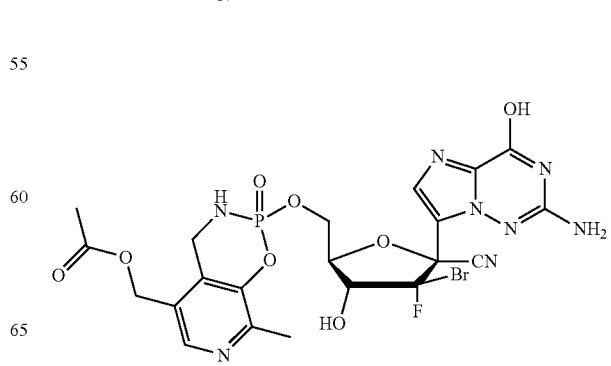

-continued

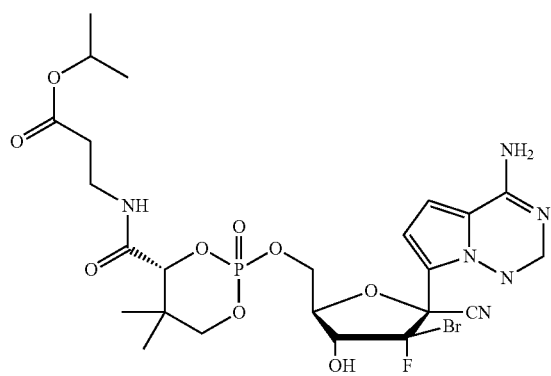

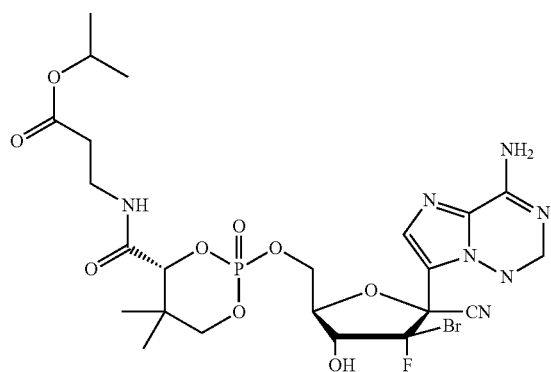

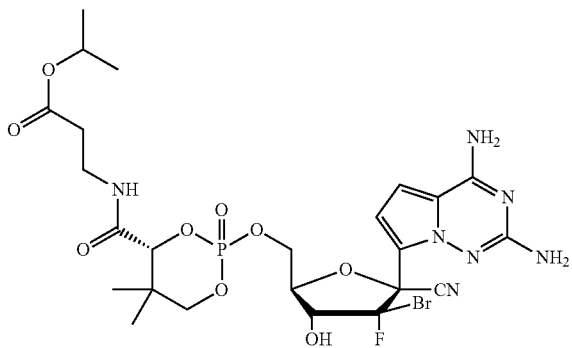

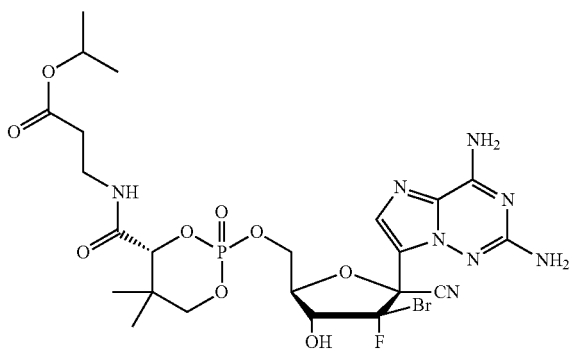

-continued

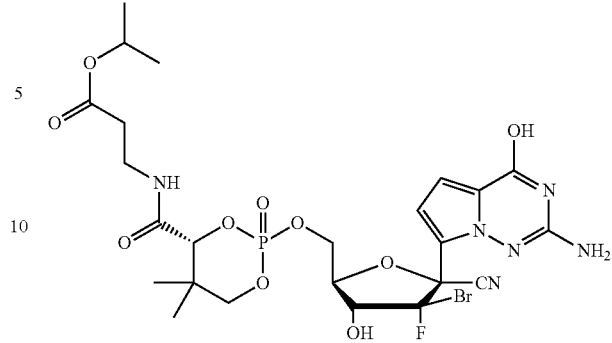

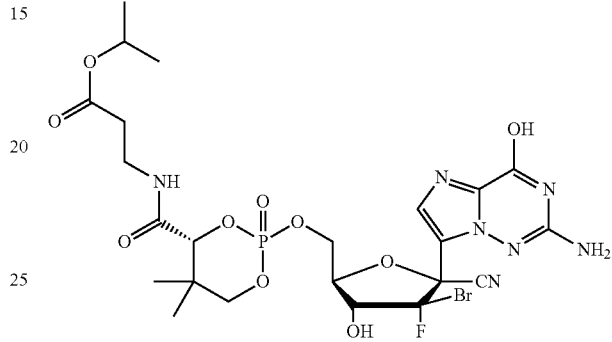

or pharmaceutically acceptable salts thereof.

5. A compound of claim 1, having the formula:

(Compound 9)

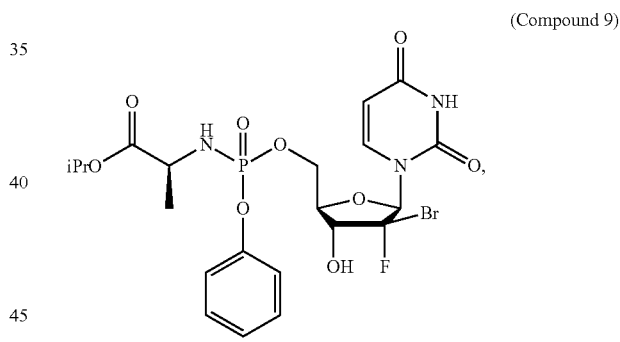

or a pharmaceutically acceptable salt thereof.

6. A compound of claim 1, having the formula:

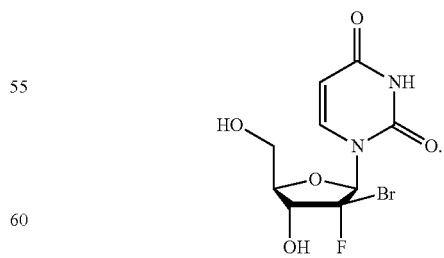

7. The compound of claim 1 wherein the sugar is partially deuterated.

8. A pharmaceutical composition comprising a compound of claim 1, and a pharmaceutically-acceptable carrier.

9. The composition of claim 8, wherein the composition is a transdermal composition or a nanoparticulate composition.

10. The pharmaceutical composition of claim 8, further comprising a second antiviral agent.

11. The pharmaceutical composition of claim 10, wherein the second antiviral agent is selected from the group consisting of an interferon, ribavirin, an NS3 protease inhibitor, an NS5A inhibitor, a non-nucleoside polymerase inhibitor, a helicase inhibitor, a polymerase inhibitor, a nucleotide or nucleoside analogue, an inhibitor of IRES dependent translation, and combinations thereof.

12. A method for treating a host infected with one or more viruses selected from the group consisting of HCV, Yellow fever, Dengue, Chikungunya and West Nile virus comprising administering an effective antiviral amount of a compound of claim 1 to a patient in need of treatment of one or more of an HCV, Yellow fever, Dengue, Chikungunya or West Nile virus infection.

13. The method of claim 12, wherein the virus is selected from the group consisting of HCV, Yellow fever, Dengue, Chikungunya and West Nile virus.

14. The method of claim 12, wherein the compound is administered in combination with another anti-Flaviviridae virus agent.

15. A method for treating a host infected with Norovirus or Saporovirus, comprising administering an effective antiviral amount of a compound of claim 1 to a patient in need of treatment of a Norovirus or Sapovirus infection.

16. A method for treating a host infected with RSV or influenza, comprising administering an effective antiviral amount of a compound of claim 1 to a patient in need of treatment of an RSV or influenza infection.

17. A method for treating a host infected with HEV, comprising administering an effective antiviral amount of a compound of claim 1 to a patient in need of treatment of an HEV infection.

* * * * *